(12) United States Patent
White et al.

(10) Patent No.: US 10,758,220 B2
(45) Date of Patent: Sep. 1, 2020

(54) DEVICES AND METHODS FOR PROVIDING SURGICAL ACCESS

(71) Applicant: Medos International Sarl, Le Locle (CH)

(72) Inventors: Michael White, Liestal (CH); Joern Richter, Kandern (DE); Jan Klett, Aesch (CH); Stephane Gully, Rixheim (FR); Veronique Christine Zollmann, Gebenstorf (CH); Richard Kocharian, Princeton, NJ (US)

(73) Assignee: Medos International Sarl, Le Locle (CH)

( * ) Notice: Subject to any disclaimer, the term of this patent is extended or adjusted under 35 U.S.C. 154(b) by 54 days.

(21) Appl. No.: 15/786,858

(22) Filed: Oct. 18, 2017

(65) Prior Publication Data
US 2018/0098789 A1    Apr. 12, 2018

Related U.S. Application Data

(63) Continuation-in-part of application No. 15/437,792, filed on Feb. 21, 2017, which is a continuation-in-part of application No. 15/254,877, filed on Sep. 1, 2016.
(Continued)

(51) Int. Cl.
*A61B 17/02* (2006.01)
*A61B 90/00* (2016.01)
(Continued)

(52) U.S. Cl.
CPC ........ *A61B 17/025* (2013.01); *A61B 1/00045* (2013.01); *A61B 1/00091* (2013.01);
(Continued)

(58) Field of Classification Search
CPC . A61B 17/34; A61B 17/3462; A61B 17/3423; A61B 1/313; A61B 1/3132
See application file for complete search history.

(56) References Cited

U.S. PATENT DOCUMENTS 4,318,401 A    3/1982 Zimmerman
4,573,448 A    3/1986 Kambin
(Continued)

FOREIGN PATENT DOCUMENTS

CN    102727309 B    11/2014
DE    94 15 039 U1   11/1994
(Continued)

OTHER PUBLICATIONS

Holt, J. S., et al., "A new table-fixed retractor for anterior odontoid screw fixation: technical note," J Neurosurg (Spine 3), 2003, v. 98, pp. 118-120.
(Continued)

*Primary Examiner* — Christopher J Beccia
(74) *Attorney, Agent, or Firm* — Nutter McClennen & Fish LLP

(57) ABSTRACT

Adjustable-length surgical access devices are disclosed herein, which can advantageously allow an overall length of the access device to be quickly and easily changed by the user. The access devices herein can reduce or eliminate the need to maintain an inventory of many different length access devices. In some embodiments, the length of the access device can be adjusted while the access device is inserted into the patient. This can reduce or eliminate the need to swap in and out several different access devices before arriving at an optimal length access device. This can also reduce or eliminate the need to change the access device that is inserted into a patient as the depth at which a surgical step is performed changes over the course of a procedure. Rather, the length of the access device can be adjusted in situ
(Continued)

and on-the-fly as needed or desired to accommodate different surgical depths.

15 Claims, 28 Drawing Sheets

Related U.S. Application Data

(60) Provisional application No. 62/468,475, filed on Mar. 8, 2017, provisional application No. 62/214,297, filed on Sep. 4, 2015.

(51) Int. Cl.

| | | |
|---|---|---|
| A61B 90/50 | (2016.01) | |
| A61B 90/57 | (2016.01) | |
| A61B 1/00 | (2006.01) | |
| A61B 1/012 | (2006.01) | |
| A61B 1/018 | (2006.01) | |
| A61B 1/05 | (2006.01) | |
| A61B 1/055 | (2006.01) | |
| A61B 1/07 | (2006.01) | |
| A61B 1/12 | (2006.01) | |
| A61B 1/233 | (2006.01) | |
| A61B 1/267 | (2006.01) | |
| A61B 1/313 | (2006.01) | |
| A61B 1/317 | (2006.01) | |
| A61B 1/32 | (2006.01) | |
| A61B 5/04 | (2006.01) | |
| A61B 5/06 | (2006.01) | |
| A61B 5/00 | (2006.01) | |
| A61B 17/00 | (2006.01) | |
| A61B 17/32 | (2006.01) | |
| A61B 17/34 | (2006.01) | |
| A61B 17/60 | (2006.01) | |
| A61B 17/70 | (2006.01) | |
| A61B 18/18 | (2006.01) | |
| A61F 2/44 | (2006.01) | |
| A61F 2/46 | (2006.01) | |
| A61B 34/20 | (2016.01) | |
| A61B 34/00 | (2016.01) | |
| A61B 90/30 | (2016.01) | |
| A61B 17/16 | (2006.01) | |
| A61B 17/17 | (2006.01) | |
| A61B 17/56 | (2006.01) | |
| A61B 18/00 | (2006.01) | |

(52) U.S. Cl.
CPC ...... *A61B 1/00096* (2013.01); *A61B 1/00103* (2013.01); *A61B 1/00128* (2013.01); *A61B 1/00133* (2013.01); *A61B 1/00135* (2013.01); *A61B 1/00154* (2013.01); *A61B 1/012* (2013.01); *A61B 1/018* (2013.01); *A61B 1/05* (2013.01); *A61B 1/051* (2013.01); *A61B 1/055* (2013.01); *A61B 1/07* (2013.01); *A61B 1/126* (2013.01); *A61B 1/233* (2013.01); *A61B 1/2676* (2013.01); *A61B 1/317* (2013.01); *A61B 1/3132* (2013.01); *A61B 1/3135* (2013.01); *A61B 1/32* (2013.01); *A61B 5/04001* (2013.01); *A61B 5/068* (2013.01); *A61B 5/407* (2013.01); *A61B 5/4041* (2013.01); *A61B 17/00234* (2013.01); *A61B 17/0218* (2013.01); *A61B 17/0293* (2013.01); *A61B 17/320068* (2013.01); *A61B 17/3421* (2013.01); *A61B 17/3423* (2013.01); *A61B 17/3462* (2013.01); *A61B 17/60* (2013.01); *A61B 17/708* (2013.01); *A61B 17/7032* (2013.01); *A61B 17/7074* (2013.01); *A61B 18/1815* (2013.01); *A61B 90/03* (2016.02); *A61B 90/361* (2016.02); *A61B 90/50* (2016.02); *A61B 90/57* (2016.02); *A61F 2/4455* (2013.01); *A61F 2/4611* (2013.01); *A61B 1/00149* (2013.01); *A61B 17/0206* (2013.01); *A61B 17/1637* (2013.01); *A61B 17/1671* (2013.01); *A61B 17/1757* (2013.01); *A61B 17/3439* (2013.01); *A61B 17/70* (2013.01); *A61B 17/7083* (2013.01); *A61B 34/70* (2016.02); *A61B 90/30* (2016.02); *A61B 2017/0034* (2013.01); *A61B 2017/00261* (2013.01); *A61B 2017/00314* (2013.01); *A61B 2017/00345* (2013.01); *A61B 2017/00407* (2013.01); *A61B 2017/00477* (2013.01); *A61B 2017/00557* (2013.01); *A61B 2017/00738* (2013.01); *A61B 2017/00831* (2013.01); *A61B 2017/00858* (2013.01); *A61B 2017/00871* (2013.01); *A61B 2017/00946* (2013.01); *A61B 2017/00991* (2013.01); *A61B 2017/0256* (2013.01); *A61B 2017/0262* (2013.01); *A61B 2017/320075* (2017.08); *A61B 2017/3443* (2013.01); *A61B 2017/3445* (2013.01); *A61B 2017/3447* (2013.01); *A61B 2017/3454* (2013.01); *A61B 2017/3484* (2013.01); *A61B 2017/564* (2013.01); *A61B 2018/00339* (2013.01); *A61B 2018/00565* (2013.01); *A61B 2018/00577* (2013.01); *A61B 2018/1861* (2013.01); *A61B 2018/1869* (2013.01); *A61B 2034/2055* (2016.02); *A61B 2090/034* (2016.02); *A61B 2090/036* (2016.02); *A61B 2090/08021* (2016.02); *A61B 2090/3983* (2016.02); *A61F 2002/4635* (2013.01)

(56) References Cited

U.S. PATENT DOCUMENTS

| | | |
|---|---|---|
| 4,646,738 A | 3/1987 | Trott |
| 4,678,459 A | 7/1987 | Onik et al. |
| 4,863,430 A | 9/1989 | Klyce et al. |
| 4,874,375 A | 10/1989 | Ellison |
| 4,888,146 A | 12/1989 | Dandeneau |
| 5,080,662 A | 1/1992 | Paul |
| 5,195,541 A | 3/1993 | Obenchain |
| 5,285,795 A | 2/1994 | Ryan et al. |
| 5,395,317 A | 3/1995 | Kambin |
| 5,439,464 A | 8/1995 | Shapiro |
| 5,529,580 A | 6/1996 | Kusunoki et al. |
| 5,540,706 A | 7/1996 | Aust et al. |
| 5,569,290 A | 10/1996 | McAfee |
| 5,591,187 A | 1/1997 | Dekel |
| 5,601,569 A | 2/1997 | Pisharodi |
| 5,615,690 A | 4/1997 | Giurtino et al. |
| 5,618,293 A | 4/1997 | Sample et al. |
| 5,662,300 A | 9/1997 | Michelson |
| 5,688,222 A | 11/1997 | Hluchy et al. |
| 5,730,754 A | 3/1998 | Obenchain |
| 5,733,242 A | 3/1998 | Rayburn et al. |
| 5,735,792 A | 4/1998 | Vanden Hoek et al. |
| 5,792,044 A | 8/1998 | Foley et al. |
| 5,820,623 A | 10/1998 | Ng |
| 5,885,300 A | 3/1999 | Tokuhashi et al. |
| 5,894,369 A | 4/1999 | Akiba et al. |
| 5,899,425 A | 5/1999 | Corey, Jr. et al. |
| 5,954,635 A | 9/1999 | Foley et al. |
| 6,053,907 A | 4/2000 | Zirps |
| 6,063,021 A | 5/2000 | Hossain et al. |
| 6,110,182 A | 8/2000 | Mowlai-Ashtiani |
| 6,200,322 B1 | 3/2001 | Branch et al. |
| 6,234,961 B1 | 5/2001 | Gray |
| 6,283,966 B1 | 9/2001 | Houfburg |

(56) References Cited

U.S. PATENT DOCUMENTS

| | | |
|---|---|---|
| 6,286,179 B1 | 9/2001 | Byrne |
| 6,296,644 B1 | 10/2001 | Saurat et al. |
| 6,322,498 B1 | 11/2001 | Gravenstein et al. |
| 6,354,992 B1 | 3/2002 | Kato |
| 6,371,968 B1 | 4/2002 | Kogasaka et al. |
| 6,383,191 B1 | 5/2002 | Zdeblick et al. |
| 6,447,446 B1 | 9/2002 | Smith et al. |
| 6,468,289 B1 | 10/2002 | Bonutti |
| 6,520,495 B1 | 2/2003 | La Mendola |
| 6,558,407 B1 | 5/2003 | Ivanko et al. |
| 6,575,899 B1 | 6/2003 | Foley et al. |
| 6,579,281 B2 | 6/2003 | Palmer et al. |
| 6,626,830 B1 | 9/2003 | Califiore et al. |
| 6,648,915 B2 | 11/2003 | Sazy |
| 6,676,597 B2 | 1/2004 | Guenst et al. |
| 6,685,724 B1 | 2/2004 | Haluck |
| 6,688,564 B2 | 2/2004 | Salvermoser et al. |
| 6,758,809 B2 | 7/2004 | Briscoe et al. |
| 6,808,505 B2 | 10/2004 | Kadan |
| 6,887,198 B2 | 5/2005 | Phillips et al. |
| 6,983,930 B1 | 1/2006 | La Mendola et al. |
| 7,087,058 B2 | 8/2006 | Cragg |
| 7,104,986 B2 | 9/2006 | Hovda et al. |
| 7,137,949 B2 | 11/2006 | Scirica et al. |
| 7,179,261 B2 | 2/2007 | Sicvol et al. |
| 7,182,731 B2 | 2/2007 | Nguyen et al. |
| 7,226,413 B2 | 6/2007 | McKinley |
| 7,341,556 B2 | 3/2008 | Shalman |
| 7,434,325 B2 | 10/2008 | Foley et al. |
| 7,491,168 B2 | 2/2009 | Raymond et al. |
| 7,591,790 B2 | 9/2009 | Pflueger |
| 7,594,888 B2 | 9/2009 | Raymond et al. |
| 7,618,431 B2 | 11/2009 | Roehm, III et al. |
| 7,636,596 B2 | 12/2009 | Solar |
| 7,637,905 B2 | 12/2009 | Saadat et al. |
| 7,641,659 B2 | 1/2010 | Emstad et al. |
| 7,771,384 B2 | 8/2010 | Ravo |
| 7,794,456 B2 | 9/2010 | Sharps et al. |
| 7,811,303 B2 | 10/2010 | Fallin et al. |
| 7,931,579 B2 | 4/2011 | Bertolero et al. |
| 7,946,981 B1 | 5/2011 | Cubb |
| 7,951,141 B2 | 5/2011 | Sharps et al. |
| 7,959,564 B2 | 6/2011 | Ritland |
| 7,988,623 B2 | 8/2011 | Pagliuca et al. |
| 8,007,492 B2 | 8/2011 | DiPoto et al. |
| 8,038,606 B2 | 10/2011 | Otawara |
| 8,043,381 B2 | 10/2011 | Hestad et al. |
| 8,062,218 B2 | 11/2011 | Sebastian et al. |
| 8,079,952 B2 | 12/2011 | Fujimoto |
| 8,092,464 B2 | 1/2012 | McKay |
| 8,096,944 B2 | 1/2012 | Harrel |
| 8,202,216 B2 | 6/2012 | Melkent et al. |
| 8,236,006 B2 | 8/2012 | Hamada |
| 8,303,492 B2 | 11/2012 | Ito |
| 8,333,690 B2 | 12/2012 | Ikeda |
| 8,360,970 B2 | 1/2013 | Mangiardi |
| 8,372,131 B2 | 2/2013 | Hestad et al. |
| 8,382,048 B2 | 2/2013 | Nesper et al. |
| 8,397,335 B2 | 3/2013 | Gordin et al. |
| 8,419,625 B2 | 4/2013 | Ito |
| 8,435,174 B2 | 5/2013 | Cropper et al. |
| 8,460,180 B1 | 6/2013 | Zarate et al. |
| 8,460,186 B2 | 6/2013 | Ortiz et al. |
| 8,460,310 B2 | 6/2013 | Stern |
| 8,518,087 B2 | 8/2013 | Lopez et al. |
| 8,535,220 B2 | 9/2013 | Mondschein |
| 8,556,809 B2 | 10/2013 | Vijayanagar |
| 8,585,726 B2 | 11/2013 | Yoon et al. |
| 8,602,979 B2 | 12/2013 | Kitano |
| 8,622,894 B2 | 1/2014 | Banik et al. |
| 8,636,655 B1 | 1/2014 | Childs |
| 8,648,932 B2 | 2/2014 | Talbert et al. |
| 8,690,764 B2 | 4/2014 | Clark et al. |
| 8,721,536 B2 | 5/2014 | Marino et al. |
| 8,740,779 B2 | 6/2014 | Yoshida |
| 8,784,421 B2 | 7/2014 | Carrison et al. |
| 8,821,378 B2 | 9/2014 | Morgenstern Lopez et al. |
| 8,834,507 B2 | 9/2014 | Mire et al. |
| 8,845,734 B2 | 9/2014 | Weiman |
| 8,852,242 B2 | 10/2014 | Morgenstern Lopez et al. |
| 8,870,753 B2 | 10/2014 | Boulais et al. |
| 8,870,756 B2 | 10/2014 | Maurice |
| 8,876,712 B2 | 11/2014 | Yee et al. |
| 8,888,689 B2 | 11/2014 | Poll et al. |
| 8,894,573 B2 | 11/2014 | Loftus et al. |
| 8,894,653 B2 | 11/2014 | Solsberg et al. |
| 8,926,502 B2 | 1/2015 | Levy et al. |
| 8,932,207 B2 | 1/2015 | Greenburg et al. |
| 8,932,360 B2 | 1/2015 | Womble et al. |
| 8,936,545 B2 | 1/2015 | To |
| 8,936,605 B2 | 1/2015 | Greenberg |
| 8,952,312 B2 | 2/2015 | Blanquart et al. |
| 8,961,404 B2 | 2/2015 | Ito |
| 8,972,714 B2 | 3/2015 | Talbert et al. |
| 8,974,381 B1 | 3/2015 | Lovell et al. |
| 8,986,199 B2 | 3/2015 | Weisenburgh, II et al. |
| 8,992,580 B2 | 3/2015 | Bar et al. |
| 9,028,522 B1 | 5/2015 | Prado |
| 9,050,036 B2 | 6/2015 | Poll et al. |
| 9,050,037 B2 | 6/2015 | Poll et al. |
| 9,050,146 B2 | 6/2015 | Woolley et al. |
| 9,055,936 B2 | 6/2015 | Mire et al. |
| 9,072,431 B2 | 7/2015 | Adams et al. |
| 9,078,562 B2 | 7/2015 | Poll et al. |
| 9,123,602 B2 | 9/2015 | Blanquart |
| 9,131,948 B2 | 9/2015 | Fang et al. |
| 9,144,374 B2 | 9/2015 | Maurice, Jr. |
| 9,153,609 B2 | 10/2015 | Blanquart |
| 9,198,674 B2 | 12/2015 | Benson et al. |
| 9,211,059 B2 | 12/2015 | Drach et al. |
| 9,216,016 B2 | 12/2015 | Fiechter et al. |
| 9,216,125 B2 | 12/2015 | Sklar |
| 9,226,647 B2 | 1/2016 | Sugawara |
| 9,232,935 B2 | 1/2016 | Brand et al. |
| 9,247,997 B2 | 2/2016 | Stefanchik et al. |
| 9,265,491 B2 | 2/2016 | Lins et al. |
| 9,277,928 B2 | 3/2016 | Morgenstern Lopez |
| 9,307,972 B2 | 4/2016 | Lovell et al. |
| 9,320,419 B2 | 4/2016 | Kirma et al. |
| RE46,007 E | 5/2016 | Banik et al. |
| RE46,062 E | 7/2016 | James et al. |
| 9,386,971 B1 | 7/2016 | Casey et al. |
| 9,387,313 B2 | 7/2016 | Culbert et al. |
| 9,414,828 B2 | 8/2016 | Abidin et al. |
| 9,462,234 B2 | 10/2016 | Blanquart et al. |
| 9,486,296 B2 | 11/2016 | Mire et al. |
| 9,492,194 B2 | 11/2016 | Morgenstern Lopez et al. |
| 9,509,917 B2 | 11/2016 | Blanquart et al. |
| 9,510,853 B2 | 12/2016 | Aljuri et al. |
| 9,516,239 B2 | 12/2016 | Blanquart et al. |
| 9,522,017 B2 | 12/2016 | Poll et al. |
| 9,526,401 B2 | 12/2016 | Saadat et al. |
| 9,579,012 B2 | 2/2017 | Vazales et al. |
| 9,603,510 B2 | 3/2017 | Ammirati |
| 9,603,610 B2 | 3/2017 | Richter et al. |
| 9,610,007 B2 | 4/2017 | Kienzle et al. |
| 9,610,095 B2 | 4/2017 | To |
| 9,622,650 B2 | 4/2017 | Blanquart |
| 9,629,521 B2 | 4/2017 | Ratnakar |
| 9,641,815 B2 | 5/2017 | Richardson et al. |
| 9,655,605 B2 | 5/2017 | Serowski et al. |
| 9,655,639 B2 | 5/2017 | Mark |
| 9,668,643 B2 | 6/2017 | Kennedy, II et al. |
| 9,675,235 B2 | 6/2017 | Lieponis |
| 9,700,378 B2 | 7/2017 | Mowlai-Ashtiani |
| 9,706,905 B2 | 7/2017 | Levy |
| 2002/0022762 A1 | 2/2002 | Beane et al. |
| 2002/0138020 A1 | 9/2002 | Pflueger |
| 2003/0083555 A1 | 5/2003 | Hunt et al. |
| 2003/0171744 A1 | 9/2003 | Leung et al. |
| 2003/0191474 A1 | 10/2003 | Cragg et al. |
| 2004/0122446 A1 | 6/2004 | Solar |
| 2004/0127992 A1 | 7/2004 | Serhan et al. |
| 2004/0143165 A1 | 7/2004 | Alleyne |

(56) References Cited

U.S. PATENT DOCUMENTS

| | | |
|---|---|---|
| 2004/0158286 A1 | 8/2004 | Roux et al. |
| 2005/0075644 A1 | 4/2005 | DiPoto et al. |
| 2005/0085692 A1 | 4/2005 | Kiehn et al. |
| 2005/0090848 A1 | 4/2005 | Adams |
| 2005/0187570 A1 | 8/2005 | Nguyen et al. |
| 2005/0256525 A1 | 11/2005 | Culbert et al. |
| 2006/0041270 A1 | 2/2006 | Lenker et al. |
| 2006/0052671 A1 | 3/2006 | McCarthy |
| 2006/0074445 A1 | 4/2006 | Gerber et al. |
| 2006/0200186 A1* | 9/2006 | Marchek ............ A61B 17/0218 606/191 |
| 2006/0206118 A1 | 9/2006 | Kim et al. |
| 2006/0264895 A1 | 11/2006 | Flanders |
| 2007/0049794 A1 | 3/2007 | Glassenberg et al. |
| 2007/0055259 A1 | 3/2007 | Norton et al. |
| 2007/0129634 A1 | 6/2007 | Hickey et al. |
| 2007/0149975 A1 | 6/2007 | Oliver et al. |
| 2007/0203396 A1 | 8/2007 | McCutcheon et al. |
| 2007/0213716 A1 | 9/2007 | Lenke et al. |
| 2007/0225556 A1 | 9/2007 | Ortiz et al. |
| 2007/0255100 A1 | 11/2007 | Barlow et al. |
| 2007/0260113 A1 | 11/2007 | Otawara |
| 2007/0260184 A1 | 11/2007 | Justis et al. |
| 2008/0015621 A1 | 1/2008 | Emanuel |
| 2008/0033251 A1 | 2/2008 | Araghi |
| 2008/0064921 A1 | 3/2008 | Larkin et al. |
| 2008/0064928 A1 | 3/2008 | Otawara |
| 2008/0081951 A1 | 4/2008 | Frasier et al. |
| 2008/0139879 A1 | 6/2008 | Olson et al. |
| 2008/0147109 A1 | 6/2008 | Kambin et al. |
| 2008/0183189 A1 | 7/2008 | Teichman et al. |
| 2008/0188714 A1 | 8/2008 | McCaffrey |
| 2008/0242930 A1 | 10/2008 | Hanypsiak et al. |
| 2008/0260342 A1 | 10/2008 | Kuroiwa |
| 2009/0018566 A1 | 1/2009 | Escudero et al. |
| 2009/0024158 A1 | 1/2009 | Viker |
| 2009/0062871 A1 | 3/2009 | Chin et al. |
| 2009/0105543 A1 | 4/2009 | Miller et al. |
| 2009/0149857 A1 | 6/2009 | Culbert et al. |
| 2009/0156898 A1 | 6/2009 | Ichimura |
| 2009/0187080 A1 | 7/2009 | Seex |
| 2009/0240111 A1 | 9/2009 | Kessler et al. |
| 2009/0287061 A1 | 11/2009 | Feigenbaum et al. |
| 2009/0318765 A1 | 12/2009 | Torii |
| 2010/0004651 A1 | 1/2010 | Biyani |
| 2010/0022841 A1 | 1/2010 | Takahashi et al. |
| 2010/0076476 A1 | 3/2010 | To et al. |
| 2010/0114147 A1 | 5/2010 | Biyani |
| 2010/0151161 A1 | 6/2010 | Da Rolo |
| 2010/0161060 A1 | 6/2010 | Schaller et al. |
| 2010/0256446 A1 | 10/2010 | Raju |
| 2010/0280325 A1 | 11/2010 | Ibrahim et al. |
| 2010/0284580 A1 | 11/2010 | OuYang et al. |
| 2010/0286477 A1 | 11/2010 | OuYang et al. |
| 2010/0312053 A1 | 12/2010 | Larsen |
| 2010/0317928 A1 | 12/2010 | Subramaniam |
| 2011/0028791 A1 | 2/2011 | Marino et al. |
| 2011/0054507 A1 | 3/2011 | Batten et al. |
| 2011/0056500 A1 | 3/2011 | Shin et al. |
| 2011/0073594 A1 | 3/2011 | Bonn |
| 2011/0098628 A1 | 4/2011 | Yeung et al. |
| 2011/0106261 A1 | 5/2011 | Chin et al. |
| 2011/0112588 A1 | 5/2011 | Linderman et al. |
| 2011/0125158 A1 | 5/2011 | Diwan et al. |
| 2011/0130634 A1 | 6/2011 | Solitario, Jr. et al. |
| 2011/0201888 A1 | 8/2011 | Verner |
| 2011/0230965 A1 | 9/2011 | Schell et al. |
| 2011/0257478 A1 | 10/2011 | Kleiner et al. |
| 2011/0295070 A1 | 12/2011 | Yasunaga |
| 2011/0319941 A1 | 12/2011 | Bar et al. |
| 2012/0016192 A1 | 1/2012 | Jansen et al. |
| 2012/0029412 A1 | 2/2012 | Yeung et al. |
| 2012/0095296 A1 | 4/2012 | Trieu et al. |
| 2012/0101338 A1 | 4/2012 | O'Prey et al. |
| 2012/0111682 A1 | 5/2012 | Andre |
| 2012/0116170 A1 | 5/2012 | Vayser et al. |
| 2012/0157788 A1 | 6/2012 | Serowski et al. |
| 2012/0209273 A1 | 8/2012 | Zaretzka et al. |
| 2012/0221007 A1 | 8/2012 | Batten et al. |
| 2012/0232350 A1 | 9/2012 | Seex |
| 2012/0232552 A1 | 9/2012 | Morgenstern Lopez et al. |
| 2012/0298820 A1 | 11/2012 | Manolidis |
| 2012/0316400 A1 | 12/2012 | Vijayanagar |
| 2013/0103067 A1 | 4/2013 | Fabro et al. |
| 2013/0103103 A1 | 4/2013 | Mire et al. |
| 2013/0150670 A1 | 6/2013 | O'Prey et al. |
| 2013/0150674 A1 | 6/2013 | Haig et al. |
| 2013/0172674 A1 | 7/2013 | Kennedy, II et al. |
| 2013/0172676 A1 | 7/2013 | Levy et al. |
| 2013/0211202 A1 | 8/2013 | Perez-Cruet et al. |
| 2013/0282022 A1 | 10/2013 | Yousef |
| 2013/0289399 A1 | 10/2013 | Choi et al. |
| 2013/0303846 A1 | 11/2013 | Cybulski et al. |
| 2013/0304106 A1 | 11/2013 | Breznock |
| 2014/0025121 A1 | 1/2014 | Foley et al. |
| 2014/0066940 A1 | 3/2014 | Fang et al. |
| 2014/0074170 A1 | 3/2014 | Mertens et al. |
| 2014/0088367 A1 | 3/2014 | DiMauro et al. |
| 2014/0142584 A1 | 5/2014 | Sweeney |
| 2014/0148647 A1 | 5/2014 | Okazaki |
| 2014/0163319 A1 | 6/2014 | Blanquart et al. |
| 2014/0180321 A1 | 6/2014 | Dias et al. |
| 2014/0194697 A1 | 7/2014 | Seex |
| 2014/0215736 A1 | 8/2014 | Gomez et al. |
| 2014/0221749 A1 | 8/2014 | Grant et al. |
| 2014/0257332 A1 | 9/2014 | Lastrozna |
| 2014/0257489 A1 | 9/2014 | Warren et al. |
| 2014/0275793 A1 | 9/2014 | Song |
| 2014/0275799 A1 | 9/2014 | Schuele |
| 2014/0276840 A1 | 9/2014 | Richter et al. |
| 2014/0276916 A1 | 9/2014 | Ahluwalia et al. |
| 2014/0277204 A1 | 9/2014 | Sandhu |
| 2014/0285644 A1 | 9/2014 | Richardson et al. |
| 2014/0318582 A1 | 10/2014 | Mowlai-Ashtiani |
| 2014/0336764 A1 | 11/2014 | Masson et al. |
| 2014/0357945 A1 | 12/2014 | Duckworth |
| 2014/0378985 A1* | 12/2014 | Mafi .................. A61B 17/3421 606/93 |
| 2015/0018623 A1 | 1/2015 | Friedrich et al. |
| 2015/0065795 A1 | 3/2015 | Titus |
| 2015/0073218 A1 | 3/2015 | Ito |
| 2015/0112398 A1 | 4/2015 | Morgenstern Lopez et al. |
| 2015/0133727 A1 | 5/2015 | Bacich et al. |
| 2015/0164496 A1 | 6/2015 | Karpowicz et al. |
| 2015/0216593 A1 | 8/2015 | Biyani |
| 2015/0223671 A1 | 8/2015 | Sung et al. |
| 2015/0223676 A1 | 8/2015 | Bayer et al. |
| 2015/0230697 A1 | 8/2015 | Phee et al. |
| 2015/0238073 A1 | 8/2015 | Charles et al. |
| 2015/0272694 A1 | 10/2015 | Charles |
| 2015/0313585 A1 | 11/2015 | Abidin et al. |
| 2015/0335389 A1 | 11/2015 | Greenberg |
| 2015/0342621 A1 | 12/2015 | Jackson, III |
| 2015/0366552 A1 | 12/2015 | Sasaki et al. |
| 2015/0374213 A1 | 12/2015 | Maurice, Jr. |
| 2016/0015467 A1 | 1/2016 | Vayser et al. |
| 2016/0030061 A1 | 2/2016 | Thommen et al. |
| 2016/0066965 A1 | 3/2016 | Chegini et al. |
| 2016/0067003 A1 | 3/2016 | Chegini et al. |
| 2016/0074029 A1 | 3/2016 | O'Connell et al. |
| 2016/0095505 A1 | 4/2016 | Johnson et al. |
| 2016/0106408 A1 | 4/2016 | Ponmudi et al. |
| 2016/0166135 A1 | 6/2016 | Fiset |
| 2016/0174814 A1 | 6/2016 | Igov |
| 2016/0213500 A1 | 7/2016 | Beger et al. |
| 2016/0228280 A1 | 8/2016 | Schuele et al. |
| 2016/0235284 A1 | 8/2016 | Yoshida et al. |
| 2016/0256036 A1 | 9/2016 | Gomez et al. |
| 2016/0287264 A1 | 10/2016 | Chegini et al. |
| 2016/0296220 A1 | 10/2016 | Mast et al. |
| 2016/0345952 A1 | 12/2016 | Kucharzyk et al. |
| 2016/0353978 A1 | 12/2016 | Miller et al. |
| 2017/0003493 A1 | 1/2017 | Zhao |
| 2017/0007226 A1 | 1/2017 | Fehling |

(56) References Cited

U.S. PATENT DOCUMENTS

| | | |
|---|---|---|
| 2017/0027606 A1 | 2/2017 | Cappelleri et al. |
| 2017/0042408 A1 | 2/2017 | Washburn et al. |
| 2017/0042411 A1 | 2/2017 | Kang et al. |
| 2017/0065269 A1 | 3/2017 | Thommen et al. |
| 2017/0065287 A1 | 3/2017 | Silva et al. |
| 2017/0086939 A1 | 3/2017 | Vayser et al. |
| 2017/0105770 A1 | 4/2017 | Woolley et al. |
| 2017/0135699 A1 | 5/2017 | Wolf |
| 2017/0156755 A1 | 6/2017 | Poll et al. |
| 2017/0156814 A1 | 6/2017 | Thommen et al. |
| 2017/0196549 A1 | 7/2017 | Piskun et al. |
| 2017/0224391 A1 | 8/2017 | Biester et al. |
| 2017/0245930 A1 | 8/2017 | Brannan et al. |
| 2017/0280969 A1 | 10/2017 | Levy et al. |
| 2017/0296038 A1 | 10/2017 | Gordon et al. |
| 2018/0008138 A1 | 1/2018 | Thommen et al. |
| 2018/0008253 A1 | 1/2018 | Thommen et al. |
| 2018/0014858 A1 | 1/2018 | Biester et al. |
| 2018/0098788 A1 | 4/2018 | White et al. |
| 2018/0098789 A1 | 4/2018 | White et al. |
| 2018/0110503 A1 | 4/2018 | Flock et al. |
| 2018/0110506 A1 | 4/2018 | Thommen et al. |
| 2018/0153592 A1 | 6/2018 | Larson |
| 2018/0214016 A1 | 8/2018 | Thommen et al. |
| 2018/0333061 A1 | 11/2018 | Pracyk et al. |
| 2019/0209154 A1 | 7/2019 | Richter et al. |
| 2019/0216454 A1 | 7/2019 | Thommen et al. |

FOREIGN PATENT DOCUMENTS

| | | |
|---|---|---|
| DE | 299 16 026 U1 | 11/1999 |
| EP | 0 537 116 A1 | 4/1993 |
| EP | 0 807 415 A2 | 11/1997 |
| GB | 2481727 A | 1/2012 |
| JP | 05-207962 A | 8/1993 |
| JP | 08-278456 A | 10/1996 |
| WO | 96/29014 A1 | 9/1996 |
| WO | 01/56490 A1 | 8/2001 |
| WO | 01/89371 A1 | 11/2001 |
| WO | 02/02016 A1 | 1/2002 |
| WO | 2004/103430 A2 | 12/2004 |
| WO | 2007/059068 A1 | 5/2007 |
| WO | 2008/121162 A1 | 10/2008 |
| WO | 2009/033207 A1 | 3/2009 |
| WO | 2010138083 A1 | 12/2010 |
| WO | 2013/033426 A2 | 3/2013 |
| WO | 2013/059640 A1 | 4/2013 |
| WO | 2014/050236 A1 | 4/2014 |
| WO | 2014/100761 A2 | 6/2014 |
| WO | 2014/185334 A1 | 11/2014 |
| WO | 2016/111373 A1 | 7/2016 |
| WO | 2016/131077 A1 | 8/2016 |
| WO | 2016/168673 A1 | 10/2016 |
| WO | 2016/201292 A1 | 12/2016 |
| WO | 2017/006684 A1 | 1/2017 |
| WO | 2017/015480 A1 | 1/2017 |
| WO | 2017/083648 A1 | 5/2017 |

OTHER PUBLICATIONS

International Search Report and Written Opinion for Application No. PCT/US2015/043554, dated Nov. 19, 2015 (8 pages).
International Search Report and Written Opinion for Application No. PCT/US2015/048485, dated Feb. 9, 2016. (16 pages).
International Search Report and Written Opinion for Application No. PCT/US2015/060978, dated Feb. 15, 2016 (8 pages).
Invitation to Pay Additional Fees for Application No. PCT/US2016/050022, dated Nov. 3, 2016 (2 pages).
International Search Report and Written Opinion for Application No. PCT/US2016/050022, dated Feb. 1, 2017 (19 pages).
International Preliminary Report on Patentability issued for Application No. PCT/US216/050022, dated Mar. 15, 2018.
Iprenburg, M, "Percutaneous Transforaminal Endoscopic Discectomy: The Thessys Method," in Lewandrowski, K., et al, Minimally Invasive Spinal Fusion Techniques, Summit Communications, 2008 pp. 65-81.
Jung, K., et al., "A hands-free region-of-interest selection interface for solo surgery with a wide-angle endoscope: preclinical proof of concept," Surg Endosc, 2017, v. 31, pp. 974-980.
Regan, J. M. et al., "Burr Hole Washout versus Craniotomy for Chronic Subdural Hematoma: Patient Outcome and Cost Analysis," Plos One, Jan. 22, 2015, DOI:10.1371/journal.pone.0115085.
Shalayev, S. G. et al, "Retrospective analysis and modifications of retractor systems for anterior odontoid screw fixation," Neurosurg Focus 16 (1):Article 14, 2004, pp. 1-4.
Extended European Search Report for Application No. 16843037.9; dated Mar. 14, 2019 (8 pages).
International Search Report for Application No. PCT/IB18/57367, dated Jan. 29, 2019, (4 pages).
International Search Report and Written Opinion for Application No. PCT/US18/21466 dated Jul. 3, 2018 (8 pages).
International Search Report and Written Opinion for Application No. PCT/US18/21454, dated Jul. 3, 2018 (16 pages).
International Search Report and Written Opinion for Application No. PCT/US18/21449, dated Aug. 27, 2018 (13 pages).
International Search Report and Written Opinion for Application No. PCT/US18/47136, dated Jan. 23, 2019 (9 pages).

* cited by examiner

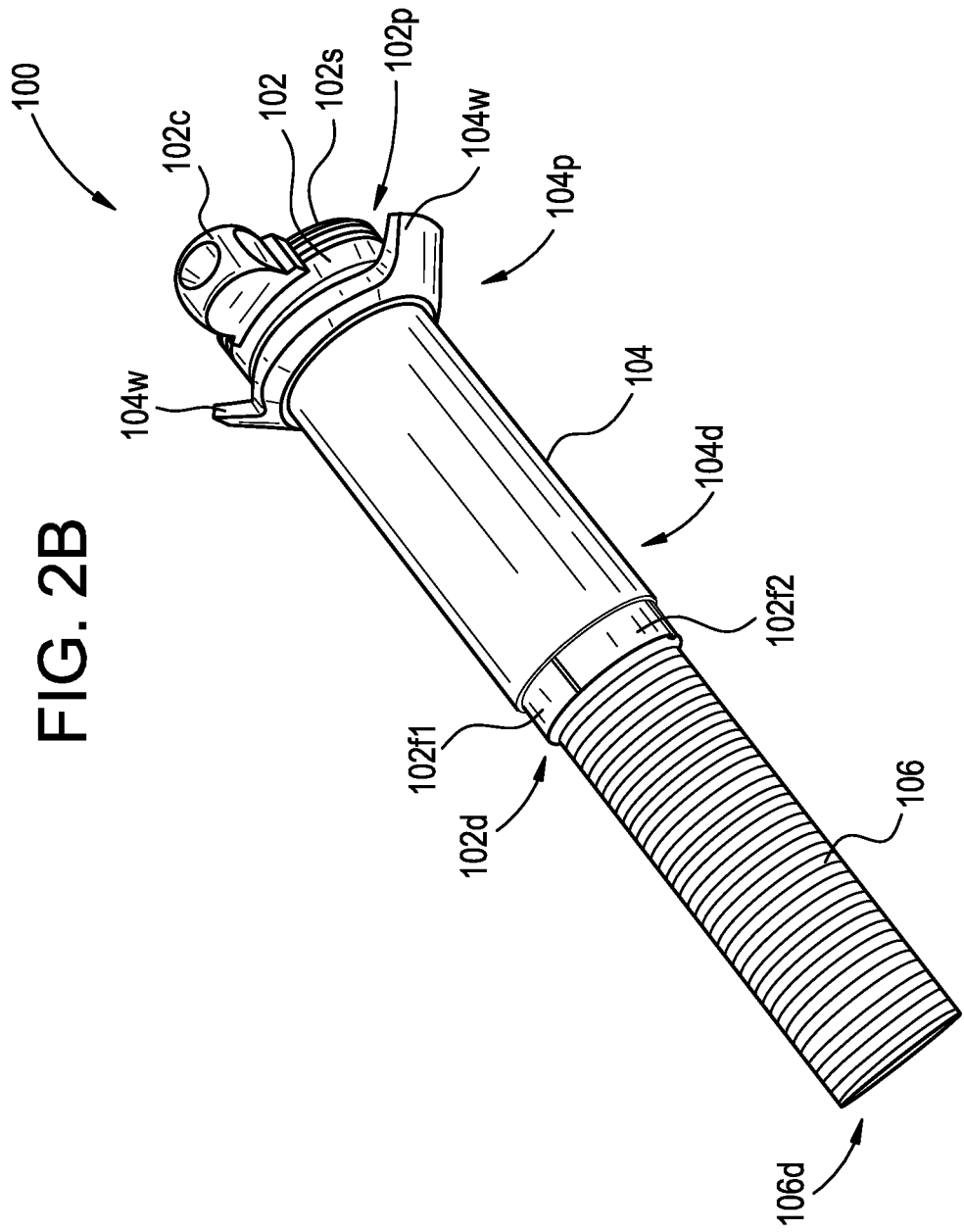

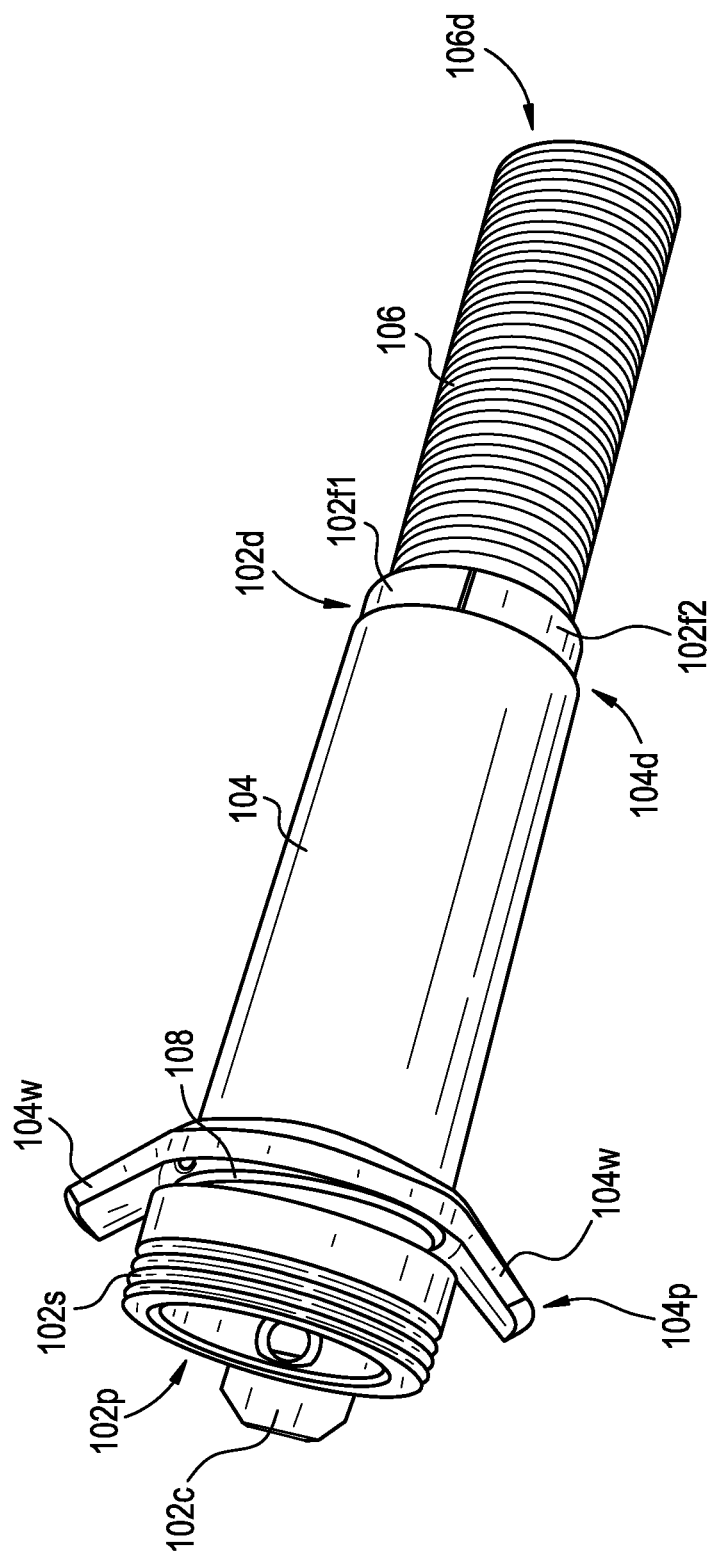

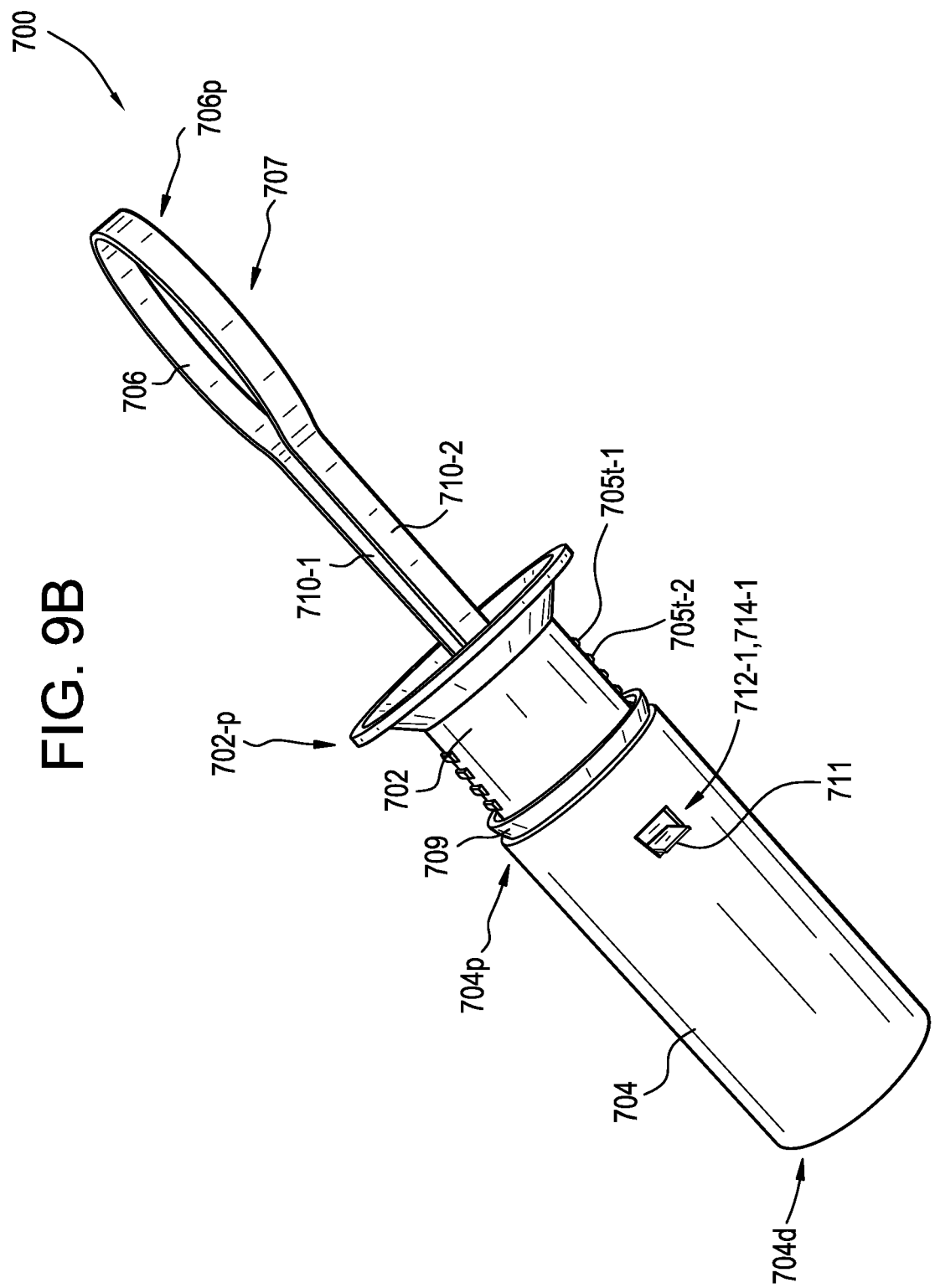

DEVICES AND METHODS FOR PROVIDING SURGICAL ACCESS

CROSS REFERENCE TO RELATED APPLICATION

The present application claims priority to U.S. Provisional Application No. 62/468,475 filed on Mar. 8, 2017, which is hereby incorporated by reference herein. The present application is also a continuation-in-part of U.S. application Ser. No. 15/437,792 filed on Feb. 21, 2017, which is a continuation-in-part of U.S. application Ser. No. 15/254,877 filed on Sep. 1, 2016, which claims priority to U.S. Provisional Application No. 62/214,297 filed on Sep. 4, 2015, each of which is hereby incorporated by reference herein.

FIELD

The present application relates to devices and methods for providing surgical access, e.g., using adjustable length surgical access devices.

BACKGROUND

Traditionally, incisions are made into a patient's body in order to access a patient's surgical region. Often, these incisions are made large enough to accommodate the insertion and removal of various implants, instruments and other objects. Such incisions provide unrestricted access through the patient's skin, and to the patient's anatomy at and around the surgical region. Such free access to and movement within the patient's body may provide certain advantages, but can increase the invasiveness of the procedure and can expose the patient to additional risks, for example, due to the various moving objects during surgery undesirably making contact with the patient, for example, at areas other than the surgical site.

To this end, access systems such as tubular access ports have been developed to provide enhanced targeting and accuracy to the patient's surgical region of interest. These ports can be used in minimally-invasive or percutaneous surgical procedures. For instance, microsurgical spinal bone resections and spinal decompressions, to name a few surgical procedures, are performed under microscopic view through openings in miniature percutaneous tubular access ports. Rather than inserting implants, instruments, objects, and even body parts (e.g., surgeon's hands) freely into the patient's body via the incision, the tubular access port is inserted through the incision and stabilized at or near the patient's surgical region, leaving a proximal end of the tubular access port accessible from above the patient's skin. Once inserted, the tubular access port provides a working channel from the patient's skin to the surgical site and protects and prevents trauma to, for example, bone, tissue, and nerves by objects being moved to and from the surgical site through the access port.

These tubular access ports are designed to have lengths capable of reaching the surgical region while being accessible from outside of the patient's skin or incision. Because the tubular access port is used for various surgeries, in order to access a number of surgical regions located at varying depths in the patient's body, traditional tubular access ports are manufactured in many sizes to achieve the desired surgical objective. Manufacturers of these access ports are thus tasked with developing and maintaining adequate supplies of a large variety of access tubes, each of which can have varying specifications (e.g., lengths). Adequate machinery and human supervision is required to oversee the manufacturing of a large and diverse portfolio of access ports. Likewise, traditional surgical centers such as hospitals are left with the burden of purchasing and storing a large and diverse inventory of access ports, in order to be prepared to use the adequate-length access port for any surgery at any given time.

SUMMARY

Adjustable-length surgical access devices are disclosed herein, which can advantageously allow an overall length of the access device to be quickly and easily changed by the user. The access devices herein can reduce or eliminate the need to maintain an inventory of many different length access devices. In some embodiments, the length of the access device can be adjusted while the access device is inserted into the patient. This can reduce or eliminate the need to swap in and out several different access devices before arriving at an optimal length access device. This can also reduce or eliminate the need to change the access device that is inserted into a patient as the depth at which a surgical step is performed changes over the course of a procedure. Rather, the length of the access device can be adjusted in situ and on-the-fly as needed or desired to accommodate different surgical depths.

In some embodiments, an access device can include an upper tube having an opening formed therethrough, the upper tube including: a proximal end configured to prevent proximal movement of a spring, the spring forming an opening through which the upper tube is disposed; and one or more fingers formed at a distal end of the upper tube and extending toward a proximal end of the upper tube, the one or more fingers having ribs formed on an inner surface thereof; a middle tube having an opening formed therethrough for slidably receiving the upper tube, the middle tube including a proximal end configured to apply force on the spring; and a lower tube slidably disposed at least in part within the distal end of the upper tube and having an opening formed therethrough, the lower tube including grooves disposed on at least a portion of an outer surface of the lower tube and configured to engage with the ribs on the inner surface of the one or more fingers of the upper tube; wherein the middle tube is biased away from the upper tube in a configuration in which the spring is uncompressed, causing the distal end of the middle tube to compress the one or more fingers of the upper tube and lock the position of the lower tube by engaging the ribs on the inner surface of the fingers with the grooves on the outer surface of the lower tube, restricting the proximal and distal movement of the lower tube relative to the upper tube, and wherein the access device is actuated by proximally moving the middle tube relative to the upper tube against the bias of the spring, causing the one or more fingers to become exposed and move away from the lower tube, and enabling proximal and distal movement of the lower tube relative to the upper tube.

The openings formed through one or more of the upper tube, the middle tube and the lower tube can be round, square or rectangular openings. One or more of the upper tube, middle tube and lower tube can have round, square or rectangular shapes formed by their outer surfaces. To prevent the proximal movement of the spring, the proximal end of the upper tube can include a stop portion having an outer surface with a circumference larger than a circumference of an adjacent portion of the upper tube. The stop portion can be configured to prevent proximal movement of the spring relative to the distal end of the upper tube, and to cause the spring to compress when force is applied thereto in a proximal direction by the proximal end of the middle tube. The middle tube can include one or more handles extending away from an outer surface of the proximal end of the middle tube. The proximal movement of the middle tube can be caused by the application of force, in a proximal direction, on the one or more handles. The one or more fingers can be defined by slits formed through the outer and inner surfaces of the upper tube at its distal end. The grooves on the inner surface of the fingers of the upper tube can be configured to mate with the grooves on the outer surface of the lower tube, to restrict the proximal and distal movement of the lower tube relative to the upper tube. The size of the opening of the upper tube at its distal end when the fingers of the upper tube are compressed can be smaller than or equal to the size of the lower tube at its proximal end. The size of the opening of the upper tube at its distal end when the fingers of upper tube are flanged can be larger than the size lower tube at its proximal end. The size of the opening of the middle tube can be: (i) larger than the size of the upper tube at its distal end; (ii) larger than the size of the lower tube; and (iii) smaller than the size of the spring. A length of the access device can be adjustably set by the locked position of the lower tube in which its proximal and distal movement relative to the upper tube is restricted by the engagement of the grooves on the inner surface of the fingers with the grooves on the outer surface of the lower tube.

In some embodiments, a method for operating an access device can include identifying a target depth required to access a surgical site in a patient's body; adjusting the length of a surgical access device based on the identified target depth; and advancing a distal end of the surgical access device toward the surgical site in the patient's body.

Adjusting of the length of the surgical access device can include advancing the surgical access device from a biased configuration to an actuated configuration, to allow distal and proximal sliding of a lower tube of the access device relative to an upper tube of the access device; sliding the lower tube to a target position relative to the upper tube; and advancing the surgical access device from the actuated configuration to the biased configuration, to lock the target position of the lower tube relative to the upper tube. The advancing of the surgical access device from the biased configuration to the actuated configuration can include causing one or more fingers disposed on the distal end of the lower tube to flange by applying one or more of (i) distal force on the upper tube, and (ii) proximal force on the middle tube, against the bias of a spring positioned between a proximal end of the upper tube and a proximal end of the middle tube, causing the middle tube to slide proximally toward the proximal end of the upper tube, wherein, in the actuated configuration, the flanged fingers have an opening configured to enable the lower tube to slide distally and proximally therein. The advancing of the surgical access device from the actuated configuration to the biased configuration can include releasing the distal force on the upper tube or the proximal force on the middle tube, causing the spring to bias to its uncompressed configuration and driving the middle tube distally away from the proximal end of the upper tube, such that the fingers of the upper tube are compressed by the inner surface of the middle tube, and causing grooves disposed on an inner surface of the fingers of the upper tube to mate with grooves disposed on an outer surface of the lower tube to prevent the distal and proximal movement of the lower tube relative to the upper tube.

The method can include delivering a material to the surgical site through an opening formed through the surgical access device, the material including one or more of: (i) a flowable material selected from the group consisting of hemostat and gelatin, and (ii) a powdered material selected from the group consisting of powdered pig bladder, pixie dust, and pixie power.

In some embodiments, a surgical access device can include an inner tube; and an outer tube having a distal end and a proximal end, and a hole formed therethrough, the hole being configured to receive the inner tube, wherein an external surface of the inner tube generates friction with the internal surface of the outer tube, and wherein movement of the inner tube distally and proximally relative to the outer tube is restricted by the friction generated by the external surface of the inner tube with the internal surface of the outer tube.

In some embodiments, an access device can include a tube having an opening formed therethrough from a distal end to a proximal end of the tube, the tube comprising one or more sets of cut regions along an external surface of the tube for separating the tube into a useable portion and a disposable portion, wherein the useable portion has a length configured to surgically access an area of a patient's body.

The sets of cut regions can include one or more perforations. The sets of cut regions can be provided at fixed intervals along a portion of the length of the tube. Each of the sets of cut regions can be provided around the circumference of the external surface of the tube. Each of the sets of cut regions can be provided around less than the entire circumference of the external surface of the tube. Each of the perforations can penetrate through the tube from the external surface to the internal surface.

The access device can include a ring portion comprising two or more concentric walls extending from a proximal end to a distal end of the ring portion, the two or more concentric walls being separated by a space configured to receive the proximal end of the tube. One of the two or more concentric walls can include one or more teeth features angled facing the proximal end of the ring portion. The one or more teeth can be configured to penetrate the external surface of the proximal end of the tube when the ring portion is in a mounted configuration. The ring portion can be placed in the mounted configuration by (i) sliding the tube between two of the two or more concentric walls, one of which includes the one or more teeth features, from the distal end of the ring portion toward the proximal end of the ring portion, and (ii) pulling the tube from the proximal end of the ring portion toward the distal end of the ring portion, causing the penetration of the one or more teeth into the external surface of the tube. The one of the two or more walls including the one or more teeth features can have the one or more teeth features disposed on a surface facing another of the two or more concentric walls. The two or more concentric walls can include an exterior wall, an interior wall and a middle wall provided between the exterior wall and the interior wall. The middle wall can be the one of the two or more concentric walls that includes the one or more teeth features. The one or more teeth features can be provided on an internal surface of the middle wall.

In some embodiments, a method of operating an access device can include identifying a target depth required to access a surgical site in a patient's body; adjusting the length of a surgical access device based on the identified target depth; and advancing a distal end of the surgical access device toward the surgical site in the patient's body.

The adjusting the length of the surgical device can include removing a disposable portion of a tube of the surgical access device, by separating the disposable portion from the rest of the tube. The separating of the disposable portion can include twisting, bending or applying force against opposite sides of the tube of the surgical access device relative to a fixed pivot point. The fixed pivot point can be located at one of a set of cut regions disposed on the external surface of the tube. The set of cut regions can include one or more perforations. Each of the sets of cut regions can be provided around the circumference of the external surface of the tube. Each of the perforations can penetrate through the tube from the external surface to the internal surface.

The method can include mounting a tube of the adjusted-length surgical device onto a ring portion. The mounting of the tube onto the ring portion can include sliding the proximal end of the tube in a distal end of the ring portion, toward a proximal end of the ring portion, the proximal end of the tube being slid between two walls of the ring portion; pulling the tube in a direction from the proximal end of the ring portion toward the distal end of the ring portion, wherein the pulling of the tube causes the teeth features disposed on a surface of a first wall among the two walls to grip the tube by penetrating into an external surface of the tube, the teeth features being disposed on the surface of the first wall facing a second wall among the two walls. The method can include stabilizing the surgical access device advanced into the surgical site of the patient's body by connecting a stabilizing feature of the ring portion to a corresponding stabilizing feature on an anchor device.

In some embodiments, a surgical access device can include an inner tube having an opening formed therethrough and a knob protruding from an external surface of the inner tube; and an outer tube having an opening formed therethrough and one or more slots connected by a path, the one or more slots and the path penetrating through an external and internal surface of the outer tube and being operable to receive the knob of the inner tube, wherein rotating the inner tube in a first direction relative to the outer tube causes the inner tube to be positioned in an adjustable-length configuration, in which the knob of the inner tube is slidably disposed along the path of the outer tube, and wherein rotating the inner tube in a second direction opposite the first direction relative to the outer tube causes the inner tube to be positioned in a fixed-length configuration, in which the knob of the inner tube is fixedly engaged within one of the one or more slots of the outer tube.

A proximal end of the inner tube can include a handle, the handle being operable to control the rotating of the inner tube in the first and second directions. The opening of the outer tube can be configured to receive a first surgical tool. The outer tube can include a sub-tube protruding from the external surface thereof, the sub-tube being configured to receive a second surgical tool. The inner tube in the adjustable-length configuration can be advanced distally and proximally such that the knob slides along the path of the outer tube. Fixing the knob of the inner tube in each of the slots of the outer tube can cause the length of the surgical access device to be altered.

In some embodiments, a method for operating a surgical access device can include identifying a target depth required to access a surgical site in a patient's body; adjusting the length of a surgical access device based on the identified target depth; and advancing a distal end of the surgical access device toward the surgical site in the patient's body.

The adjusting the length of the surgical access device can include rotating an inner tube of the surgical access device in first direction relative to an outer tube of the surgical access device, to position a knob protruding from an external surface of the inner tube within a path formed along the length of an outer tube, the inner tube being slidably engaged within the outer tube; advancing the inner tube distally or proximally relative to the outer tube, such that the knob of the inner tube slides along the path of the outer tube; rotating the inner tube in a second direction opposite the first direction relative to the outer tube, to position the knob of the inner tube within one of a plurality of slots formed along the length of the outer tube and extending from the path, wherein the positioning of the knob of the inner tube within one of the plurality of slots causes the proximal and distal position of the inner tube relative to the outer tube to be fixed.

In some embodiments, a surgical access device can include an inner tube including one or more engagement features of a first type disposed on an outer surface thereof; and an outer tube telescopically mated with the inner tube, and including one or more engagement features of a second type formed at least on the inner surface thereof; wherein the first type of engagement features and the second type of engagement features are complementary to each other, and wherein a length of the surgical access device is adjusted by one of: (i) rotating the inner tube relative to the outer tube such that the one or more engagement features of the inner tube slide along the corresponding one or more engagement features of the outer tube, and (ii) applying opposite proximal or distal forces on the inner tube and outer tube, thereby causing engagement features of the inner tube to slip from the corresponding one or more engagement features of the outer tube to adjacent others of the one or more engagement feature of the outer tube.

The one or more engagement features of the inner tube and the outer tube can form oblique angles relative to a longitudinal axis of the inner tube and/or the outer tube. The one or more engagement features of the inner tube and the outer tube can be formed of a deformable material enabling their slipping therebetween. The one or more engagement features of the inner tube and the outer tube can be formed around part or all of the circumference of the inner tube and the outer tube, respectively.

In some embodiments, a surgical access device can include an inner tube having a distal end, a proximal end, and an opening formed therethrough, the inner tube comprising one or more ratchet features disposed along part of a length of an exterior surface of the inner tube, the one or more ratchet features comprising one or more tooth features; and an outer tube having a distal end, a proximal end, and an opening formed therethrough, the opening at the proximal end of the outer tube being configured to receive the distal end of the inner tube, and the outer tube comprising a lip feature formed around the circumference of the proximal end of the outer tube, the lip feature being configured to engage with one or more of the tooth features of the one or more ratchet features of the inner tube, wherein a length of the surgical access device is adjusted by applying opposite proximal and distal forces on the inner and outer tubes causing the lip feature of the outer tube to slip over one or more of the tooth features of the one or more ratchet features of the inner tube.

Engaging the lip feature of the outer tube with one or more of the tooth features of the inner tube can cause the distal and proximal movement of the inner and outer tube, relative to each other, to be restricted. The proximal end of the inner tube can be cone-shaped and can flange proximally and externally relative to the rest of the of the inner tube. The external surface of the cone shaped portion of the inner tube can be configured to contact a surface of skin of a patient's body when the surgical access device is inserted in the patient's body. A circumference of the internal surface of the outer tube at the lip feature can be smaller than a circumference of the external surface of the inner tube at the one or more tooth features.

The access device can include an auxiliary tool comprising a handle portion formed at a proximal end thereof, two or more prongs, and two or more tabs formed at corresponding distal ends of the two or more prongs, and the two or more prongs biased apart from one another, wherein the inner tube comprises one or more slots formed along part of the length of the inner tube, through the external and internal surfaces of the inner tube, wherein the outer tube comprises one or more slots formed along part of the length of the outer tube, through the external and internal surface of the outer tube, the one or more slots of the outer tube being shorter than the one or more slots of the inner tube, and wherein the auxiliary tool is engaged with the inner and outer tubes by squeezing the two or more prongs against their bias, proximally and distally moving the auxiliary tool along the opening of the inner tube, and releasing the two or more prongs causing their tabs to extend through the one or more slots of the inner tube and the one or more slots of the outer tube. The length of the surgical access device can be adjusted by proximally pulling or distally pushing the auxiliary tool when the tabs are extending through the one or more slots, causing distal or proximal force to be applied on the one or more slots of the outer tube and the distal and proximal position of the outer tube relative to the inner tube to change as the tabs slide along the one or more slots of the inner tube. The proximal pulling or the distal pushing of the auxiliary tool can cause the lip feature of the outer tube to slip over one or more of the tooth features of the inner tube.

In some embodiments, a method for adjusting a length of a surgical access device can include applying opposite distal and proximal forces on an inner tube and an outer tube of the surgical access device, the inner tube being slidably disposed within an opening of the outer tube, wherein the applying of the opposite distal and proximal forces causes a lip feature on an internal surface of a proximal end of the outer tube to slip past one or more tooth features of one or more ratchet features formed on an external surface of the inner tube; and terminating the opposite distal and proximal forces on the inner tube and the outer tube when the lip feature of the outer tube is engaged with one or more of the tooth features at a position in which the length of the surgical access device is equal to a desired length.

In some embodiments, a method for adjusting a length of a surgical access device can include applying distal or proximal force on an auxiliary tool positioned within an opening formed through an inner tube, the auxiliary tool comprising two or more prongs and or two or more corresponding tabs extending outwardly from distal ends of the two or more prongs through two or more slots formed through the inner tube and two or more slots formed through the outer tube, the two or more slots formed through the outer tube being shorter than the two or more slots formed through the inner tube, wherein applying the distal or proximal force on the auxiliary tool causes the two or more tabs to push or pull, respectively, against distal or proximal edges of the slots, such that the outer tube slides distally or proximally relative to the inner tube as the two or more tabs move distally or proximally along the one or more slots of the inner tube.

The applying the distal or proximal force on the auxiliary tool can further cause a lip feature formed on an internal surface of a proximal end of the outer tube to skip over one or more tooth features of one or more ratchet features formed on an external surface of the inner tube. The distal and proximal movement of the outer tube relative to the inner tube can be restricted when the lip feature of the outer tube is engaged with one or more of the tooth features of the inner tube. The auxiliary tool can be positioned within the opening of the inner tube by: inwardly squeezing the two or more prongs against their bias, such that the distance between the two or more prongs is less than the diameter of the opening of the inner tube; distally or proximally moving the auxiliary tool within the opening of the inner tube; and releasing the two or more prongs such that their bias causes the two or more tabs of the two or more prongs to separate and extend through the two or more slots formed in the inner tube and the two or more slots formed in the outer tube.

In some embodiments, a surgical access device can include a tube-shaped body having an external surface and an internal surface, the internal surface forming an opening through the surgical access device from a distal end to a proximal end; a plurality of longitudinal slits formed through the body, extending distally from the proximal end; and a plurality of bendable arms formed longitudinally through the body of the surgical access device, extending distally from the proximal end, each of the plurality of bendable arms being defined by two of the plurality of slits, wherein the plurality of bendable arms are configured to be externally bent relative to a pivot point to adjust the length of the access device.

The access device can include a ring wrapped around the external surface of the body, wherein the plurality of bendable arms are bent over a proximal end of the ring. The access device can include a stabilization material for fixing the position of the plurality of bendable arms on skin of a patient, the stabilization material comprising one or more of sutures, adhesive or tape. At least one of the plurality of bendable arms can engage with one or more posts having a fixed position relative to the body of a patient, the posts restricting the rotation of the one of the plurality of bendable arms.

In some embodiments, a method for adjusting a length of a surgical access device can include inserting a distal end of a surgical access device into a body of a patient, the surgical access device having a tube-shaped body; sliding a support ring distally along the body of the surgical access device such that a proximal end of the support ring is positioned above the surface of the skin of the patient; and bending one or more bendable arms against the proximal end of the support ring such that external surfaces of the one or more bendable arms are placed in contact with the skin of the patient, wherein the one or more bendable arms are formed longitudinally along the body of the surgical access device, extending distally from the proximal end of the surgical access device, the one or more bendable arms being separated by slits penetrating through the body of the surgical access device.

The one or more bendable arms can be secured to skin using a stabilization object including one or more of an adhesive, tape and sutures. At least one of the one or more bendable arms can be positioned between two or more posts having a fixed position relative to the body of the patient, such that rotation of the at least one of the one or more bendable arms is prevented.

In some embodiments, a surgical access device can include an inner tube having a distal end and a proximal end, a hole formed therethrough from the distal end to the proximal end, and one or more first ribbed features wrapped around the circumference of at least part of an external surface of the inner tube; and an outer tube having a distal end and a proximal end, a hole formed therethrough from the distal end to the proximal end, and one or more second ribbed features wrapped around the circumference of at least part of an internal surface of the outer tube, the outer tube having the inner tube slidably engaged therein, wherein the one or more first ribbed features are configured to engage with the one or more second ribbed features, and wherein a length of the surgical access device is adjusted by applying opposite distal and proximal forces on the inner and outer tubes such that at least one of the one or more first ribbed features slips over at least one of the one or more second ribbed features.

The distal and proximal positions of the inner and outer tube, relative to each other, can be fixed when the one or more first ribbed features are engaged with the one or more second ribbed features. The one or more first ribbed features and the one or more second ribbed features can be convex or concave structures. The access device can include a collar feature operable to connect to a stabilization object having a fixed position relative to a body of a patient or an object.

In some embodiments, a method for adjusting the length of a surgical access device can include applying a force to a first tube of the surgical access device, the force being a distal or proximal force relative to a second tube of the surgical access device; causing one or more ribbed features of the first tube to slide past one or more ribbed features of the second tube; and releasing the force applied to the first tube when the first tube has reached a position, relative to the second tube, in which a length of the surgical access device is equal to a target length.

The first tube can be an inner tube having the one or more ribbed features formed on an external surface thereof. The second tube can be an outer tube having the one or more ribbed features formed on an internal surface thereof, the outer tube having the inner tube slidably engaged therein. The one or more ribbed features of the inner tube can be complimentary to the one or more ribbed features of the outer tube, such that distal and proximal movement of the inner and outer tubes relative to each other is prevented when the one or more ribbed features of the inner tube are engaged with the one or more ribbed features of the outer tube.

In some embodiments, a surgical access device can include a tube including a plurality of tube segments connected by interlocking snap features, the snap features including a protruding feature and a depression feature, wherein each of the plurality of tube segments includes at least one of a protruding feature and a depression feature, wherein at least one of the plurality of tube segment includes a protruding feature, and another of the plurality of tube segments adjacent to the one of the plurality of tube segments includes a depression feature, and wherein the one of the plurality of tube features and the adjacent tube feature are attached to one another by the protruding feature of the one tube segment being engaged with the depression feature of the adjacent tube segment.

One tube segment can be detachable from the adjacent tube segment by disengaging the protruding feature of the one tube segment from the depression feature of the adjacent tube segment. The protruding feature of the one tube segment can be disengaged from the depression feature of the adjacent tube segment by applying a force to the protruding feature in a direction away from the depression feature.

In some embodiments, a surgical access device can include a tube having a distal end and a proximal end, and corrugated features along a portion of a length of the tube, the corrugated features being configured to be pulled and pushed to extend and retract the length of the tube. The corrugated features can be provided adjacent to the proximal end of the tube.

In some embodiments, a surgical access device can include a first tube having a proximal end and a distal end, the first tube including fingers extending from the proximal end to the distal end; a second tube having a proximal end and a distal end, the second tube including fingers extending from the distal end to the proximal end, wherein the fingers of the first tube and the fingers of the second tube being are spaced part from each other, and wherein the fingers of the first tube are configured to engage with the fingers of the second tube to fix the position of the first tube relative to the second tube.

The size, shape and position of the fingers of the first tube can be equal to the size, shape and position of the fingers of the second tube. The fingers of the first tube can distally and proximally slide between the fingers of the second tube. The circumference of the first tube can be equal to the circumference of the second tube.

BRIEF DESCRIPTION OF DRAWINGS

This disclosure will be more fully understood from the following detailed description taken in conjunction with the accompanying drawings, in which:

FIG. 2B is a perspective view of the surgical access device of FIG. 1;

FIG. 2C is another perspective view of the surgical access device of FIG. 1;

FIG. 9B is a perspective view of the surgical access device of FIG. 9A;

DETAILED DESCRIPTION

Figure 1:
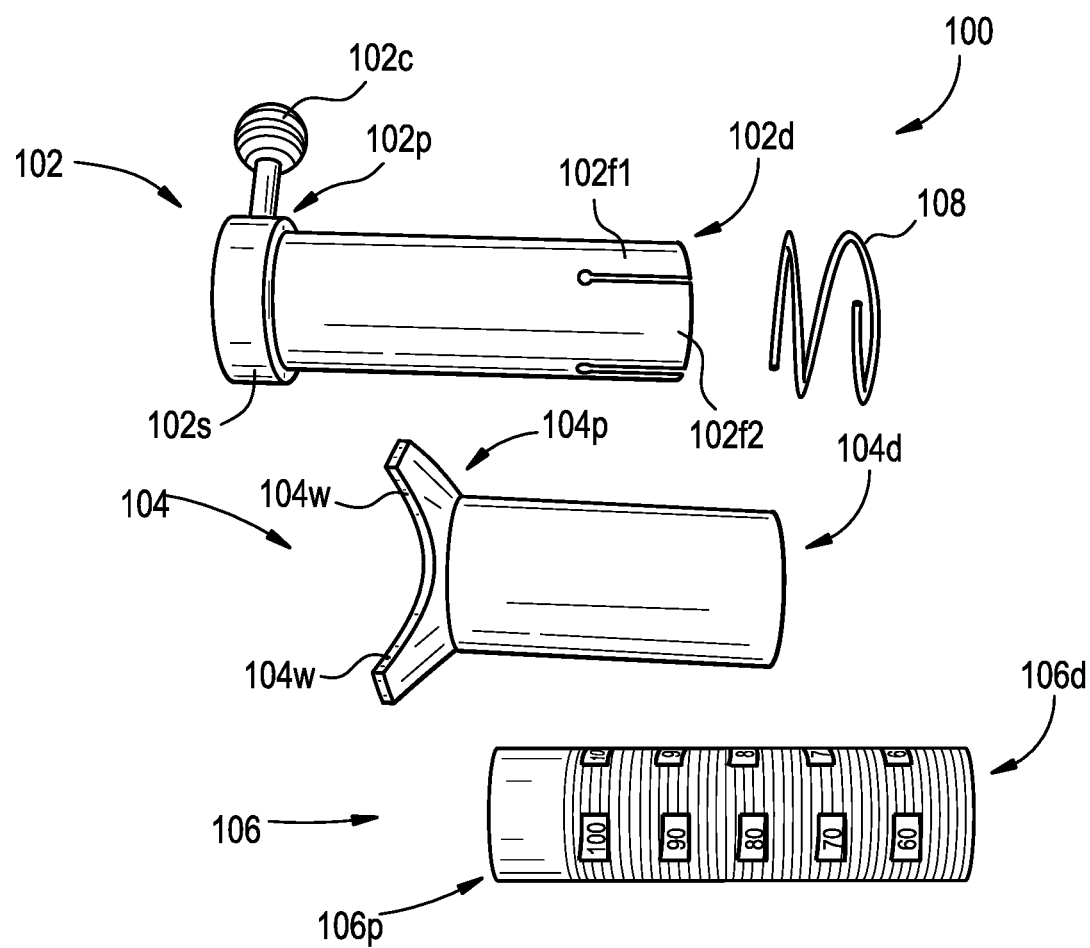
FIG. 1 is a side view of one exemplary embodiment of a surgical access device, shown in a disassembled state.
Figure 2A:
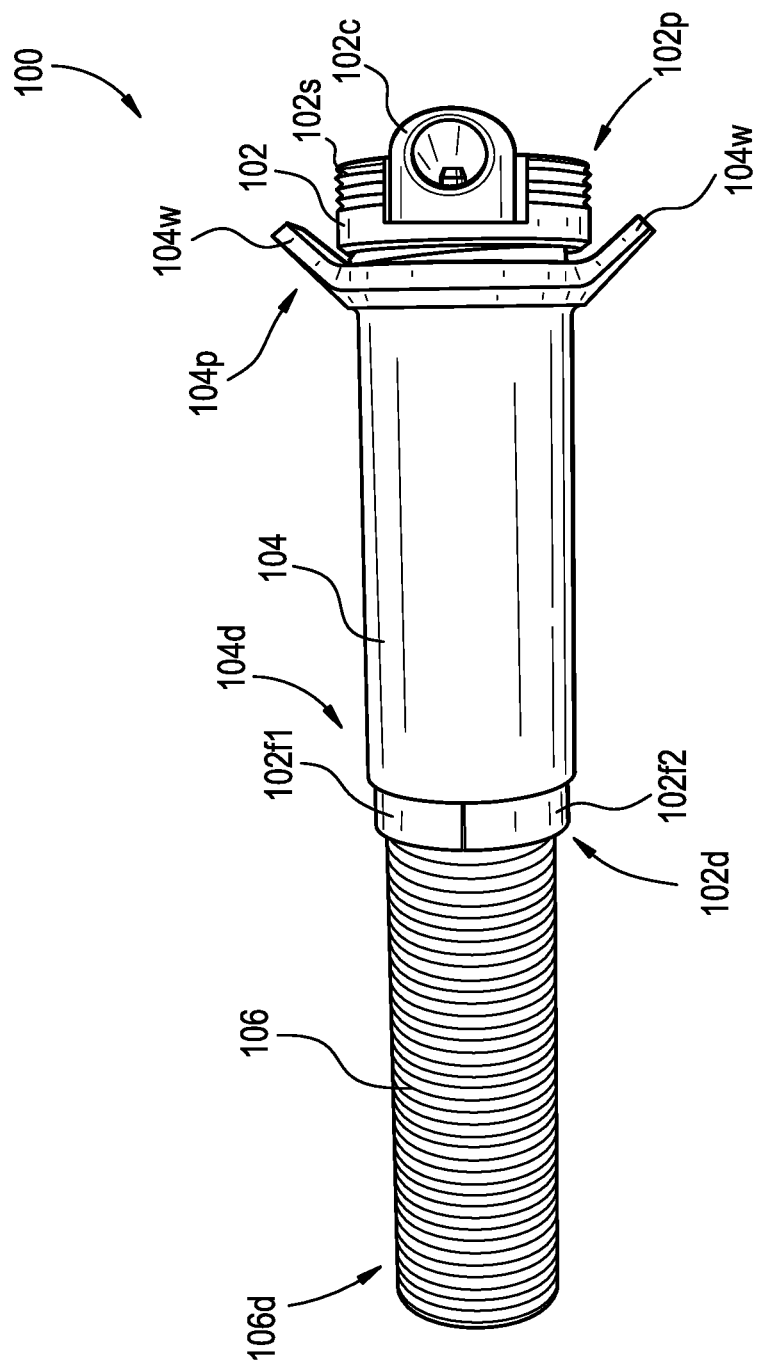
FIG. 2A is a side view of the surgical access device of FIG. 1, shown in an assembled state.

Adjustable-length surgical access devices are disclosed herein, which can advantageously allow an overall length of the access device to be quickly and easily changed by the user. The access devices herein can reduce or eliminate the need to maintain an inventory of many different length access devices. In some embodiments, the length of the access device can be adjusted while the access device is inserted into the patient. This can reduce or eliminate the need to swap in and out several different access devices before arriving at an optimal length access device. This can also reduce or eliminate the need to change the access device that is inserted into a patient as the depth at which a surgical step is performed changes over the course of a procedure. Rather, the length of the access device can be adjusted in situ and on-the-fly as needed or desired to accommodate different surgical depths.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments. The features illustrated or described in connection with one exemplary embodiment may be combined with the features of other embodiments. Such modifications and variations are intended to be included within the scope of the present disclosure. Further, to the extent features or steps are described as being, for example, "first" or "second," such numerical ordering is generally arbitrary, and thus such numbering can be interchangeable.

The present disclosure includes some illustrations and descriptions that include prototypes or bench models. A person skilled in the art will recognize how to rely upon the present disclosure to integrate the techniques, devices, and methods provided for into a product, such as a consumer ready, warehouse-ready, or operating room ready surgical device.

A person skilled in the art will appreciate that the present disclosure has application in conventional endoscopic, minimally-invasive, and open surgical procedures.

Exemplary embodiments of the present disclosure provide surgical access devices, and more specifically, adjustable-length surgical access devices. The surgical access device can include one or more tubes or portions that can be manipulated to obtain a surgical access device of a desired length that is optimal or desirable to access a patient's surgical site of interest. Examples of such manipulations can include pulling, pushing, twisting, rotating, pivoting, folding, sliding, and/or combinations thereof. Engagement features provided on the surgical access device, including, for example, on inner and outer surfaces thereof, can prevent, limit or restrict the lengthening and shortening of the surgical access device in certain circumstances, such as when the manipulations described above are performed with minimal or incidental force, e.g., below an identified force threshold. Such features can include grooves, threads, slots, protrusions, depressions, lips, and the like. Thus, the features can limit or prevent inadvertent lengthening and shortening of the surgical access device once the surgical access device has been configured to its desired length. The surgical access device can be or can include an enclosed tubular structure, a slotted or bladed retractor, a cannula, and so forth.

The surgical access device can include a proximal end, proximate to a user of the surgical access device, and a distal end, proximate to the patient or the patient's surgical region. Formed through the surgical access device can be a hole or opening, extending from the proximal end to the distal end, defining a working channel through which implants, instruments, or other objects can be inserted to or removed from the patient's body.

The surgical access device can include a body, which can refer to the structure that makes up the external and internal surfaces of the surgical access device. The internal surface of the body can define the working channel through the surgical access device. The surgical access device can be round, square, rectangular, or any other shape, as deemed necessary or desirable to access a patient's surgical region. Likewise, the working channel formed through the surgical access device can be round, square, rectangular or any other shape, as deemed necessary or desirable to enable the insertion and removal of implants, instruments, or other objects for surgery.

The thickness of the body of the surgical access device, and other of its dimensions (e.g., diameter, inner circumference, outer circumference) can vary, so long as the aspects described herein enabling length adjustment are retained.

First Embodiment

FIGS. 1, 2A to 2C, and 3A to 3D illustrate one exemplary embodiment of a surgical access device 100 configured to provide operative access to a patient's anatomy. Although the surgical access device 100 may be described with reference to its use to access a patient's intervertebral disc during spinal surgery, it should be understood that the surgical access device 100 can be configured and used in accordance with other surgical procedures to access to other surgical regions within a patient.

As shown, the surgical access device 100 can include an upper tube 102, a middle tube 104, a lower tube 106, and a spring 108. FIG. 1 illustrates the disassembled parts or components of the access device 100, namely the upper tube 102, middle tube 104, lower tube 106, and spring 108. In some embodiments, the access device 100 is referred to as a "telescoping tube," due to its being configured so that the upper, middle and lower tubes 102, 104, and 106 fit within one another in a way that allows them to slidably engage to enable the length of the access tube 100 to be extended and retracted.

The upper tube 102, middle tube 104, and lower tube 106 can be referred to as a first inner tube, outer tube, and second inner tube, respectively, to describe their inner and outer positions in the assembled surgical access device 100.

Still with reference to the disassembled access device 100 shown in FIG. 1, the upper tube 102, the middle tube 104, the lower tube 106, and the spring 108 can each include at least a portion that is substantially tubular or cylindrical. The upper tube 102, the middle tube 104, the lower tube 106, and the spring 108 can be assembled into a length-adjustable surgical access device 100 that can be used to access the patient's anatomy during surgery. To assemble the surgical access device 100, the distal end 102d of the upper tube 102 can be inserted through the spring 108. The distal end 102d of the upper tube 102, once inserted through the spring 108, can be inserted into the proximal end 104p of the middle tube 104. The proximal end 106p of the lower tube 106 can be inserted into or within the distal end 102d of the upper tube 102. In use, the middle tube 104 can be axially translated in a proximal direction relative to the upper tube 102, against the bias of the spring 108. With the middle tube 104 translated proximally, one or more resilient fingers 102f formed at the distal end of the upper tube 102 can expand radially-outward to disengage from the lower tube 106, thereby allowing the lower tube 106 to translate axially relative to the upper tube 102 to set an overall length of the access device 100. When set to the desired length, the middle tube 104 can be released, such that it returns distally under the bias of the spring 108. As the middle tube 104 moves distally, it can urge the fingers 102f radially-inward into engagement with the lower tube 106 to fix the length of the access device 100.

The upper tube 102 can include a proximal end 102p. The proximal end 102p can include or can have formed thereon a stop 102s configured to abut the proximal end 104p of the middle tube 104, to stop or prevent the middle tube 104 from excessive proximal movement relative to the upper tube 102. The stop 102s can extend radially about the proximal end 102p of the upper tube 102. In other words, to prevent excessive proximal movement of the middle tube 104, the outer surface of the stop 102s can have a circumference that is larger than (1) the circumference of the outer surface of the adjacent proximal end 102p of the upper tube 102, and (2) the circumference of the inner surface of the proximal end 104p of the middle tube 104. The outer surface of the stop 102s can be textured with grooves and/or ridges to enhance its gripping qualities, thereby allowing the access device 100 to be more easily manipulated by a user, for example, to stabilize or twist the access device 100.

The stop 102s can include a connector interface 102c which can allow the position and/or orientation of the access device 100 to be fixed via a connector or other support (not illustrated). The connector interface 102c can be built in to or can protrude outwardly from the stop 102s. A connector can be used to connect the connector interface 102c of the access device 100 to an ipsilateral or contralateral pedicle anchor or anatomical support, operating table, or other support or stabilizing feature (not illustrated). The connector interface 102c can be used as a stabilizer portion during actuation of the access device 100.

The stop 102s and/or the connector interface 102c can be formed integrally with the upper tube 102p, or can be manufactured as a separate component that is attachable to the upper tube 102p.

The upper tube 102 can include a distal end 102d. The distal end 102d can have formed thereon flexible fingers 102f1 and 102f2 (collectively "102f") configured to engage with the lower tube 106 and limit or prevent the distal or proximal movement of the lower tube 106 relative to the upper tube 102. The flexible fingers 102f can be formed by slits (or cuts) formed in the body of the upper tube 102, starting from the distal end 102d toward the proximal end 102p. The proximal end of the slits can include a circle or hole of larger diameter than the slits, to enable the fingers to more easily, and/or more widely, expand or deflect as explained below. The flexible fingers 102f can include any number of fingers and can be created by one or more slits.

The length of the slits on the body of the upper tube 102 can be the same or can vary. The length of the slits forming the fingers 102f can be determined based on the length of the middle tube 104 and/or the lower tube 106, on the amount of engagement that is desired between the upper tube 102 and the lower tube 106, and/or on the amount of deflection or expansion of the fingers 102f that is desired or to be allowed. The length of the slits forming the fingers 102f can be equal to or greater than the difference in length between the upper tube 102 and the middle tube 104. The length of the slits forming the fingers 102f can be equal to or greater than the length of the outer surface of the upper tube 102 at the distal end 102d that is exposed when the middle tube 104 is fully retracted. The length of the slits can be in the range of 1% to 33% of the length of the upper tube 102 (e.g., 1%, 5%, 10%, 15%, 20%, 25%, 30%, 33%).

The inner surface of the upper tube 102 can include grooves or ridges that are congruent with, complementary to, or that mate with counterpart grooves or ridges on the outer surface of the lower tube 106. The ridges or grooves can be spiral, circular or otherwise shaped to engage with counterpart features to limit or prevent movement of the upper and lower tubes 102 and 106, relative to one another, in a lengthwise, proximal and distal direction. The grooves or ridges on the inner surface of the upper tube 102 can be formed on the distal end 102d, e.g., on the fingers 102f. The grooves and/or ridges can be referred to as complementary engagement features.

As explained in further detail below with reference to FIGS. 3A to 3D, the fingers 102f can be actuated (e.g., expand, deflect, flare) by proximally retracting the middle tube 104 relative to the upper tube 102, allowing the fingers 102*f* to expand or flare outward in the direction A illustrated in FIGS. 3B and 3C, thereby increasing or enlarging the diameter of the opening of the upper tube 102 at the distal end 102*d* where the fingers 102*f* are formed. When the fingers are in an expanded state (e.g., flared), as opposed to their default or rest state (e.g., contracted), the increased diameter of the distal end 102*d* can allow the lower tube 106 to slide or be moved distally and proximally relative to the upper tube 102. A desired total length of the access device 100 can be set by releasing the middle tube 104 from its retracted position, causing the middle tube 104 to move distally relative to the upper tube 102 as a result of the bias of the spring 108, and causing the fingers 102*f* to retract (e.g., opposite of direction A) and the diameter of the opening of the distal end 102*d* to decrease.

As mentioned above and described in further detail below, when the fingers 102*f* are flexed inward from their default position, the grooves on the inner surface of the upper tube 102 can engage with grooves in the outer surface of the lower tube 106. The lower tube 106 can include a distal end 106*d* and a proximal end 106*p*. The diameter of the opening of the tube 106 formed by the inner surface can be the same at the distal end 106*d* and at the proximal end 106*p*. The external surface of the lower tube 106 can include or have formed thereon grooves (or ridges) that are configured to engage with matching, mating, or complementary grooves on the internal surface of the upper tube 102. The grooves on the lower tube 106 can be provided at various regions along the length of the tube, as needed to achieve the desired length and stability characteristics of the access device 100 for its use in surgery.

The outer surface of the lower tube 106 can have markings, writing and/or other indications thereon. Markings provided along the length of the outer surface of the lower tube 106 can indicate lengths or other measurements (e.g., of the access device 100, of the lower tube 106, etc.) when the upper tube 102 is fixedly engaged with the lower tube 106. For example, the length of the access device 100 can be the measurement marked on the external surface of the lower tube 106 at the position where the distal end 102*d* of the upper tube 102 extends to.

As mentioned above and described in further detail below, to fix the position of the lower tube 106 relative to the upper tube 102 along a distal and proximal direction, and/or to fix the length of the access device 100, the middle tube 104 can be operated by proximal retraction and distal extension movements. The middle tube 104 can include a proximal end 104*p* and a distal end 104*d*.

The proximal end 104*p* of the middle tube 104 can include or can have formed thereon wings 104*w* (or rings, handles, ears, or another similar structure) that allow a user of the access device 100 to retract, pull or otherwise move or slide the middle tube 104 toward the proximal end 102*p* of the upper tube 102. The wings 104*w* can protrude or can be formed away from the external surface of the middle tube 104. The wings 104*w* or a portion thereof can extend away from the external surface of the middle tube 104 such that the wings 104*w* form a right angle or an oblique angle with the outer surface of the middle tube 104. The wings 104*w* can form a curve away from the external surface of the middle tube 104, such that the distal-most end of the wings 104*w* are formed away from the distal end 104*d* of the middle tube 104.

The dimensions, shape and other attributes of the wings 104*w* can vary as needed to provide an area where the user's fingers (e.g., middle and pointer fingers) can engage and pull the middle tube 104 toward the proximal end 102*p* of the upper tube 102. For instance, the curvature and length of the wings 104*w* can be determined and/or configured according to the average or maximum size of a human's index and/or middle fingers. Likewise, other configurations of the wings 104*w*, such as rings, can be rings that are formed external to or protruding from the outer surface of the middle tube 104 and that have an opening with a circumference larger than the average or maximum size of a human's index and/or middle fingers. It should be understood that the access device 100 can include one or more wings 104*w*.

As described in further detail below, when the middle tube 104 is retracted or pulled toward the proximal end 102*p* of the upper tube 102, the spring 108 that is disposed between the middle tube 104 and the upper tube 102 can be compressed. The size (compressed and uncompressed) and amount of force needed to compress the spring 108 can be determined based on various factors including the typical user's preference, the amount of time and speed at which the spring decompresses from the compressed state, the length of the tubes 102, 104, and 106, the material of the spring 108, and/or the thickness of the spring 108. The length of the spring 108 or the amount of lengthwise space that the uncompressed spring 108 covers when engaged with the upper tube 102 can be less than or equal to the difference in the length of the upper tube 102 and the middle tube 104. The spring 108 can be configured such that the amount of force needed to compress the spring 108 is (1) high enough so that the spring 108 returns towards a resting state to drive the middle tube 104 distally relative to the proximal end 102*p* of the upper tube 102 and maintain the set length of the access device 100; and (2) low enough so that the driving of the middle tube 104 distally relative to the proximal end 102*p* of the upper tube 102 is slow and controlled enough to not significantly alter the position of the access device 100 (e.g., relative to a patient) or the position of the tubes 102, 104, and 106 relative to one another.

As described above, the access device 100 can provide access to a patient's anatomy during surgery. Accordingly, the length of the access device 100 at its longest configuration can be large enough to reach an anatomical point of interest. To this end, each of the tubes 102, 104, and 106 can have a respective length such that, when the tubes 102, 104, and 106 are assembled together with the spring 108 to form the access device 100, the desired total length of the access device 100 can be achieved. The length of the upper tube 102 can be greater than the length of the middle tube 104 and the lower tube 106. The length of the middle tube 104 can be less than the length of the upper tube 102 and the lower tube 106. The length of the lower tube 106 can be greater than the length of the middle tube 104, and less than, equal to or greater than the length of the upper tube 102. The length of the lower tube 106 and/or the length of the grooved portion of the outer surface of the lower tube 106 can be equal to or greater than the distance from a patient's skin (e.g., where an incision is made and the access device 100 inserted) to the part or area of the patient's anatomy to which access is required, such that when the lower tube 106 is the only one of the tubes 102, 104, and 106 that is inserted into the incision, the lower tube 106 can reach and access that part or area of the patient's anatomy.

The openings or working channel created by the inner surfaces of the tubes 102, 104, and 106 can be large enough to enable objects (e.g., implants, instruments, or other objects) to be moved therethrough, to and from the distal end 100*d* and the proximal end 100*p* of the access device 100. The diameter and/or circumference of the opening of each of the tubes 102, 104, and/or 106 can vary from their distal ends to their proximal ends For example, the upper tube 102 can be configured such that the diameter or circumference of the opening at the proximal end 102p is larger than the diameter or circumference, respectively, of the opening at the distal end 102d. The openings of the tubes 102, 104, and/or 106 can gradually narrow or expand along their lengths.

The circumference of the opening of the middle tube 104 (at the proximal end 104p and the distal end 104d) can be larger than the circumference of the outer surface of the upper tube 102 (at the distal end 102d and the proximal end 102p), such that the distal end 102d of the upper tube 102 can be inserted through the opening at the proximal end 104p of the middle tube 104 and through the entirety of the length of the middle tube 104, exiting at the distal end 104d. The circumference of the opening of the middle tube 104 can be larger than the circumference of the outer surface of the lower tube 106. The circumference of the opening of the upper tube 102 at the distal end 102d and/or along the length of the fingers 102f, when the fingers 102f are in a radially-inward position, can be equal to or smaller than the circumference of the outer surface of the lower tube 106; and the circumference of the opening of the upper tube 102 at the distal end 102d and/or along at least a portion of the length of the fingers 102f, when the fingers 102f are at an expanded or radially-outward position, can be larger than the circumference of the outer surface of the lower tube 106. The circumference of the opening of the spring 108 can be larger than the circumference of the outer surface of the upper tube 102.

As described above, the tubes 102, 104, and 106, and the spring 108 can be assembled to form the access device 100. FIGS. 3A to 3D illustrate a process for using and/or adjusting the length of the access device 100 according to an exemplary embodiment. As will be described, the access device 100 can be actuated by (1) retracting the middle tube 104 relative to the upper tube 102, similar to a syringe; (2) adjusting the exposed length of the lower tube 106; and (3) releasing the middle tube 104.

Figure 3A:
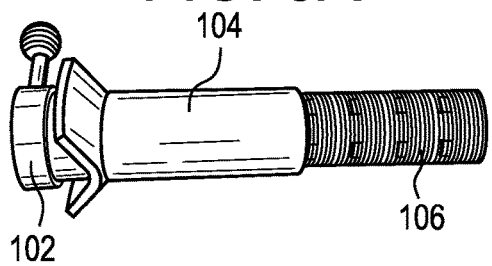
FIG. 3A is side view of the surgical access device of FIG. 1 in a locked position.

More specifically, FIG. 3A illustrates the access device 100 in a default or locked state in which the length of the access device is fixed. When the access device 100 is in its default state, the spring 108 (not shown in FIG. 3A) can urge the middle tube 104 distally relative to the upper tube 102. That is, the proximal end 104p of the middle tube 104 can be forced to its furthest position from the proximal end 102p of the upper tube 102 by the bias of the spring 108. In this position, the internal surface of the middle tube 104 can maintain the fingers 102f of the upper tube 102 in a radially-inward position in which they engage with the grooves or other engagement features of the lower tube 106. In such a position of the middle tube 104, a small part (e.g., 1%, 2%, 5%, 10%, 15%) of the fingers 102f can be exposed so long as the fingers 102f are not free to expand out of engagement with the lower tube 106.

Figure 3B:
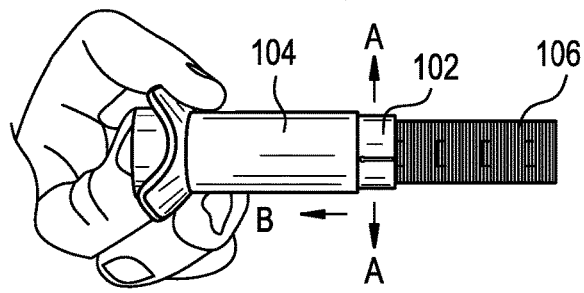
FIG. 3B is side view of the surgical access device of FIG. 1 in an unlocked position.

The access device 100 can be actuated by pulling, retracting or otherwise proximally moving or sliding, relative to the upper tube 102, in the direction B, the middle tube 104 toward the proximal end 102p of the upper tube 102, as shown in FIG. 3B. The actuation of the access device 100 can be performed by applying a pushing pressure or force on the proximal end 102p (or stop 102s) of the upper tube 102 (e.g., by a user's thumb), and applying an opposite pulling pressure or force on the wings 104w of the middle tube 104 (e.g., by the user's index and middle finger), against the bias of the spring 108.

Figure 3C:
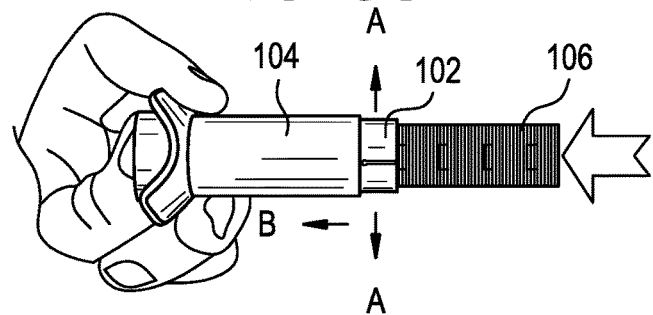
FIG. 3C is side view of the surgical access device of FIG. 1, schematically illustrating a length adjustment of the access device.

When the middle tube 104 is in the retracted position, as shown in FIGS. 3B and 3C, the distal end 104d of the middle tube 104 is moved toward the proximal end 102p of the upper tube 102. Because the upper tube 102 is longer than the middle tube 104, such a proximal retraction of the middle tube 104 can cause the fingers 102f of the upper tube 102 to become exposed. When the fingers 102f are exposed and no longer compressed by the inner surface of the middle tube 104, the fingers 102f can be free to expand in the direction A. The flaring or expanding of the fingers 102f can cause the diameter of the opening at the distal end of the upper tube 102 and/or the circumference of the inner surface of the upper tube at the fingers 102f to increase in size (e.g., to a size larger than the diameter or circumference of the lower tube 106). This can cause the fingers 102f and the lower tube 106 to no longer be engaged or fixedly positioned, thereby allowing the lower tube 106 to be slid or translated proximally or distally relative to the distal end 102d of the upper tube 102, as shown in FIG. 3C.

Figure 3D:
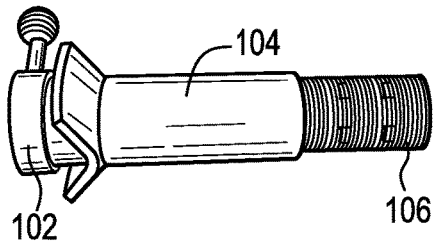
FIG. 3D is side view of the surgical access device of FIG. 1 in a locked position.

The lower tube 106 can continue to be moved proximally and distally so long as the access device 100 is actuated (e.g., the middle tube 104 remains in the retracted position). When the lower tube 106 is moved to its desired location such that the access device 100 has a resulting optimal or desired length for surgical use, the proximal or pulling force on the middle tube 104 and/or the distal or pushing force on the upper tube 102 can be released, causing the upper tube 102 and the middle tube 104 to return towards their default positions, and the fingers 102f to be compressed by the internal surface of the middle tube 104, such that the position of the lower tube 106 relative to the upper tube 102 becomes fixed. In other words, as shown in FIG. 3D, when the force on the upper tube 102 and/or the middle tube 104 is released, the spring 108 can expand, causing the middle tube 104 to move distally, away from the proximal end 102p of the upper tube 102. In addition, the previously exposed fingers 102f can become unexposed by sliding within the inner surface of the distal end 104d of the middle tube 104. As a result, the fingers 102f can compress, causing the ridges or grooves on the inner surface of the fingers 102f to engage with the ridges or grooves on the outer surface of the lower tube 106, thereby locking or preventing the distal or proximal movement of the lower tube 106 relative to the upper tube 102. The resulting access device 100 can have a length that is determined based on the selected amount of exposed area of the lower tube 106, as set by the position where the lower tube 106 is locked. The access device 100 can then be used to access a target or desired area of the patient's anatomy located at a distance that is reachable by the access device 100 having been set at a desired length.

Second Embodiment

Figure 4:
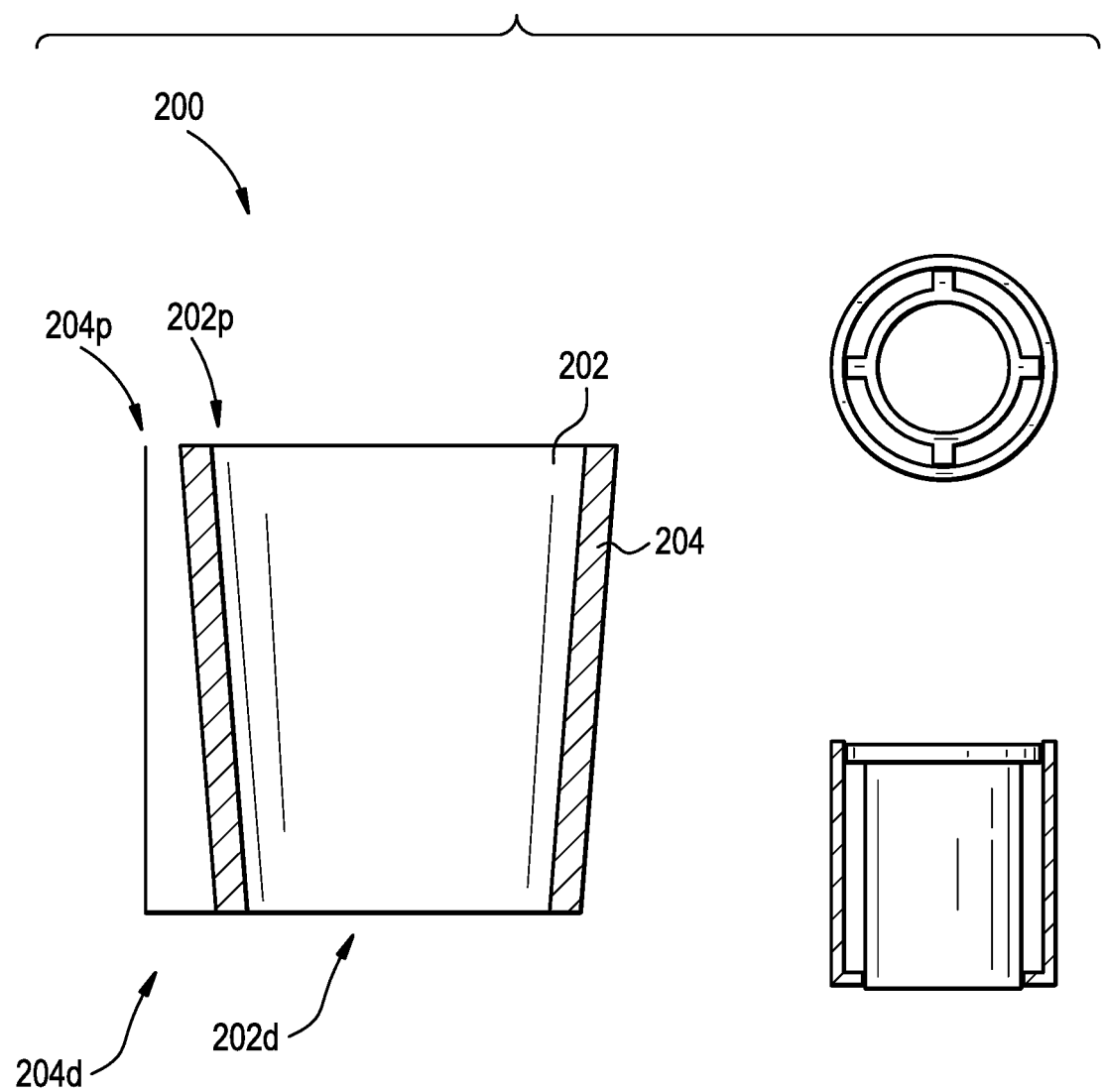
FIG. 4 is a sectional side view of another exemplary embodiment of a surgical access device.

FIG. 4 illustrates another exemplary embodiment of a surgical access device 200. The surgical access device 200 can include an inner tube 202 and an outer tube 204. The inner tube and the outer tube can have respective proximal ends (202p, 204p) and distal ends (202d, 204d), and holes or openings formed therethrough from their distal ends to the proximal ends to define a working channel through the access device.

The inner tube 202 can be slidably disposed within the outer tube 204—e.g., within the opening of the outer tube 204 to define a telescoping access device. The inner tube 202 and the outer tube 204 can be configured such that sufficient friction is created between the external surface of the inner tube 202 and the internal surface of the outer tube 204 to maintain a relative longitudinal position of the inner and outer tubes. To accomplish the desired friction between the tubes 202 and 204, the inner tube 202 can have an external surface with a circumference equal to or substantially equal to the circumference of the opening or internal surface of the outer tube 204.

To adjust the length of the surgical access device 200, opposite pulling and pushing forces can be applied to the tubes 202 and 204 to overcome the frictional force and axially translate the tubes relative to one another to shorten or lengthen the access device. When the pulling and pushing force is ceased, the friction between the tubes 202 and 204 can be effective to restrict the proximal and distal movement of the tubes 202 and 204 and to maintain the device 200 at the adjusted length. The inner and outer tubes 202, 204 can be rotationally fixed relative to one another, e.g., such that they inner and outer tubes cannot rotated with respect to one another about a central longitudinal axis of the device 200. The tubes 202, 204 can be rotationally fixed in various ways, such as by engagement between counterpart longitudinal rails and grooves, a pin-in-slot arrangement, or the like.

Third Embodiment

Figure 5:
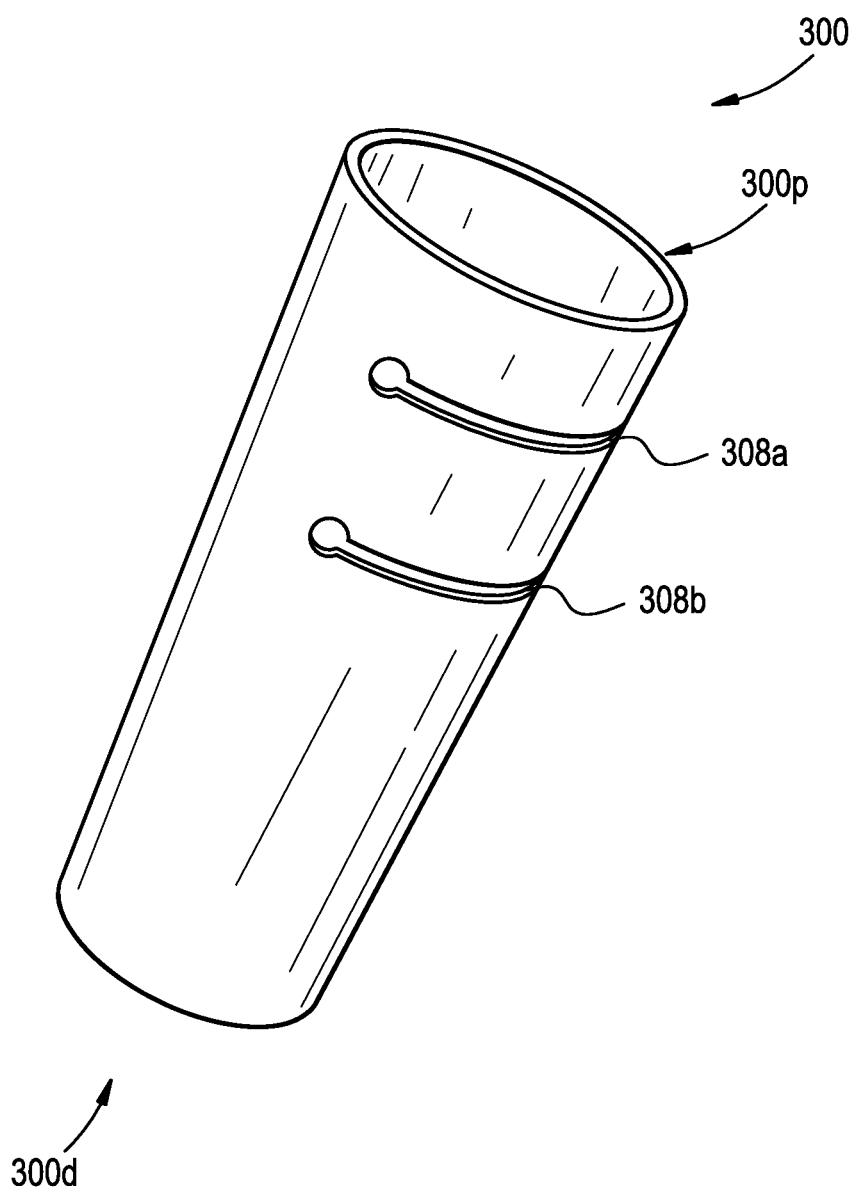
FIG. 5 is a perspective view of another exemplary embodiment of a surgical access device.
Figure 6A:
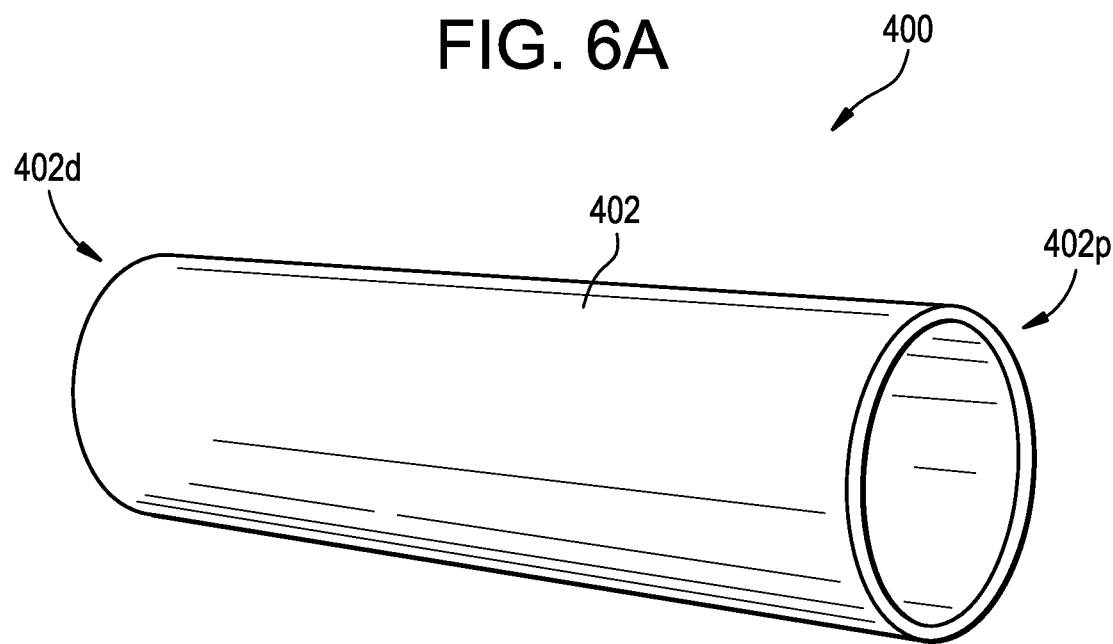
FIG. 6A is a perspective view of an exemplary tube of another exemplary embodiment of a surgical access device.
Figure 6B:
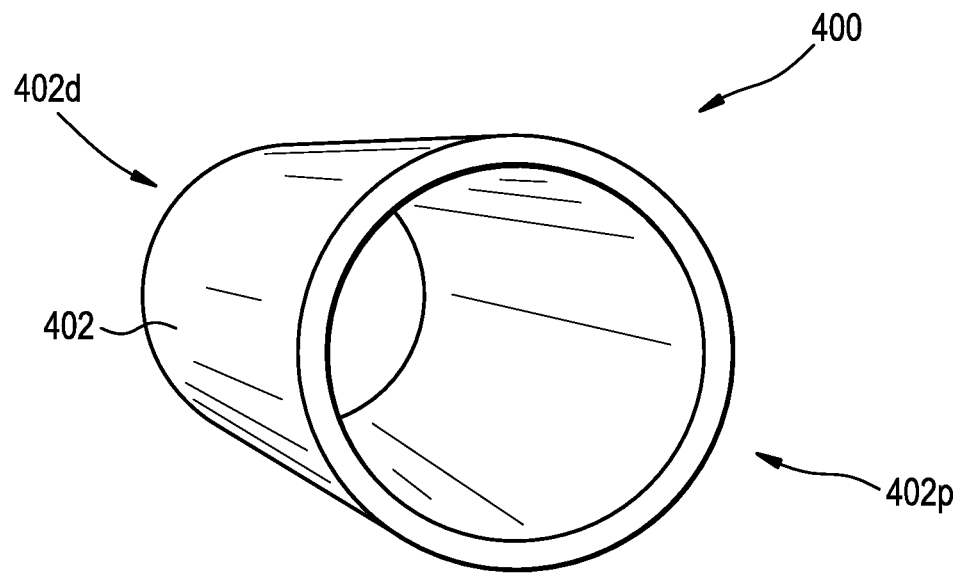
FIG. 6B is another perspective view the tube of FIG. 6A.
Figure 6C:
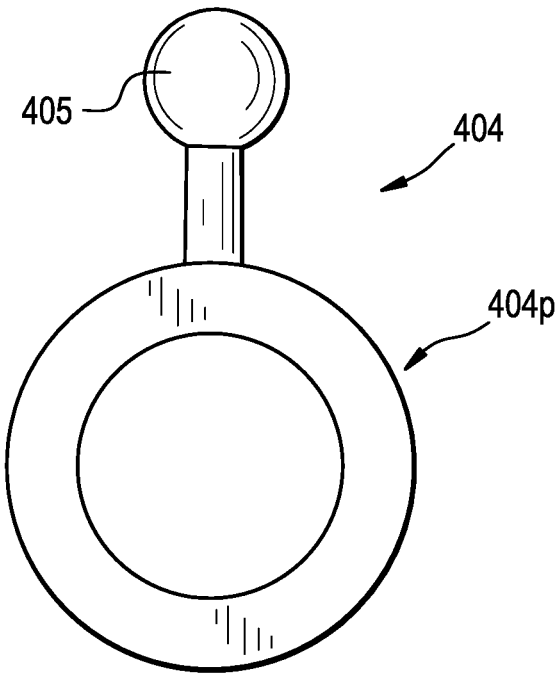
FIG. 6C is a top view of an exemplary embodiment of a ring of the surgical access device of FIG. 6A.
Figure 6D:
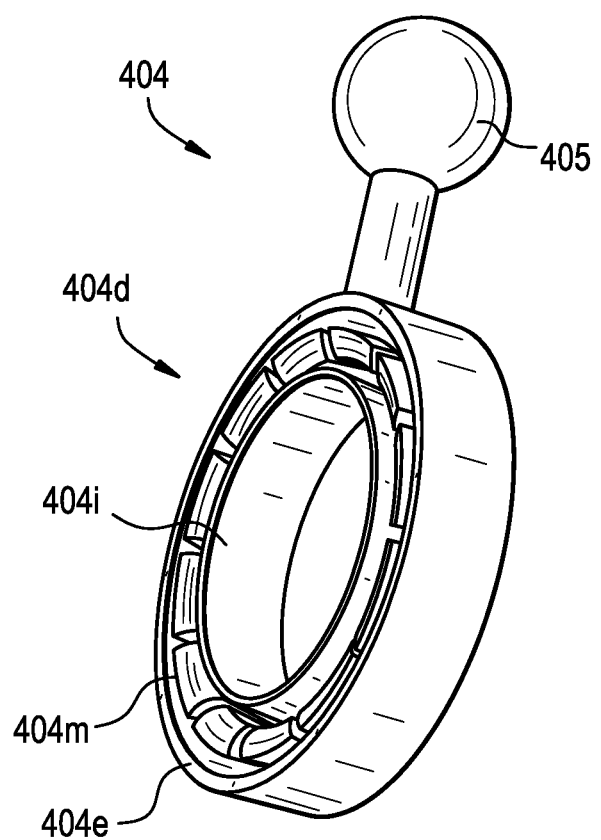
FIG. 6D is a perspective view of the ring of FIG. 6C.
Figure 6E:
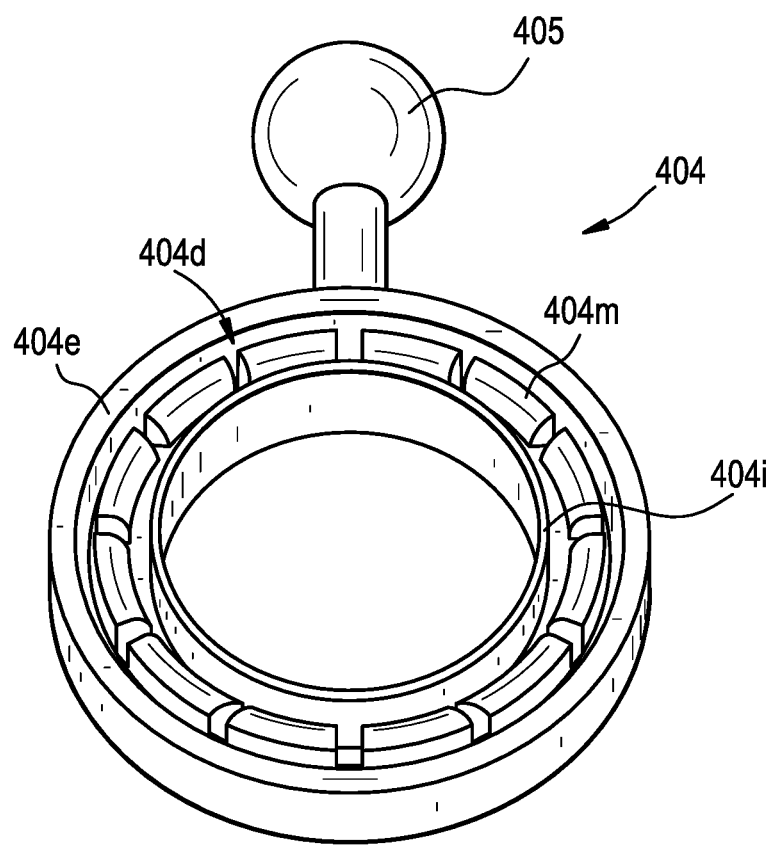
FIG. 6E is a another perspective view of the ring of FIG. 6C.
Figure 7A:
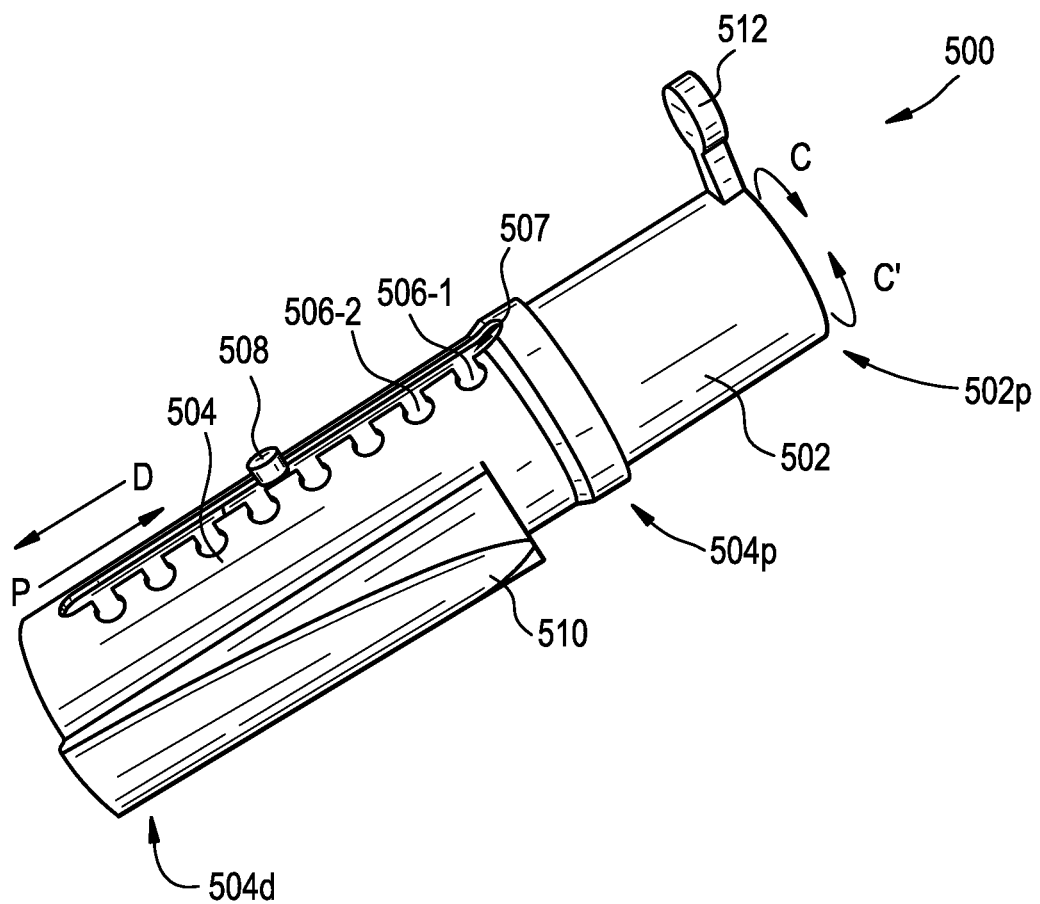
FIG. 7A is a perspective view of another exemplary embodiment of a surgical access device.
Figure 7B:
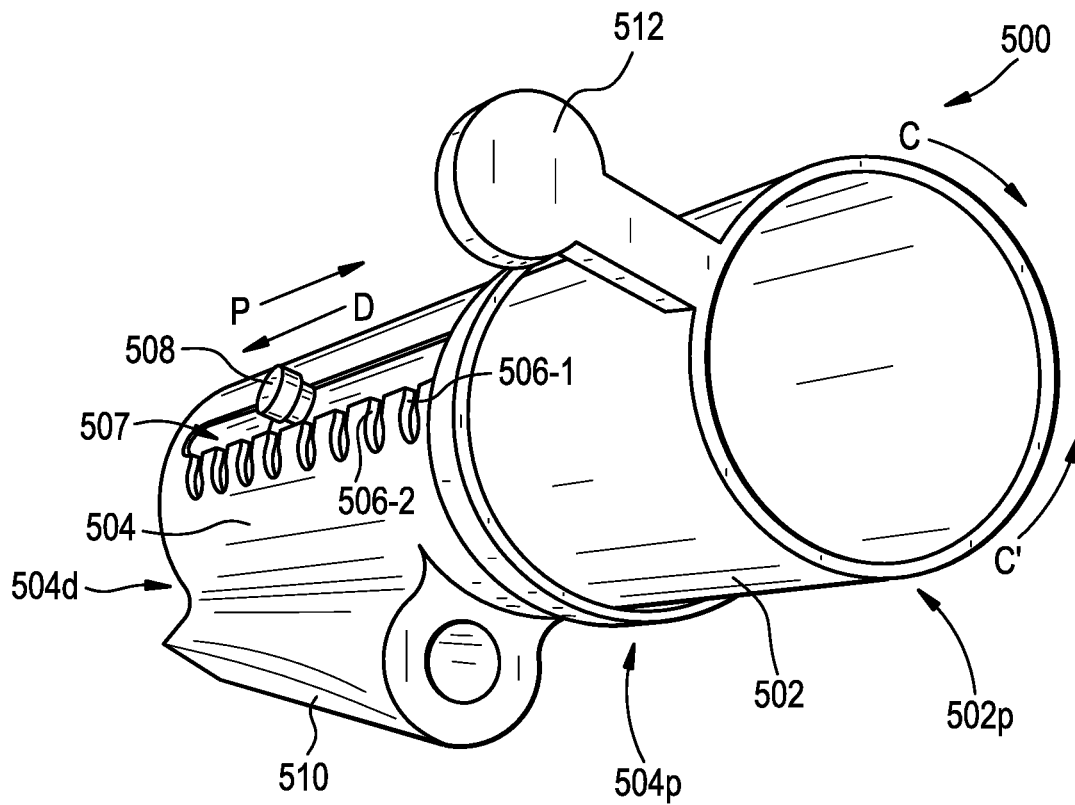
FIG. 7B is another perspective view of the surgical access device of FIG. 7A.
Figure 7C:
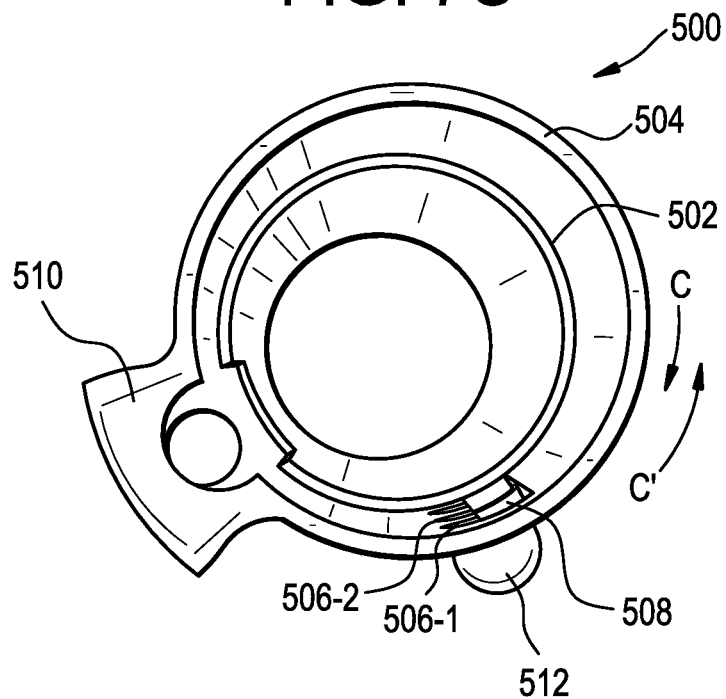
FIG. 7C is a bottom view of the surgical access device of FIG. 7A.
Figure 7D:
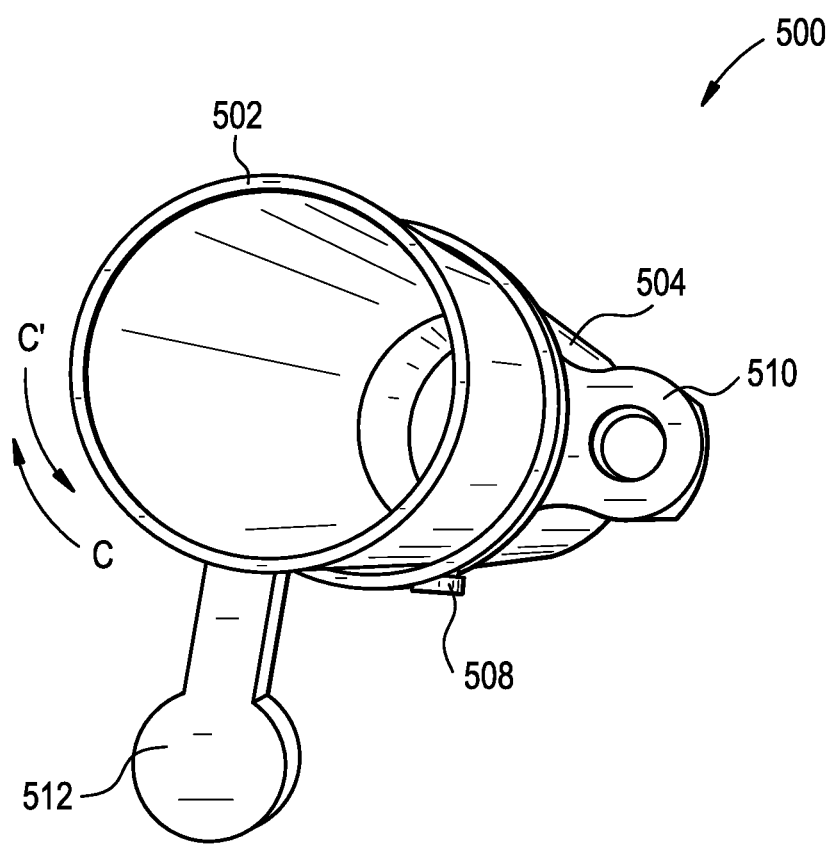
FIG. 7D is another perspective view of the surgical access device of FIG. 7A.

FIG. 5 illustrates another exemplary embodiment of a surgical access device 300 configured to provide operative access to a patient's anatomy. The surgical access device 300 can include a tube or body having an opening or working channel formed therethrough from a distal end 300d to a proximal end 300p. The working channel can be defined by an inner surface of the surgical access device 300. The working channel can be round, square, rectangular, and/or various other shapes, and can have a diameter or circumference of any size, so long as objects (e.g., implants, instruments, or other objects) can be moved to and from the proximal end 300p and the distal end 300d. The shape, diameter, and/or circumference of the working channel can change between the distal end 300d and the proximal end 300p. In other words, for example, the opening at the distal end 300d can be smaller or narrower than the opening at the proximal end 300p of the surgical access device 300. It should be understood that the shape of the access device 300, which is defined by its external surface, can match the shape of the opening (e.g., circle, rectangle, square), or can have a shape that is different than that of the opening.

The surgical access device 300 can be manufactured at a single maximum length determined to reach the deepest area of interest of a patient's body to be accessed during surgery. However, to enable the surgical access device 300 to be used at various lengths as needed to optimally or desirable access shallower regions in a patient's body, the access device 300 can include one or more slits or perforations 308 around at least part of the circumference of the external surface of the access device 300, which facilitate the breaking (e.g., splitting, tearing, separating) of the access device 300 into multiple parts. The perforations 308 can have regions (e.g., circular perforations) that are larger in diameter than the rest of the slits of the perforations, to provide for easier breaking thereat. Breaking the access device 300 into multiple parts can be achieved in various ways, such as by twisting the access device 300 at opposite sides of the selected perforation 308, or bending, folding or applying force to the access device at opposite sides of the selected perforation 308, e.g., about a fixed pivot point equal to the position of the selected perforation 308 on the access device 300.

As shown in FIG. 5, the access device 300 can include a plurality of perforations 308a and 308b formed around part of the circumference of the access device at various positions along the length of the access device 300. Although only two perforations (308a and 308b) are illustrated in FIG. 5, any number of perforations can be provided on the access device 300. The perforations can be provided at regular or irregular intervals along the length of the access device 300. The perforations can be provided starting at the distal end or at the proximal end of the access device 300.

The perforations 308 can be provided around less than the entire circumference of the access device 300 (e.g., 10%, 25%, 33%, 50%, 75%). The perforations can be provided around a part of the circumference of the access device 300 that sufficient to allow for manual breakage of the access device 300 into multiple parts, preferably without any machine or tool assistance.

The length, depth, and width of the perforations 308 can vary between individual perforations on the access device 300, or between different access devices, as deemed necessary or desirable to enable manual breakage. For instance, the length, depth, and width of the perforations 308 can be based on the properties of the material used to manufacture the access device 300, the thickness of the body of the access device 300, the circumference of the access device 300, or other parameters.

The perforations 308 can have a length or other measurement associated therewith and marked on the external surface of the access device 300. These markings can allow a user to identify the resulting length of the access device 300 when the access device is broken at the respective perforation 308. The access device 300 can be configured such that, when it is broken into multiple parts, either the distal end or the proximal end of the original full-length access device 300 can be the resulting access device 300 to be used to access a part of a patient's body.

The access device 300 can be provided without perforations, such that the access device 300 is instead cut at a desired region or length using a machine or tool. The access device 300 can include lines or markings indicating different measurements or lengths at which the access device can be cut using a machine or tool, thereby enabling identification of the resulting length of the access device 300 after it is cut into multiple parts.

Fourth Embodiment

FIGS. 6A to 6E illustrate another exemplary embodiment of a surgical access device 400. As illustrated, the access device 400 can include a main body or tube 402 and a ring portion 404. The main body 402 can be cut, torn, or broken to the desired length, and the ring portion 404 can be attached thereto, e.g., to provide an anchoring point for stabilizing the main body or to cover the broken end of the main body. The tube 402 can be the access device 300 described above, for example, after having been split or cut into multiple parts to obtain a tube of a resulting optimal or desirable size for accessing a patient's target area.

As shown in FIGS. 6A to 6E, the tube 402 can include an opening or working channel formed therethrough, from a proximal end 402p to the distal end 402d. The shape and size of the opening, defined by the inner surfaces of the tube 402, can vary, as described herein. The shape and size of the opening can vary throughout the length of the tube 402. For example, the size of the opening can narrow from the proximal end 402p to the distal end 402d. The shape and size of the access device 400, as defined by its external surfaces, can also vary as described herein.

The ring portion 404 of the access device 400 can be attached or mounted onto the proximal end 402p of the tube 402. The proximal end 402p of the tube 402 can be the cut end of a tube after being cut or divided as described above in connection with FIG. 5. The ring 404, when attached to the tube 402, can provide enhanced handling and stabilizing of the access device 400 as explained in further detail below. The ring 404 can include a proximal side 404p and a distal side 404d. The ring 404 can include one or more concentric walls, e.g., an exterior wall 404e, an interior wall 404i, and a middle wall 404m as shown. The exterior, interior and middle walls 404e, 404i, and 404m can extend distally from the proximal end 404p, lengthwise, to a length deemed sufficient to stabilize the tube 402 and the ring 404 when they are engaged. The length of the walls 404e, 404i and/or 404m can be based on the length of the tube 402. That is, the walls 404e, 404i and 404m can have a length proportional to the length of the tube 402. The length of the walls 404e, 404i, and 404m can vary in size between each other.

The proximal side 404p of the ring 404 can be covered or sealed between the external wall 404e and the internal wall 404, such that the spaces between the walls 404e, 404i and 404m cannot be accessed from a proximal-to-distal direction. The part of the proximal side 404p that is internal or within the internal wall 404i can be open, such that an opening is created through the proximal end 404p to the distal end 404d of the ring 404. The distal side 404d of the ring 404 can be exposed, allowing the spaces between the walls 404e, 404i, and 404m to be accessed or entered from a distal-to-proximal direction, for example, to mount the ring 404 onto the tube 402 as explained in further detail below.

The interior wall 404i can have a smaller circumference than the middle wall 404m and the exterior wall 404e. The middle wall 404m can have a circumference smaller than that of the exterior wall 404e and larger than that of the interior wall 404i. The difference in size between the circumference of the middle wall 404m and the interior wall 404i—i.e., the gap therebetween—can be configured based on the thickness of the tube 402 at its proximal end.

The middle wall 404m can be a fully-closed circle. In other embodiments, such as that shown in FIGS. 6A to 6E, the middle wall 404m can be made up of or can include intermittent or spaced apart wall portions (e.g., 404m-1, 404m-2, etc.) that extend distally from the underside of the ring 404, and that form the wall 404m. The wall portions can be referred to as "fingers" that extend distally from the distal-facing side of the proximal end 404p of the ring 404. The wall portions of the wall 404m can be flexible and/or resilient such that their distal ends can move radially-inward or radially-outward. For example, the wall portions can flex or deflect away from the interior wall 404i and toward the external wall 404e when pressure is applied thereto as a tube 402 is inserted into the space between the middle wall 404m and the internal wall 404i. Such flexibility of the wall portions can enable insertion of a tube 402 having a thickness equal to or larger than the space between the middle wall 404m and the interior wall 404i, when the wall portions are not deflected from their resting position, to be inserted therebetween.

An internal surface of the middle wall 404m (e.g., the surface of the middle wall 404m facing the internal wall 404i), and or an outer surface of the internal wall can include one or more slits, teeth, or other surface features for engaging the tube 402. The surface features can be directional, e.g., unidirectional, such that the surface features allow insertion of the tube 402 in a proximal direction but resist or prevent removal of the tube 402 in a distal direction. For example, the surface features can include teeth that are angled facing toward the proximal side 404p of the ring 404. In this way, when the tube 402 is inserted from the distal side 404d of the ring 404 toward its proximal side 404p, along the space between the middle wall 404m and the internal wall 404i, the distal-most ends of the teeth of the middle wall 404 can contact and slide along the external surface of the proximal end 402p of the tube 402. In turn, pulling the tube 402 in a distal direction away from the ring 404 can cause the teeth of the wall 404m to penetrate the body of the tube 402, thereby creating or increasing a grip of the ring 404 on the tube 402.

The space between the middle wall 404m and the internal wall 404i can be measured from the distal end of the teeth of the middle wall 404m to the external surface of the internal wall 404i. In some embodiments, the ring 404 can include only an external wall 404e and an internal wall 404i, without a middle wall 404m. In such embodiments, the teeth of the middle wall 404m described above can be provided in the internal surface of the external wall 404e, and the space between the external wall 404e and the internal wall 404i can be configured similar to the space between the middle wall 404m and the internal wall 404i described above, to receive the proximal end 402p of the tube 402.

With the ring 404 mounted on the tube 402, the access device 400 can be more easily gripped by virtue of the larger size of the ring 404 compared to the tube 402. Moreover, the access device 400 can be stabilized using a stabilization feature 405 provided on the ring 404. The stabilization feature 405 can be a structure extending away from the external-facing side of the external wall 404e, and can be shaped in various ways. The stabilization feature 405 can be used to connect or attach the access device 400 to an ipsilateral or contralateral pedicle anchor or anatomical support, to a connector, operating table, or other support feature, which can provide stabilization of the access device. As shown in FIG. 6, the stabilization feature 405 can be shaped like a ball, e.g., in order to connect with a support via a ball and socket joint configuration.

Fifth Embodiment

FIGS. 7A to 7D illustrate another exemplary embodiment of a surgical access device 500. The surgical access device 500 can include an inner tube 502 and an outer tube 504. The inner tube 502 and the outer tube 504 can include openings or working channels formed to and from their respective proximal and distal ends. The openings of the inner and outer tubes 502 and 504, defined by their respective inner surfaces, can vary in size and shape, as described above. The size and shape of the inner and outer tubes 502 and 504, as defined by their external surfaces, can likewise vary in size and shape, as described above. The inner and outer tube 502 and 504 can have similar shapes, and can be sized such that the internal surface of the outer tube 504 has a circumference slightly larger than the circumference of the external surface of the inner tube 502, such that the inner tube 502 can slide within the opening of the outer tube 504 without allowing any or a substantial amount of movement of the inner tube 502 other than along distal and proximal directions.

As shown in FIGS. 7A to 7D, the access device 500 can includes a turn-advance-turn-lock mechanism having a plurality of slots 506-1, 506-2, etc. (collectively "506") formed on the outer tube 504 and a knob 508 or a similar protrusion formed on the inner tube 502. In other arrangements, the slots 506 can be formed in the inner tube 502 and the knob 508 can be formed on the outer tube 504. The knob 508 can be a feature protruding from an external surface of the inner tube 502. The knob 508 can have a shape and size that matches the shape and size of the slots 506, such that the knob 508 can be slid into one of the slots 506 to prevent or resist relative distal and proximal movement between the inner and outer tubes. The thickness of the knob (e.g., the distance which the knob protrudes from the external surface of the inner tube 502) can be at least equal to the thickness of the body of the outer tube 504, as measured from its external surface to its internal surface. While the knob 508 can be provided in any position on the tube, in some embodiments, the knob 508 can be provided on or proximate to the distal end of the inner tube 502, enabling the length of the access device 500 to be maximized.

The access device 500 can include a handle 512 for controlling the sliding and rotation of the inner tube 502 in the manner described in further detail below, and/or for securing the access device 500 to a support in the manner described herein.

The slots 506 of the access device 500 can be formed as holes or perforations through the external and internal surfaces of the outer tube 504. The slots 506 can be formed at regular or irregular intervals along the length of the outer tube 504. The slots 506 can be disposed in the same line as the proximal and distal length of the outer tube 504. The slots 506 can be connected by a path 507, which can enable movement of the knob 508 between the slots 506. Although eight slots 506 are shown in FIGS. 7A to 7D, the outer tube 504 can include any number of slots. The path 507 can be an elongate slot having a longitudinal axis that is parallel or substantially parallel to the longitudinal axis of the access device 500. The slots 506 can be defined as lateral or circumferential extensions of the path 507, and can extend perpendicular to or obliquely from the path 507.

The outer tube 504 can include a sub-tube 510, which can be a tube that is formed on the external surface of the outer tube 504. The sub-tube 510 can be of a smaller size (e.g., length, circumference, and/or other dimensions) and/or shape as the outer tube 504. The size and shape of the sub-tube 510 can change from its distal end 510$d$ to its proximal end 510$p$. An opening or working channel can be formed through the sub-tube 510, to and from its proximal and distal ends 510$p$ and 510$d$. The opening can be configured to provide supplemental access to the patient's surgical area. For instance, the supplemental access provided by the opening can be used to insert an object or tool different than the object or tool inserted through the opening of the outer tube 504. Such separation of openings can be used when it is optimal to maintain the tools or objects separate from one another during surgery. In some embodiments, a camera system can be inserted through the sub-tube 510.

To slidably engage the inner and outer tubes 502 and 504, the inner tube 502 can be inserted into the outer tube 504. The inner and outer tubes 502 and 504 can be manufactured or produced such that the inner tube 502 is pre-inserted into the outer tube 504. To adjust the access device 500 to a desired length, the inner and outer tubes 502 and 504 can be moved or positioned relative to each other, and the desired length locked or fixed by inserting the knob 508 into one of the slots 506.

More specifically, to set the length of the access device 500, the inner tube 502 can be rotated about its central longitudinal axis relative to the outer tube 504 (in a clockwise direction C when viewed from a proximal vantage point) until the knob 508 is positioned on the path 507 and/or adjacent to the edge of the path 507 that is opposite the slots 506. With the knob 508 positioned on the path 507, the inner tube 502 can be moved distally or proximally, relative to the outer tube 504, along illustrated directions D and P. When the inner and outer tubes 502 and 504 are positioned such that the access device 500 is of a desired length, the inner tube 502 can be rotated about its central longitudinal axis relative to the outer tube 504 (in a counterclockwise direction C' when viewed from a proximal vantage point). Rotation of the inner tube 502 in a counterclockwise direction can cause the knob 508 of the inner tube 502 to slide from the path 507 into an adjacent one of the slots 506. If a desired length of the access device 500 results in the knob 508 being adjacent to a wall separating two of the slots 506, the inner tube 506 can be further moved distally or proximally to slide the knob 508 into one of the those two slots 506 (e.g., the slot closest to the knob 508). The inner tube 502 can be moved and rotated along directions C, C', P, and D using the handle 512.

With the knob 508 positioned in one of the slots 506, the distal end of the access device 500 can be inserted into a patient's body to reach a desired surgical region, without causing the length of the access device 500 to be modified. That is, the shape of the slots 506 can prevent the distal, proximal, and counterclockwise movement of the inner tube 502 and/or its knob 508 relative to the outer tube 504. Prior to or while the access device 500 is inserted in the patient's body, the length of the access device 500 can be adjusted in the same fashion, by rotating (e.g., clockwise) the inner tube 502, sliding it proximally or distally to achieve a desired length, and rotating the inner tube in the opposite direction (e.g., counterclockwise) to lock its position in another one of the slots 506. The illustrated access device 500 is configured such that the outer tube 504 is generally distal to the inner tube 502. In other arrangements, the inner tube 502 can be generally distal to the outer tube 504.

Sixth Embodiment

Figure 8:
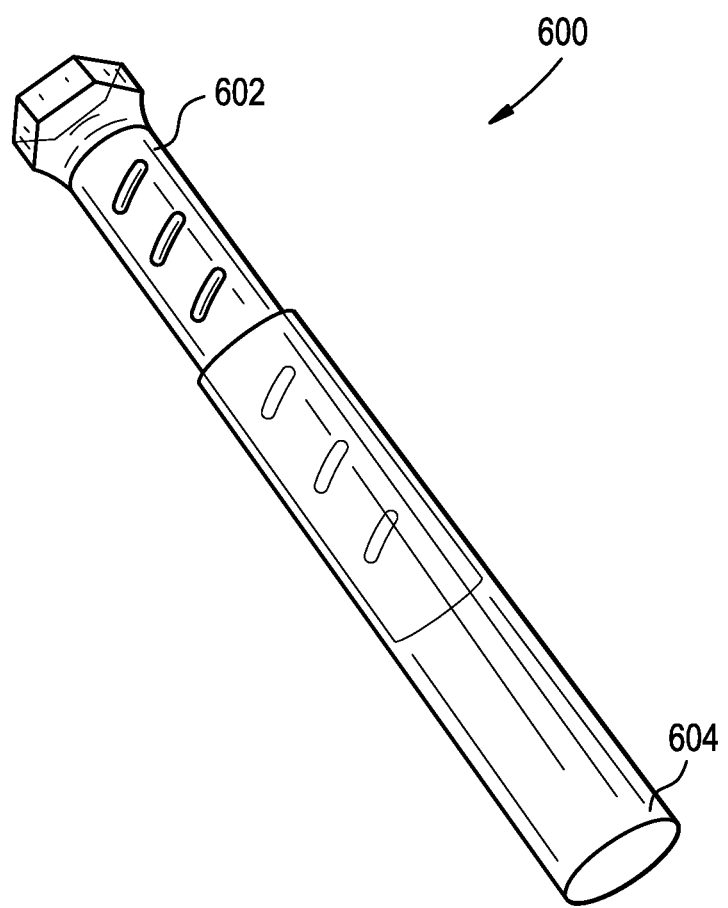
FIG. 8 is a perspective view of another exemplary embodiment of a surgical access device.
Figure 9A:
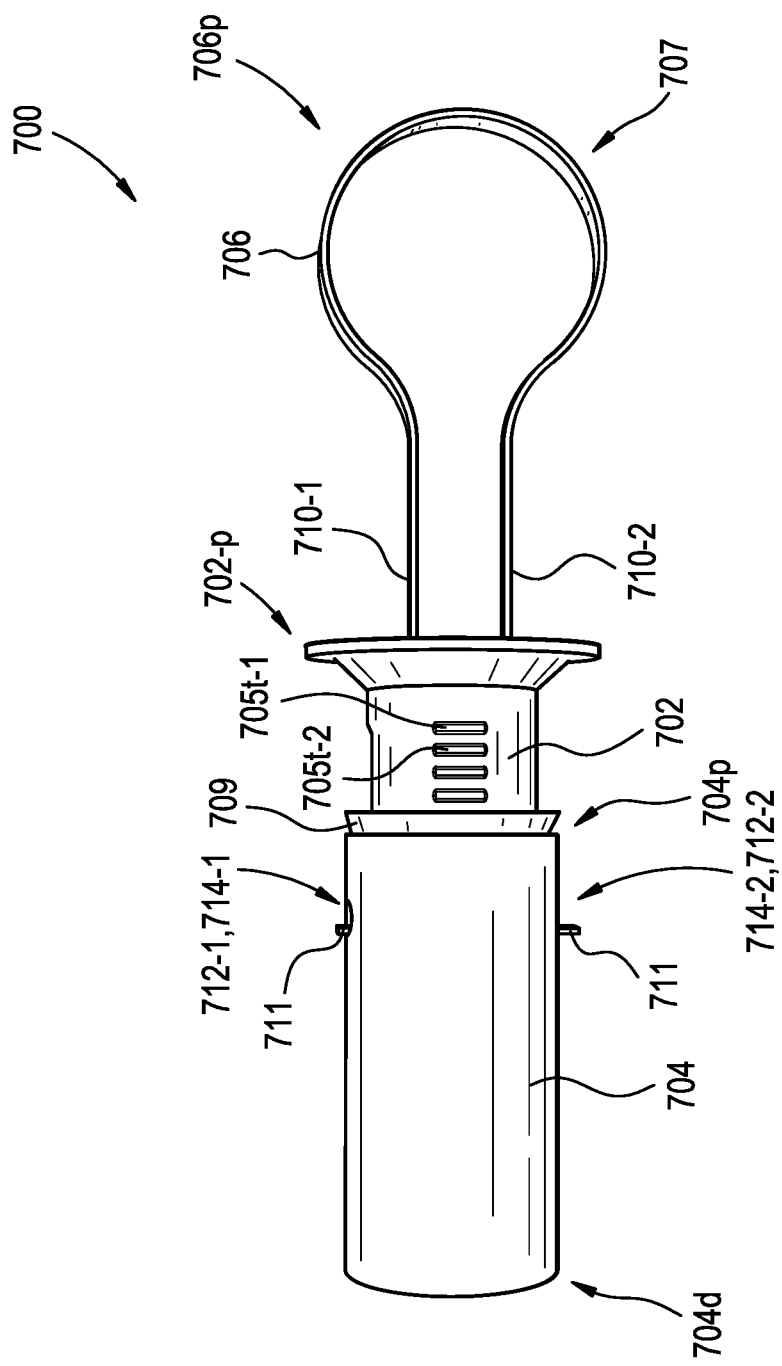
FIG. 9A is a side view of another exemplary embodiment of a surgical access device.
Figure 9C:
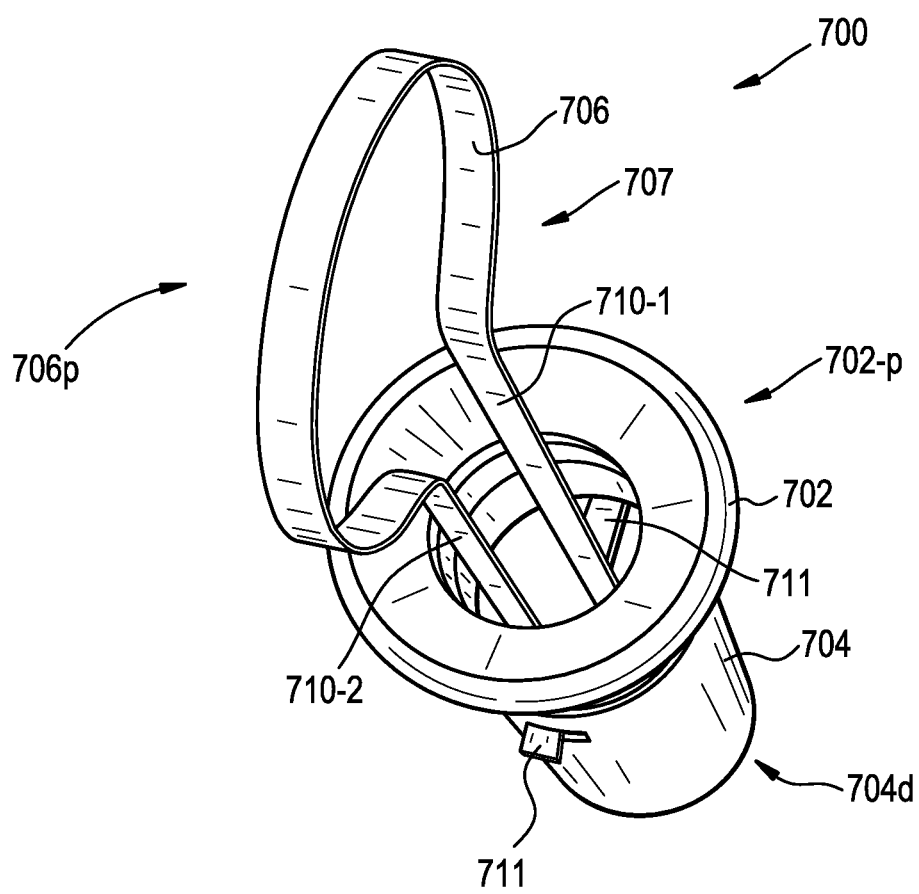
FIG. 9C is another perspective view of the surgical access device of FIG. 9A.
Figure 9D:
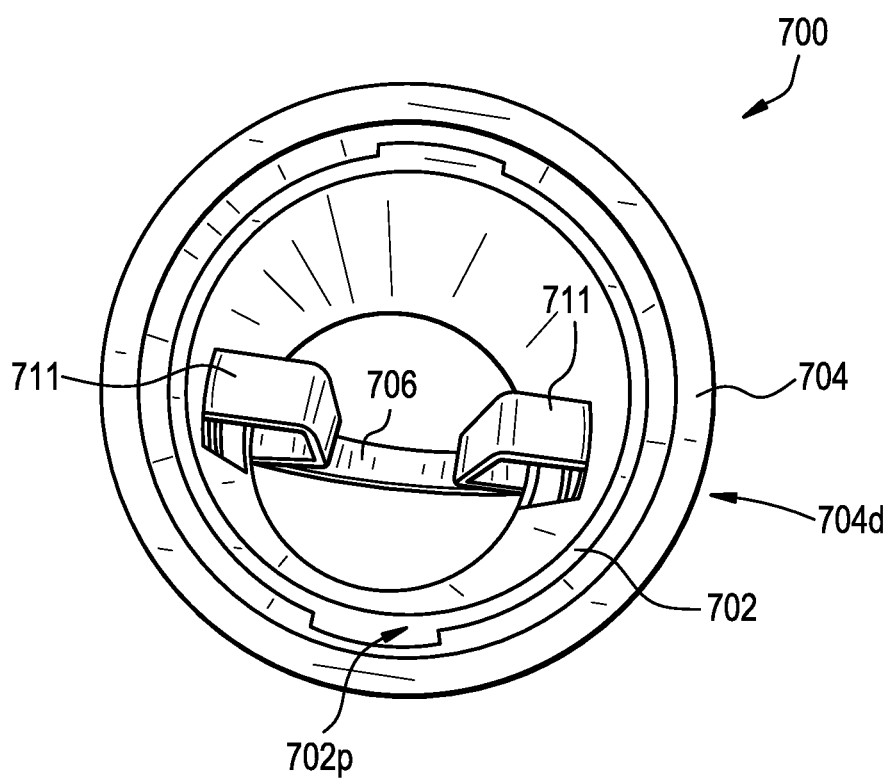
FIG. 9D is another perspective view of the surgical access device of FIG. 9A.
Figure 9E:
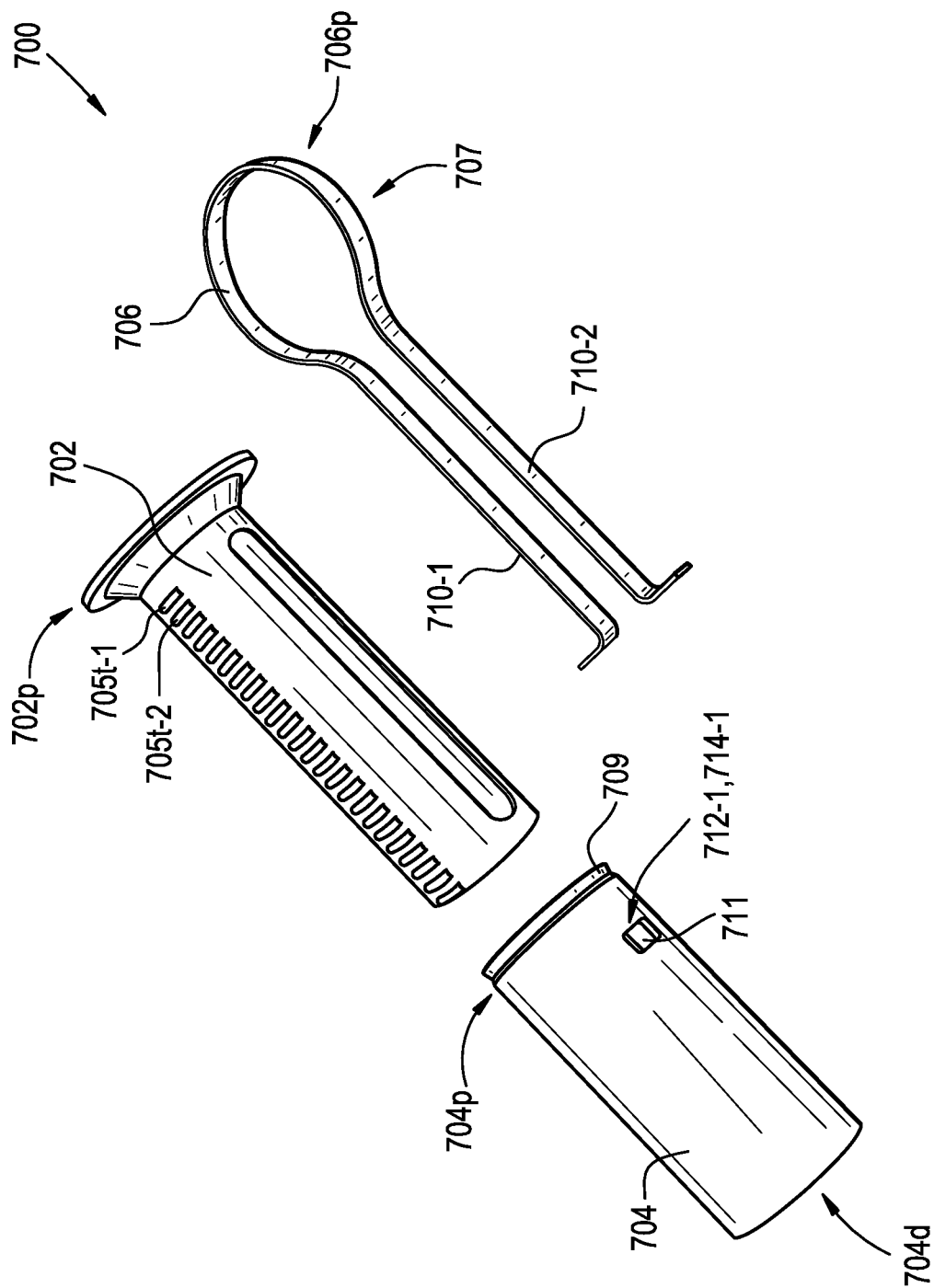
FIG. 9E is an exploded perspective view of the surgical access device of FIG. 9A.

FIG. 8 illustrates another exemplary embodiment of a surgical access device 600. The surgical access device 600 can include an inner tube 602 and an outer tube 604 that are telescopically mated to one another and that define a working channel therethrough. The inner and outer tubes 602, 604 can include engagement features configured to maintain a relative longitudinal position of the inner and outer tubes. The engagements features can be threads that allow an overall length of the access device 600 to be adjusted by threading the inner tube 602 into or out of the outer tube 604. The engagement features can be configured to slip or skip when sufficient force is applied thereto. Accordingly, gross length adjustment can be achieved by simply pushing or pulling the inner and outer tubes with sufficient force to overcome the engagement features. Fine length adjustment can be achieved by threading the tubes into or out of one another.

An external surface of the inner tube 602 and an internal surface of the outer tube 604 can include complementary threads or similar engagement features. The threads can spiral around all or a part of the circumference of the external surface of the inner tube 602 and the internal surface of the outer tube 604. For example, the threads can be formed as an interrupted spiral thread, as shown, having a plurality of gaps between thread segments. The threads can be complementary to each other, such that a male or external thread on one of the tubes 602 or 604 engages with a female or internal thread on the other of the tubes 602 or 604. The threads can be provided on any amount of length on the tubes 602 and 604.

The length of the surgical access device 600 can be adjusted in one or more ways. For example, one way to adjust the length of the surgical access device 600 can be by pulling or pushing, in opposite proximal and distal directions, the inner tube 602 and the outer tube 604, with sufficient force to cause the thread of one of the tubes 602 or 604 to skip or slip over the thread of the other of the tubes 602 or 604. The pulling or pushing can be repeated in order to skip or slip as many threads as needed to place the inner and outer tubes 602 and 604 in a position relative to one another that results in the desired length of the access device 600. One or both tubes 602, 604, or the engagement features thereof, can be formed from a flexible or deformable material to facilitate such slipping. The dimensions or material properties of the tubes 602 and 604, or the engagement features thereof, can be selected to ensure that threads are not slipped or skipped when minimal or incidental force or pressure is applied on the tubes 602 and 604.

Another way to adjust the length of the surgical device can be to rotate the inner tube 602 clockwise or counterclockwise relative to the outer tube 604, e.g., about a central longitudinal axis of the access device 600. Rotating the inner tube 602 relative to the outer tube 604 can cause the threads of the inner and outer tubes 602 and 604 to advance into or out from one another to adjust an overall length of the access device 600. This manner of adjusting the length of the access device 600 can be more controlled and/or can allow for more precise small incremental length adjustment as compared with the above described thread skipping or sliding. The tubes 602 and 604 can be mated in a slight interference fit to resist or prevent relative rotation of the inner and outer tubes 602 and 604 when minimal or incidental rotational force is applied thereto.

When the access device 600 has been adjusted to have a desired length, the access device can be inserted into a patient's body to access a surgical region. The length of the access device 600 can also be adjusted while the access device is inserted into a patient.

Seventh Embodiment

FIGS. 9A to 9E illustrate another exemplary embodiment of a surgical access device 700. The access device 700 can include an inner tube 702, an outer tube 704, and an auxiliary tool 706. As described in further detail below, the length of the surgical access device 700 can be adjusted by moving the inner tube 702 proximally and distally relative to the outer tube 704, and locking the position of the inner tube 702 relative to the outer tube using the auxiliary tool 706.

As shown, the inner tube 702 and the outer tube 704 can include openings or working channels formed therethrough, to and from their distal and proximal ends 702*d* and 704*d*, and 702*p* and 704*p*, respectively. The circumference of the opening of the outer tube 704 at the proximal end 704*p* can be larger than the circumference of an external wall of the inner tube 702 at the proximal end 702*p*, such that the inner tube 702 can be disposed within the outer tube 704 to form a telescoping, slidable engagement therebetween.

The proximal end 702*p* of the inner tube 702 can include or can be formed into a cone-shaped portion or flange. The flange can serve as a stop portion to prevent the distal movement of the inner tube 702, relative to the outer tube 704, beyond the inner tube's proximal end 702*p*. Such a flanging structure of the proximal end 702*p* of the inner tube 702 can also allow the proximal end of the inner tube 702 to be positioned tightly on the surface of the skin of a patient when the access device 700 is inserted into the patient's body.

The inner tube 702 can include one or more ratchet features 705 disposed or formed on the length of the external surface of the inner tube 702. The ratchet features 705 can be disposed on diametrically opposed sides of the external surface of the inner tube 702. The ratchet features 705 can include a plurality of tooth features (705*t*-1, 705*t*-2, etc.; collectively referred to as "705-*t*"), which can define male engagement features protruding from the external surface of the inner tube 702.

The tooth features 705*t* of the ratchet 705 can be configured to engage with or be received within a lip, groove, gap or other like structure 709 formed in the internal surface of the outer tube 704, as described in further detail below. The tooth features 705*t* can be formed along part or the entire length of the inner tube 702. The tooth features 705*t* can be formed along part of the external surface of the inner tube 702 starting at a lengthwise position proximate to the proximal end 702*p* of the inner tube 702. The size and shape of the tooth features 705*t* can vary. The distance or spacing between tooth features 705*t* can be the same or vary between each of the tooth features 705*t*. The shape (e.g., curve, square, triangle), thickness (e.g., amount of protrusion away from the external surface), spacing and/or height (e.g., distance spanned across the length of the external surface of the inner tube 702 by each tooth) of the tooth features 705*t* can depend on the shape, thickness, distance and/or height of the lip 709 formed on the internal surface of the outer tube 704 and vice versa. The width of the tooth features 705*t* can be the same or vary between each of the tooth features, and they can spread over part or the entire circumference of the external surface of the inner tube 702.

The outer tube 704 can include an annular groove or lip 709 for engaging with the ratchet 705 and/or its tooth features 705*t*. As shown in FIGS. 9A to 9D, the lip 709 can be provided around part or the entire circumference of the internal surface of the outer tube 704. The lip 709 can be formed at or proximate to the proximal end 704*p* of the outer tube 704, such that, when engaged with the inner tube 702, the resulting length of the access device 700 can benefit from the rest of the length of the outer tube (e.g., from the lip 709 at the proximal end 704*p* to the distal end 704*d*).

The lip 709 can engage with the tooth features 705*t* to limit or prevent distal and proximal movement of the inner tube and the outer tube 702 and 704 relative to each other. For example, the lip 709 can be a concave feature such as a groove or gap formed on the internal surface of the outer tube 704, extending from the internal surface toward the external surface of the outer tube 704 such that the groove or gap is of sufficient depth to accommodate part or all of a tooth feature 705*t*. In another example, the lip 709 can be formed by the shape of the proximal end 704*p* of the outer tube 704. For instance, when the proximal end 704*p* of the outer tube 704 has a cone shape, the internal surface of the outer tube 704 where the cone shape ends and meets the rest of the internal surface of the outer tube can be convex and/or have a smaller circumference than the rest of the outer tube 704. This narrower or convex portion of the internal surface of the outer tube 704 can be configured to have a circumference smaller than the circumference of the outer-most portion of the tooth features 705*t* and larger than the circumference of the external surface of the inner tube 702 at the regions between the tooth features 705*t*. Such a configuration can allow the narrower portion of the internal surface of the outer tube 704 to be received between two of the tooth features 705t, fixing the position of the outer tube 704 and limiting or preventing the distal and proximal movement of the inner and outer tubes 702 and 704 relative to one another when minimal or incidental force is applied in a proximal or distal direction to the inner and/or outer tubes 702, 704.

To adjust the length of the access device 700 using the ratchet mechanism 705, force can be applied to the inner tube 702 and the outer tube 704 in opposite distal or proximal directions. In other words, pulling the inner tube 702 away from the outer tube 704, pulling the inner tube 702 proximally and the outer tube 704 distally, or pushing the inner tube 704 distally toward the outer tube 704, with sufficient force, can cause the lip 709 on the internal surface of the outer tube 704 to skip or slip past one or more of the tooth features 705t. The pulling and/or pushing of the tubes 702 and/or 704 can be repeated until the lip is fixedly engaged with one or more of the tooth features 705t at a position where the access device 700 is at a desired length. The amount of force needed to slip or skip the lip 709 past a tooth feature 705t can depend on various factors, including the size and/or shape of the lip 709 and/or tooth features 705t, and/or the material of the inner and outer tubes 702 and 704.

An auxiliary tool 706 can be included in the access device 700 to facilitate extension or retraction of the tubes 702, 704 relative to one another. The auxiliary tool 706 can be provided as a length-adjustment feature in addition or alternative to the ratchet 705. As shown in FIGS. 9A to 9D, the auxiliary tool 706 can include a handle portion 707 on the proximal end 706p of the auxiliary tool 706. The auxiliary tool 706 can include two prongs 710 (710-1, 710-2) that extend distally from the handle 707. The distal end of the prongs 710 can include or can be formed as tabs 711 that curve or bend away from one another in a radially-outward direction. The length of the tabs (e.g., the distance that the tabs 711 extend away from their respective prongs 710) and other of their dimensions (e.g., width, thickness) can be based on the thickness of the inner and outer tubes 702 and 704, and/or the size of respective slots 712 and 714 formed on the inner and outer tubes 702 and 704. For example, the tabs 711 can be configured such that they can penetrate through the slots 712 and 714.

The auxiliary tool 706 can be designed such that it is self-spreading, meaning that the prongs 710 are biased apart, e.g., by forming the auxiliary tool from a flexible and resilient material. In a configuration where the prongs 710 are biased apart, the distal ends of the tabs 711 can be separated, in their resting state, by a distance that is larger than the diameter of the internal and external surfaces of the inner and outer tubes 702 and 704. The prongs 710 can be squeezed or compressed, against their bias, to narrow the distance separating the prongs 710 and/or the distal ends of the tabs 711. When squeezed, the prongs 710 and tabs 711 can be separated by a distance smaller than the diameter of the inner tube 702, such that the prongs 710 and 711 can be moved through the inner tube 702 (and/or the outer tube 704), to be inserted through the slots 712 and 714.

The inner tube 702 can include one or more slots 712 (712-1, 712-2) that penetrate through the external surface and internal surface of the inner tube 702. The number of slots 712 can correspond to the number of prongs 710 or tabs 711 provided on the auxiliary tool 706. The slots 712 can be provided on diametrically opposed sides of the inner tube 702, or otherwise to align with the tabs 711—e.g., so that when one of the tabs 711 is positioned through one of the slots 712, another of the tabs 711 can also extend through another of the slots 712 without manipulating the shape of the auxiliary tool 706. The slots 712 can be provided along part of the length of the inner tube 702. The slots 712 can extend from a region proximate to the proximal end 702p toward the distal end 702d. The width of the slots 712 can be at least as large as the width of the tabs 711.

The outer tube 704 can include one or more slots 714 (714-1, 714-2) that penetrate through the external surface and internal surface of the outer tube 704. The number of slots 714 can correspond to the number of prongs 710 or tabs 711 provided on the auxiliary tool 706. The slots 714 can be provided on diametrically opposed sides of the outer tube 704, or otherwise to align with the tabs 711—e.g., so that when one of the tabs 711 is positioned through one of the slots 714, another of the tabs 711 can also extend through another of the slots 714 without manipulating the shape of the auxiliary tool 706. The width of the slots 714 can be the same as or similar to that of the slots 712, meaning at least as large as the width of the tabs 711. The length of the slots 714 (e.g., the distance measured in a proximal to distal direction) can be smaller than the length of the slots 712. The length of the slots 714 can be equal to or slightly larger than the thickness of the tabs 711 (e.g., 200%, 300%, 500%). While the slots 714 can be disposed anywhere along the length of the outer tube 704, in some embodiments, the slots 714 can be formed proximate to the proximal end 704p of the outer tube 704, such that the length of the access device 700 can be optimized.

To adjust the length of the access device 700 using the auxiliary tool 706, the distal end 702d of the inner tube 702 can be inserted within the opening at the proximal end 704p of the outer tube 704. The auxiliary tool 706 can be inserted within the inner tube 702. The slots 712 and 714 of the inner and outer tubes 702 and 704 can be aligned with one another, such that the openings formed by the slots 712 and 714 extend through the inner and outer tubes 702 and 704. Because the prongs and tabs 710 and 711 can be biased apart to a distance that exceeds the diameter of the opening of the inner tube, the prongs of the auxiliary tube 706 can be squeezed or compressed toward one another in order to insert the auxiliary tool 706 into the opening of the inner tube 702. The prongs 710 can then released from their squeezed state, causing the prongs 710 and tabs 711 to spread apart, such that the tabs 711 extend or penetrate through the slots 712 and 714.

With the tabs 711 extending through the slots 712 and 714, the auxiliary tool 706 can be pulled or pushed proximally and distally, using the handle 707, to adjust the length of the access device 700. Because the slots 714 are shorter than the slots 712, pulling or pushing the auxiliary tool 706 causes the proximal or distal surfaces, respectively, of the tabs 711 to engage with the proximal or distal surfaces of the slots 714 of the outer tube 706. Applying a pulling or pushing force on the proximal or distal surfaces of the slots 714 using the tabs 711 can cause the outer tube 704 to move proximally or distally, respectively, relative to the inner tube 702 along the length of the slots 712. When the inner and outer tubes 702 and 704 are positioned relative to one another such that a desired length of the access device 700 is achieved, the pulling or pushing of the auxiliary tool can be ceased. The auxiliary tool 706 can thus be used to remotely or indirectly apply a distally-directing pushing force or a proximally-directing pulling force to the outer tube 704 to move the outer tube axially relative to the inner tube 702. This can be particularly useful when adjusting the length of the access device 700 while it is inserted into a patient, when the outer tube 704 may be disposed deep within the patient, may be surrounded with tissue, or may otherwise be in a position that makes it difficult to manipulate directly. In use, the access device 700 can be adjusted to a first length and can be inserted through an incision formed in the skin of the patient and advanced distally until the flange on the proximal end of the inner tube 702 abuts the skin surface. The auxiliary tool 706 can then be used to apply a distally-directed force to the outer tube 704 to extend the length of the access device 700 to a second length that is greater than the first length. For example, the outer tube 704 can be advanced distally until it bottoms out against a bone surface or other target location. The auxiliary tool 706 can be removed from the access device 700 to provide clear access through the working channel of the access device, or can remain in place during the surgery.

In embodiments in which the access device 700 is also equipped with one or more ratchet features 705, the ratchet features can limit or prevent distal and proximal movement of the inner and outer tubes 702 and 704 relative to one another. In another arrangement, the tabs of the auxiliary tool can engage ratchet teeth on the outer tube. Pulling the tabs radially-inward can disengage them from the ratchet teeth, allowing for length adjustment. Releasing the tabs can allow them spring into engagement with the teeth to limit or prevent length adjustment.

Eighth Embodiment

FIGS. 10A to 10C, and 11A to 11E illustrate another exemplary embodiment of a surgical access device 800. The access device 800 can include a tube or main body having an opening or working channel formed from a proximal end 800p to a distal end 800d. Slits 802 can be formed longitudinally through the body of the access device 800. The slits can penetrate through the external and internal surfaces of the access device 800. The slits 802 can extend from the proximal end 800p distally along the length of the access device 800 to an area prior to the distal end 800d. Bendable arms 804 can be formed longitudinally by the body of the access device 800 positioned between two of the slits 802. In other words, the bendable arms 804 can extend longitudinally along the length of the access device 800, from the proximal end 800p and parallel to the slits 802. While the width of the slits 802 and the bendable arms 804 can vary, the width of the bendable arms 804 can be larger than the width of the slits 802. The bendable arms 804 can allow the length of the access device 800 to be adjusted to a desired or optimal length to reach or provide access to a surgical area in the patient's body, as explained in further detail below.

Figure 11A:
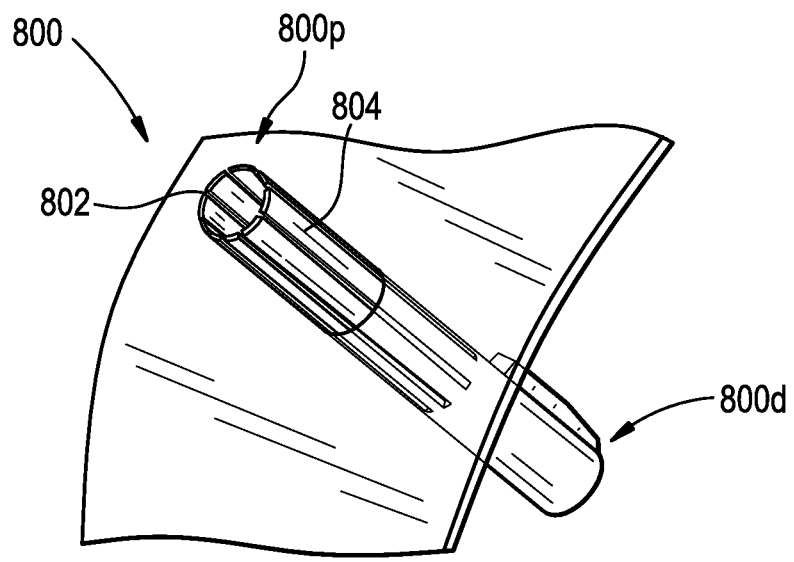
FIG. 11A is another perspective view of the access device of FIG. 10A in a placement state.
Figure 11B:
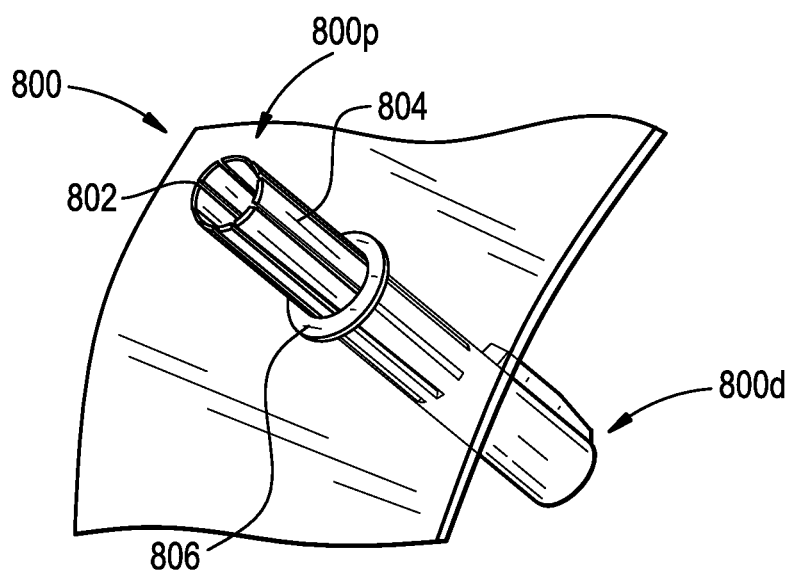
FIG. 11B is another perspective view of the access device of FIG. 11A in a support ring placement state.
Figure 11C:
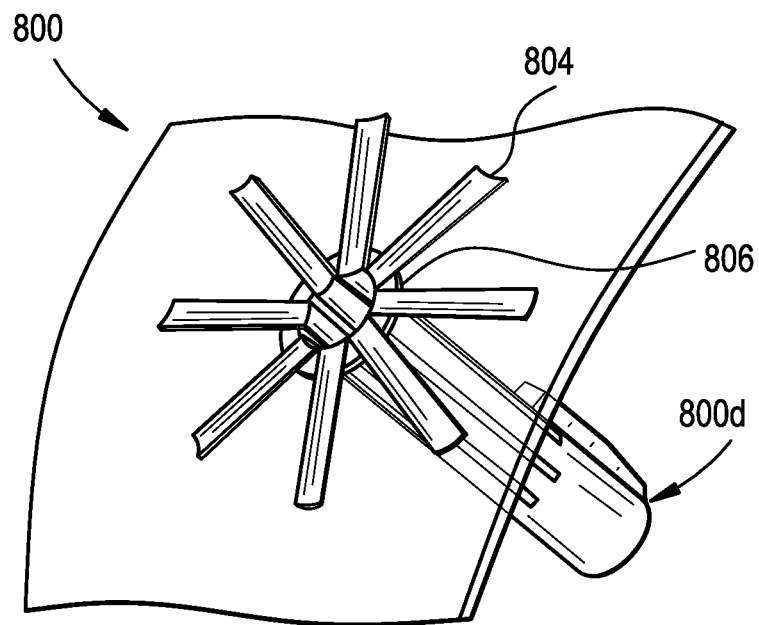
FIG. 11C is another perspective view of the access device of FIG. 11A in a state of bending the bendable arms.

To operate the access device 800 and adjust its length, the distal end 800d of the access device can be inserted into the patient's body to a depth sufficient or optimal to access the surgical area in the patient's body, as shown in FIG. 11A. When the access device 800 is so positioned, the bendable arms 804 extending from the proximal end 800p of the access device 800 can be bent at or relative to a pivot point at or proximal to the surface of the patient's skin, as shown in FIG. 11C.

The access device 800 can include a support ring 806. The support ring 806 can be slidably disposed around the external surface of the access device 800, e.g., with sufficient friction such that the ring 806 cannot be proximally or distally moved relative to the access device 800 without applying force thereto. To facilitate the bending of the bendable arms 804, the ring can be inserted over the access device 800 and slid along an exterior surface thereof to position the ring in contact with the skin surface, as shown in FIG. 11B, or at any other desired longitudinal position along the access device. The ring 806 can be positioned such that its distal end is below the surface of the patient's skin, and its proximal end is above the surface of the patient's skin. The ring 806 can be positioned entirely beneath the skin, or can be spaced proximally from the skin. The bendable arms 804 can be folded over the ring, allowing the arms to be more easily and evenly bent against the edge of the proximal side of the ring 806, as shown in FIG. 11C. With the arms 804 bent at or proximate to the surface of the patient's skin, distal movement of the access device 800 relative to the patient's body can be prevented.

Figure 10A:
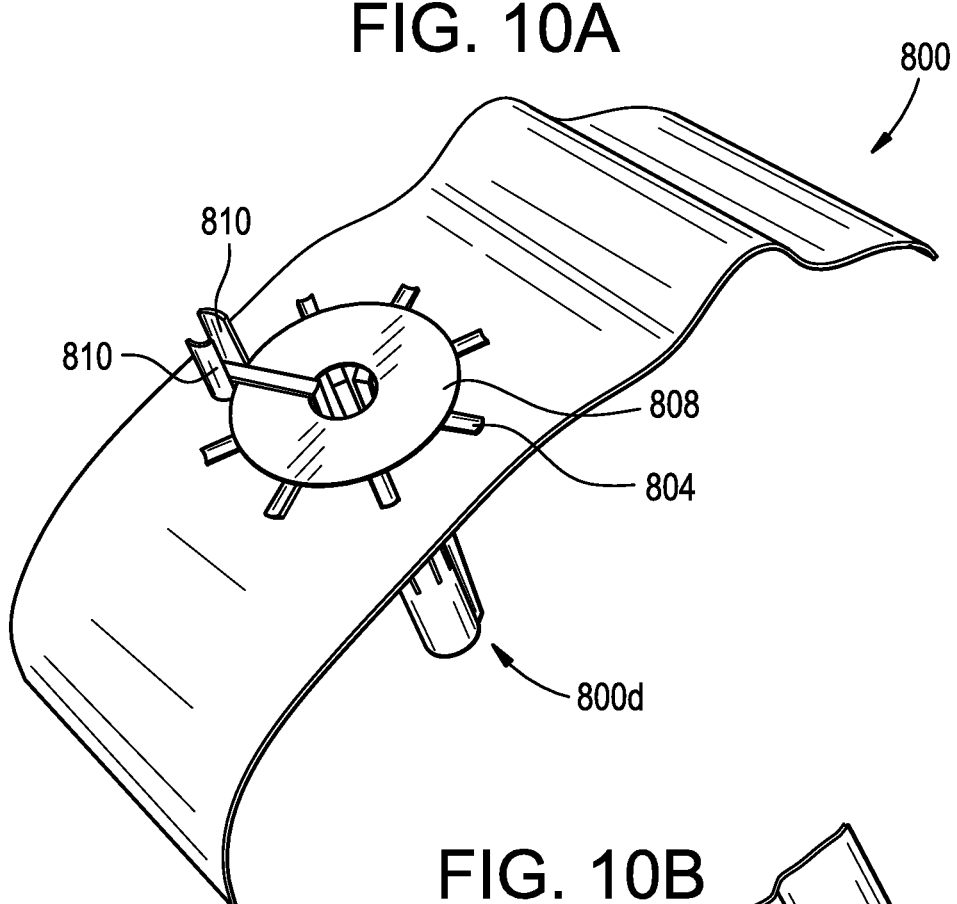
FIG. 10A is a perspective view of another exemplary embodiment of an access device, shown inserted through a skin surface of a patient and secured to a remote anchor point.
Figure 10B:
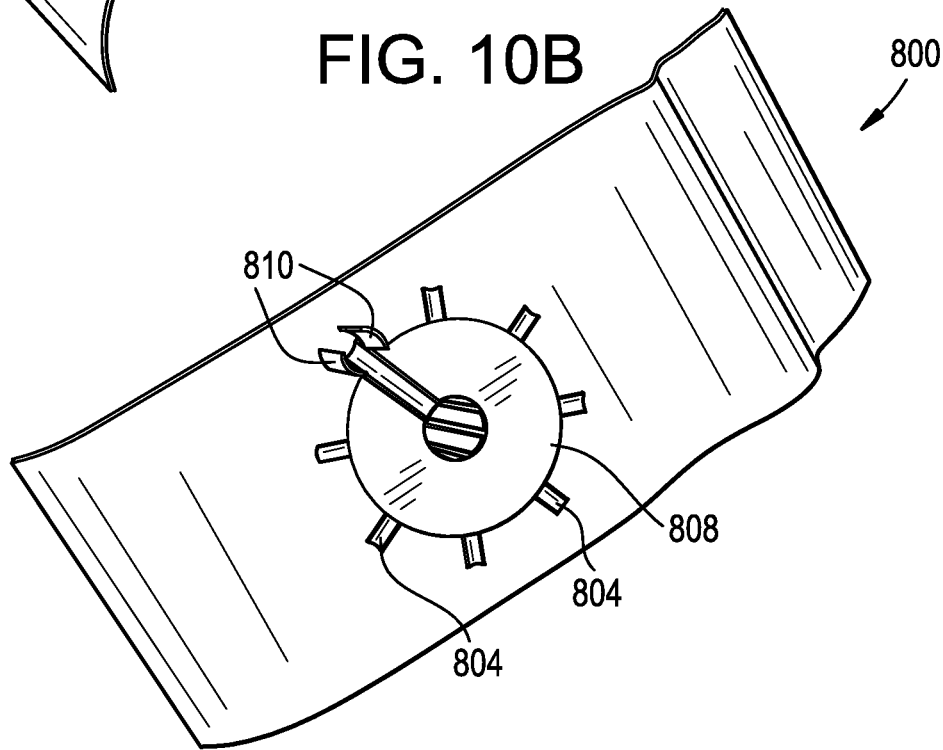
FIG. 10B is another perspective view of the access device of FIG. 10A.
Figure 10C:
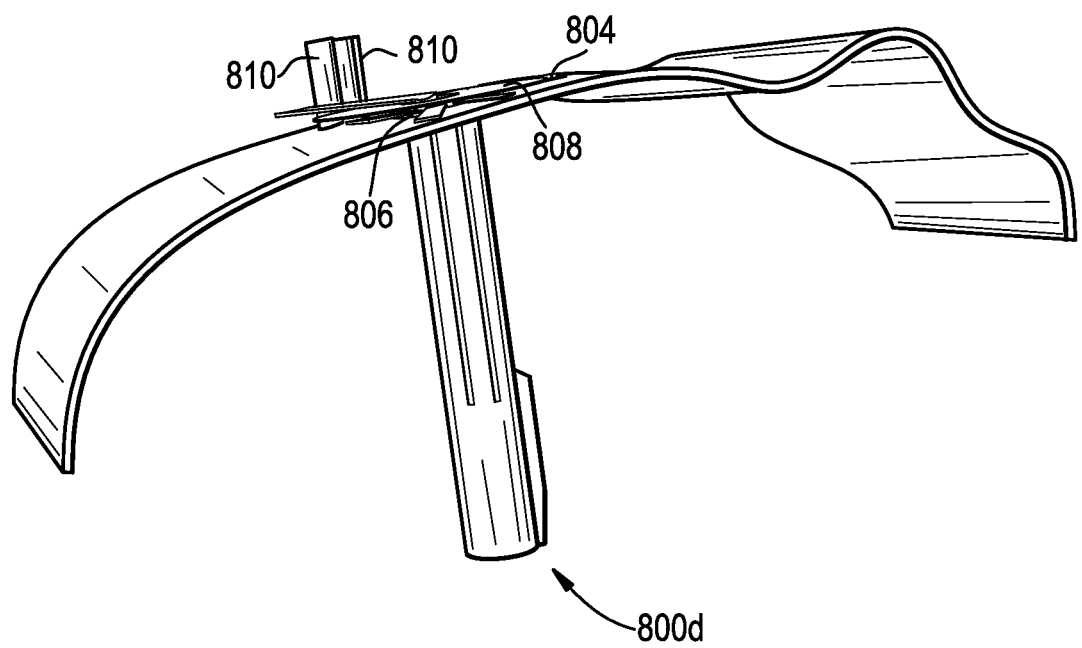
FIG. 10C is another perspective view of the access device of FIG. 10A.
Figure 11D:
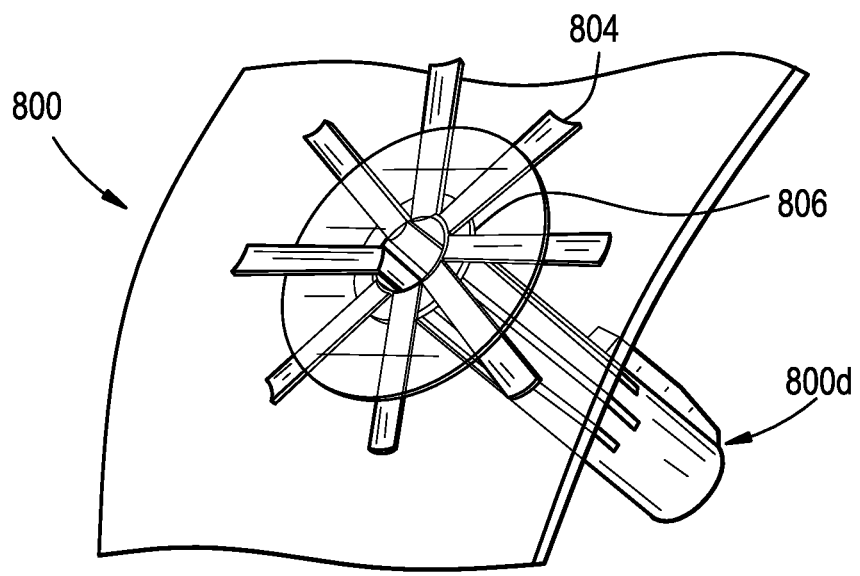
FIG. 11D is another perspective view of the access device of FIG. 11A in a state of attaching the bendable arms to the patient.
Figure 11E:
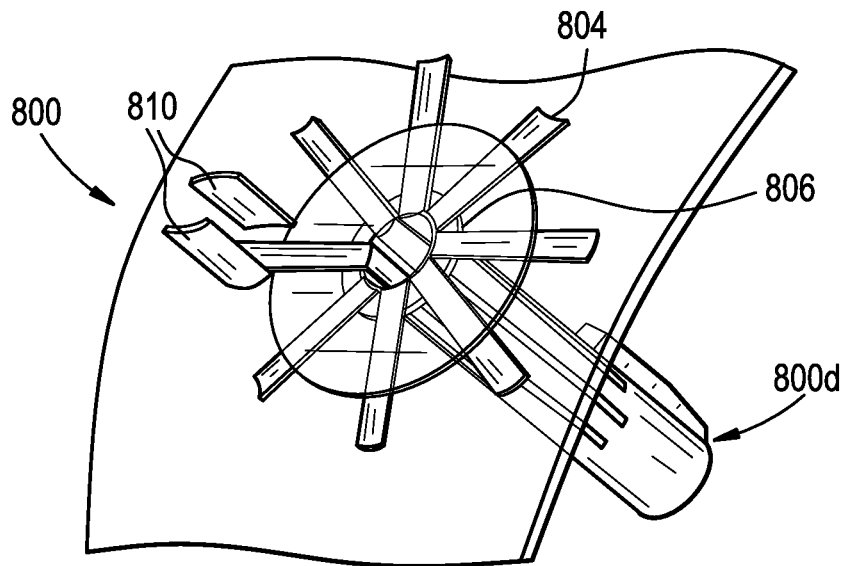
FIG. 11E is another perspective view of the access device of FIG. 11A in a state of attaching a bendable arm to a remote anchor point.

To stabilize the access device 800 and prevent its movement once the bendable arms 804 have been bent, one or more of the arms can be attached or affixed to the patient, e.g., to the skin of the patient. For example, an adhesive, tape, sutures, or other fixing tools or techniques can be applied over one or more of the bendable arms 800, as shown in FIG. 11D. In some embodiments, as shown in FIG. 10A, a circular adhesive disc 808 can be placed over the bendable arms 800, such that an adhesive side of the disc 808 contacts the bendable arms 800 and the surface of the patient's skin, thereby fixing them to one another. The adhesive 808 can prevent distal or proximal movement, or rotation, of the access device 800 relative to the patient. The adhesive disc 808 can include a central opening to allow access to the working channel of the access device 800.

Additionally or alternatively, the access device 800 can be stabilized to the patient, for example by securing the access device 800 to an anatomical structure of the patient or an implant implanted in the patient. The anchor point can be remote from the access device. The anchor point can be a bone anchor, such as a pedicle or lateral mass screw. The anchor point can be an extension tab or post 810 extending proximally from a bone anchor implanted in the patient to a position outside the patient. The anchor point can be on an ipsilateral or contralateral side of the spine from the access device 800. The anchor point can be a post 810 fixed to a patient's pedicle or other bone and that penetrates through the patient's skin at a region sufficiently close to the access device 800 that the post can receive one or more of the bendable arms 804. The post 810 can be positioned such that a bendable arm 804 can be folded over and positioned between opposed arms of the post, as shown in FIG. 10A. Securing the access device 800 can preventing its radial movement or rotation, and otherwise maintain the access device at a fixed position and/or orientation with respect to the patient. The opposed arms of the post 810 can be spaced apart from one another a distance that is larger than the width of the bendable arm 804, such that the bendable arm 804 can be positioned in the space between the arms. A set screw, fastener, or other closure mechanism can be applied to the post 810 to secure the bendable arm therein. With the bendable arms 804 stabilized, the access device 800 can be operated with minimal or no movement or rotation relative to the patient's body.

Ninth Embodiment

Figure 12:
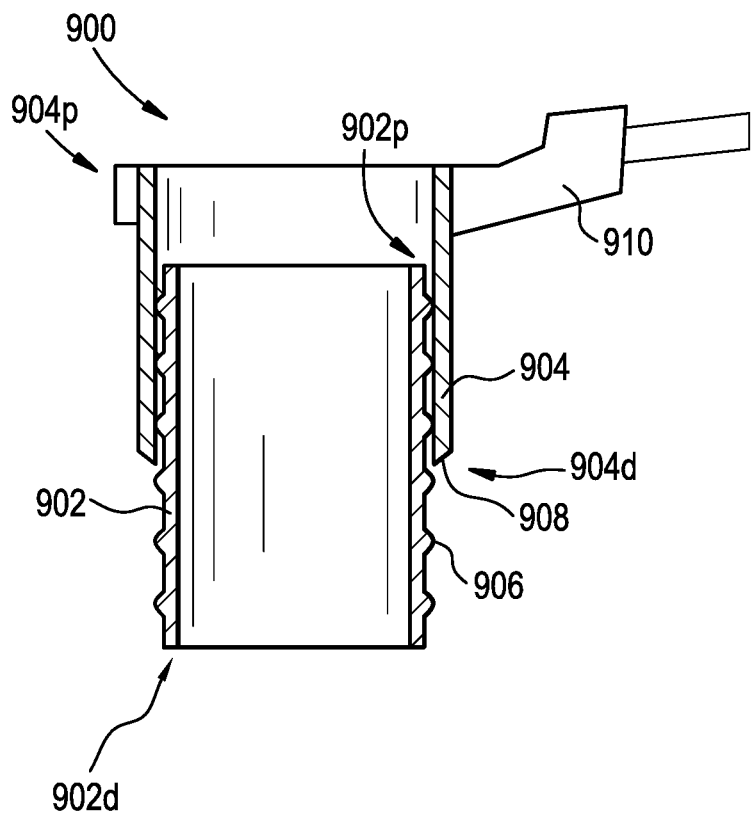
FIG. 12 is a sectional side view of another exemplary embodiment of a surgical access device.

FIG. 12 illustrates another exemplary embodiment of a surgical access device 900. The surgical access device 900 can include an inner tube 902 and an outer tube 904. The inner tube can include proximal and distal ends 902p and 902d; and the outer tube can include proximal and distal ends 904p and 904d. The inner tube 902 and the outer tube 904 can have respective holes or working channels formed therethrough, from their distal to their proximal ends. The inner tube 902 can be slidably engaged within the outer tube 904, such that the two are telescopically mated.

The external surface of the inner tube 902 can include ribs or other engagement features 906 wrapping around all or a part of the circumference of the external surface of the inner tube 902. The internal surface of the outer tube 904 can include counterpart ribs or other engagement features 908 that wrap around all or a part of the circumference of the internal surface of the outer tube 904. The ribbed features 906 and 908 can be convex or concave structures, and the ribbed features of the inner tube 902 can engage with the ribbed features of the outer tube 902. For example, convex ribbed features can engage with two opposing convex features (e.g., by being positioned between the two convex features), or can engage with an opposing and complementary concave feature (e.g., by being positioned within the concave feature).

The shape and size of the ribbed features 906 or 908 can be based on the shape and size of the opposite and complementary ribbed features 906 and 908. For example, convex features can protrude, away from the external surface of the inner or outer tube 902 and 904, a distance equal to the depth of a complementary concave feature, or a distance equal to the amount of protrusion of the complementary convex features. The shape, size, and/or material properties of the ribbed features can be selected to allow the ribbed features 906 and 908 to skip or slip past or over each other as the inner and outer tubes 902 and 904 are moved proximally and distally relative to one another when opposite distal and proximal forces are applied to the inner tube 902 and the outer tube 904. In other words, the ribbed features 906 and 908 can function like a ratchet by allowing the ribbed features to skip or slip one another when proximal and/or distal force is applied to the inner and outer tubes 902 and 904.

The proximal end 904p of the outer tube can include attached thereto or formed thereon a collar or handle 910 portion that can enable the access device 900 to be connected to an anchor or similar stabilization device. The anchor or stabilization device can have a fixed position relative to on object or the patient's body.

The length of the access device 900 can be adjusted prior to or during the access device 900 being inserted into the patient's body.

Tenth Embodiment

Figure 13A:
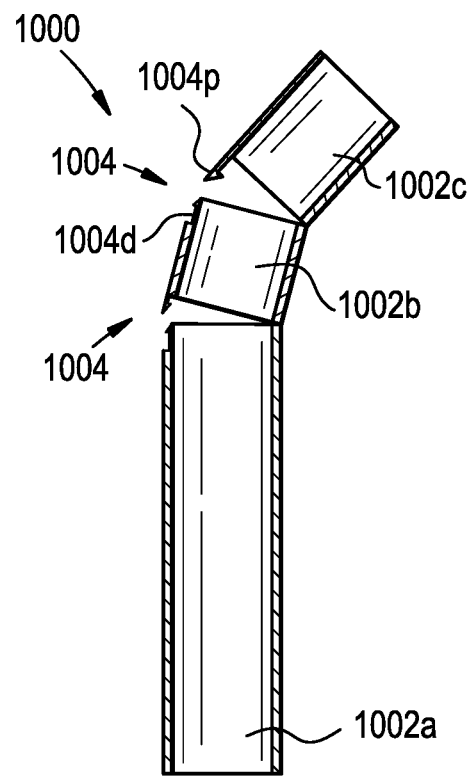
FIG. 13A is a side view of another exemplary embodiment of a surgical access device, in a snapped-in configuration.
Figure 13B:
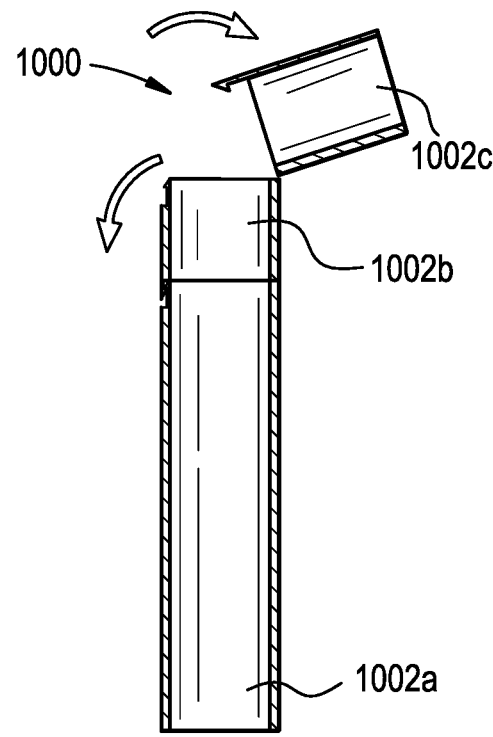
FIG. 13B is another side view of the surgical access device of FIG. 13A in an unsnapping configuration.
Figure 13C:
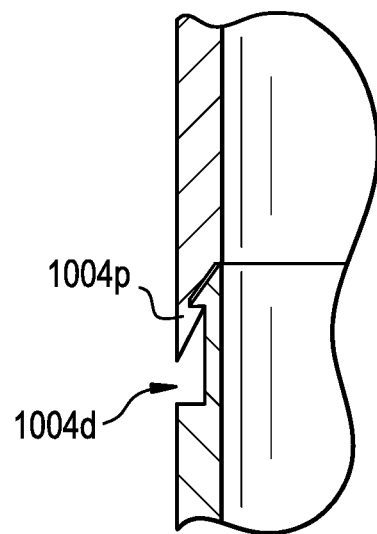
FIG. 13C is a sectional side view of a snap feature of the surgical access device of FIG. 13A.

FIGS. 13A to 13C illustrate another exemplary embodiment of a surgical access device 1000. The surgical access device 1000 can include a tube having a distal end and a proximal end 1000d and 1000p, respectively. A part of the tube can be formed from or can include a plurality of segments, such as segments 1002a, 1002b and 1002c (collectively "1002"). As explained below, the segments 1002 can be attached and/or detached from one another to achieve a tube of a desired or optimal length for surgery. The segment at the distal end 1000d—namely segment 1002a in FIG. 13A, can be the longest of the segments and the one that is to be inserted into the patient's body for surgery.

The segments 1002 can be attachable and detachable using film joint and/or snap fit features 1004 that connect two of the segments 1002. The snap fit features 1004 can include a protruding part 1004p (e.g., hook, stud, bead) on one segment and a mating depression part (e.g., undercut) 1004d on the other segment. The protruding part and depression parts can be provided on either a distal or a proximal one of two segments. Two segments can be connected by one or more snap fit features 1004. The length of the protruding part can be configured to be long enough to reach the corresponding depression. The depth of the depression can be large enough to accommodate the protruding part.

Two segments can be detached by pulling the two segments apart from each other. The snap fit features 1004 can be configured such that a predetermined amount of force allows the two segments to be separated without extreme or machine force being needed. The force to be applied to separate two segments can be a pulling force away from the two parts of the snap features 1004, while pivoting at a diametrically opposed end of the two segments. Two segments can be attached by pushing the two segments toward each other, such that the two parts of the snap fit features 1004 can snap within one another.

When two segments are connected, the snap fit features can be configured to create or maintain a smooth, constant external surface of the access device 1000. Segments can be detached or attached as described above until a desired length of the access tube 1000 for surgery is achieved. The segments can be formed from a flexible or bendable material, such that the snap fit features are deformable during assembly or disassembly to allow the segments to be attached or detached. The segments can be formed from a rigid material and can be permanently broken when separated from one another.

Eleventh Embodiment

Figure 14:
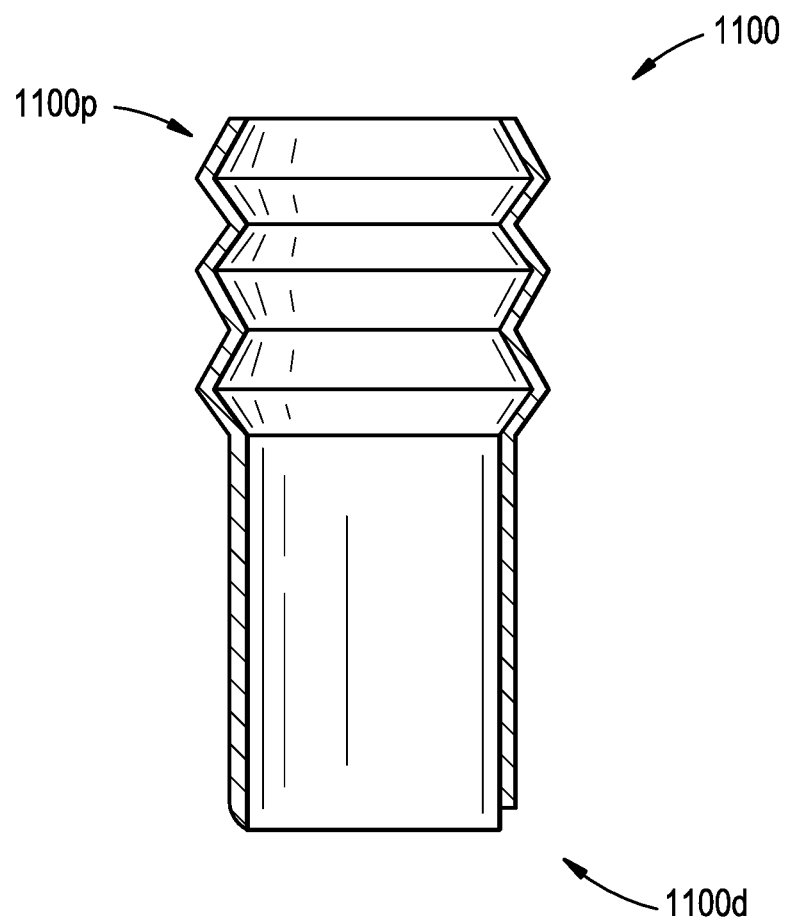
FIG. 14 is a side view of another exemplary embodiment of a surgical access device.

FIG. 14 illustrates another exemplary embodiment of a surgical access device 1100. The surgical access device 1100 can include a tube having a distal end 1100d and a proximal end 1100p. Part of the access device 1100 proximate to the proximal end 1100p can be circumferentially corrugated with bellows or accordion features 1102 similar to those of a drinking straw.

The length of the access device 1100 that is corrugated can vary as needed to achieve a desired stability and length of the access device 1000. Likewise, the inward depth and/or protrusion of the corrugations can vary in order to achieve a desired strength of each corrugated feature, and/or to adjust the force needed to shorten and lengthen the access device 1000.

The access device 1000 can be lengthened by applying axial tension or pulling force to opposite sides of the corrugated features. The access device 1000 can be shortened by applying axial compression or pushing force to opposite sides of the corrugated features. The pulling and pushing forces can be repeated until the desired length of the access device 1000 is achieved.

Twelfth Embodiment

Figure 15A:
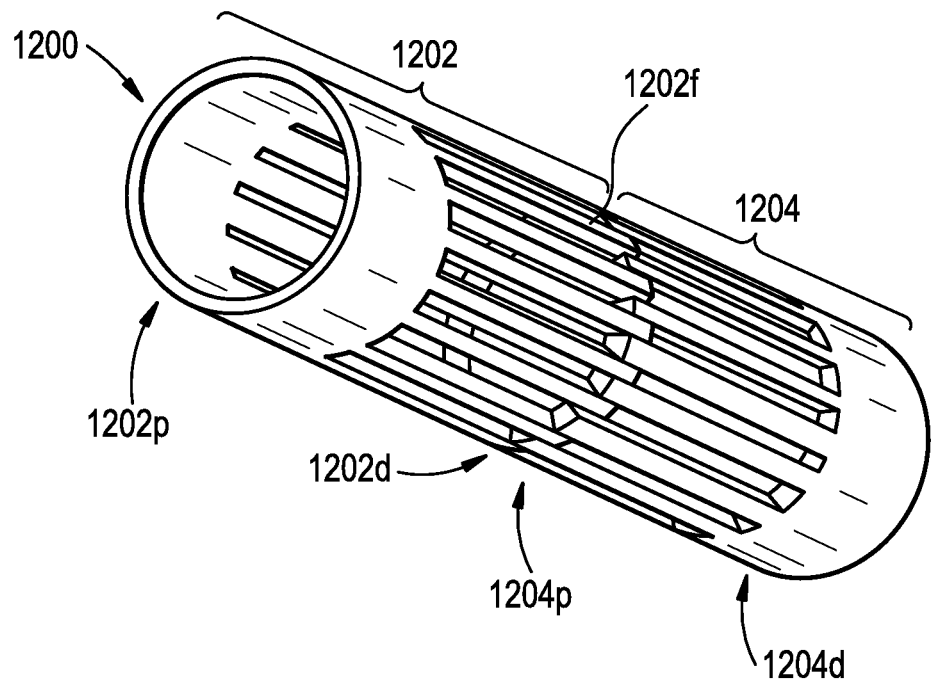
FIG. 15A is a perspective view of another exemplary embodiment of a surgical access device.
Figure 15B:
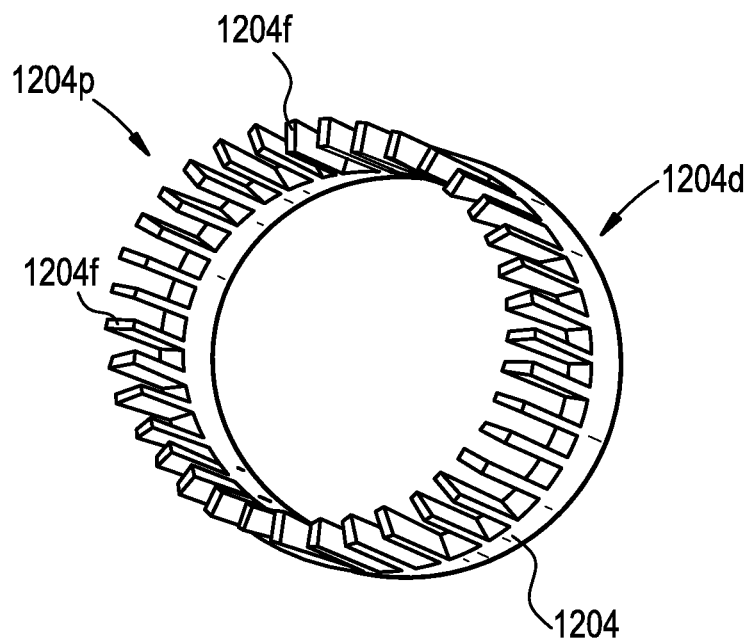
FIG. 15B is a perspective view of an unattached tube of the surgical access device of FIG. 15A.

FIGS. 15A and 15B illustrate another exemplary embodiment of a surgical access device 1200. The access device 1200 can include two or more tubes 1202 and 1204. The tubes 1202 and 1204 can be connected via interdigitating fins or fingers 1202f and 1204f, respectively, as described below. The fingers can engage one another with sufficient friction to maintain the access device 1200 at a fixed overall length when subjected to forces typically associated with surgery through an access device. The length of the access device 1200 can be adjusted by sliding the proximal and distal tubes 1202, 1204 relative to one another to increase the engaged length of the fingers (and reduce the overall length of the access device) or to decrease the engaged length of the fingers (and increase the overall length of the access device).

As shown in FIGS. 15A and 15B, the tubes 1202 and 1204 can have respective distal ends (1202d, 1204d) and proximal ends (1204p, 1204p). One or more of the ends of the tubes 1202 and 1204 can include cantilevered fingers 1202f and 1204f that extend from the other end of the tube. For instance, in FIG. 15B, the tube 1204 is shown. The distal end 1204d can define a fully closed ring, from which the fingers 1204f extend toward and/or to the proximal end 1204p. The fingers 1204f can extend from the distal end 1204d or from an area between the distal end 1204d and the proximal end 1204p.

The fingers 1204f have a same size and shape as one another, and can have the same size and shape as the spaces or gaps separating them. Likewise, the size and shape of the fingers 1202f, and of the gaps separating the fingers 1202f, can match each other and the fingers 1204f. The fingers 1202f and 1204f can have a slightly different size than the gaps separating them, allowing the fingers of one of the tubes 1202 and 1204 to slide within or between the gaps of the other tube 1202 and 1204. The sizes and shapes can be configured such that a sufficient amount of surface area and associated friction between fingers of one tube and fingers of another tube can be achieved, to prevent the distal and proximal movement of the tubes 1202 and 1204 relative to one another when minimal or incidental force is applied thereto.

That is, the fingers and gaps of the tubes 1202 and 1204 can be designed such that they can engage with each other by sliding therebetween. In other words, the fingers 1202f of one tube 1202 can slide between the fingers 1204f of the other tube 1204. The two tubes can be pulled from and pushed toward one another to engage a shorter or larger length of the fingers 1202f and 1204f, until the desired length of the access device 1200 is achieved.

The inner diameters or circumferences of the tubes 1202 and 1204 can be the same. Thus, when the fingers 1202f and 1204f are engaged, the inner diameter or circumference of the access device 1200 can remain constant throughout its length, forming a continuous and smooth internal surface of the access device 1200. The outer diameters or circumferences of the tubes 1202 and 1204 can be the same. Thus, when the fingers 1202f and 1204f are engaged, the outer diameter or circumference of the access device 1200 can remain constant throughout its length, forming a continuous and smooth external surface of the access device 1200.

The access device 1200 can advantageously maximize the working channel inside diameter available for a given external diameter and wall thickness of the access device. In other words, because the proximal and distal tubes can have the same internal diameter and the same external diameter, space that would be otherwise occupied by one of the tubes in a telescoping-type access device is free to be used as part of the working channel.

Connection Features

Any of the access devices described herein can include a connection feature. The connection feature can be used to secure the access device relative to the patient or another reference. The connection feature can be a spherical body connected to the access device by a cantilevered beam. The connection feature can be disposed adjacent a proximal end of the access device. The connection feature can be an external surface of the access device configured to be received between opposed jaws of a connector or clamp. The connection feature can be a recess or cut-out formed in a sidewall of the access device.

Figure 16:
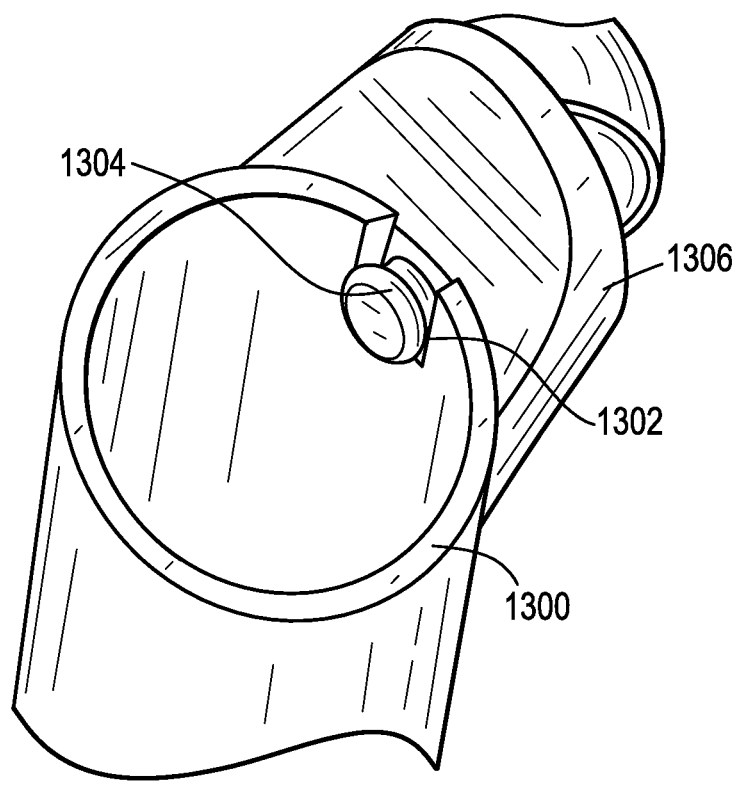
FIG. 16 is a perspective view of an exemplary connection feature of a surgical access device.

FIG. 16 illustrates an exemplary embodiment of a connection feature 1302 and counterpart connector. Any of the access devices described herein can include the connection feature 1302

The connection feature can be defined by a cutout 1302 formed in a sidewall of an access device 1300. The cutout 1302 can be open to a proximal end 1300p of the access device and can extend toward a distal end of the access device. The cutout 1302 can penetrate from an external surface of the tube 1300 to the internal surface. The cutout 1302 can include a path or slot portion extending from the proximal end 1300p, and a circular resting portion at the distal most end of the cutout. The distal portion of the cutout 1302 can have a chamfered or conical bearing surface.

The cutout 1302 can be configured to receive a counterpart mating feature of a connector or other support. The counterpart mating feature can include a cone 1304 protruding from a cap 1306. The cone 1304 can have a size and shape that enables the cone or a portion of the cone to slide within the cutout 1302. The cone 1304 can protrude from cap 1306 a length equal to the thickness of the body of the tube of the surgical access device 1300. The cone 1304 can be extendable and retractable from the cap 1306, to allow the cone to be extended when being inserted into the cutout 1302, and retracted to form a tight connection with the tube 1300. The cone 1304 can be coupled to a wire or cable, and tension can be applied to the cable to pull the cone 1304 towards the cap 1306 and into firm engagement with the bearing surface of the cutout 1302. The cone 1304 can taper at an angle that matches that of the chamfered portion of the cutout 1302. The cap 1306 can define a semi-cylindrical recess sized to receive at least a portion of the exterior surface of the access device 1300 therein. The connection feature can form a "zero-profile" connection, such that no portion of the connection feature protrudes from an internal or external surface of the access device 1300.

The cutout 1302 can be provided on one or more tubes of the access devices described herein. The cone and cap 1304 and 1306 can be adjusted to engage with multiple tubes simultaneously.

Any of the devices described herein can include access tubes that vary in structure or operation from what is shown. Any of the devices herein can include an access tube in the form of a closed tubular body. Any of the devices herein can include an access tube in the form of a multi-bladed retractor. The retractor can be configured to radially expand and/or contract. The retractor can include blades that can be toed inward or outward. Exemplary access devices that can be used with, or having features that can be included in, any of the devices herein are described in U.S. Pat. No. 7,491,168, titled "Surgical Retractor Systems and Illuminated Cannulae," issued on Feb. 17, 2009 which is incorporated herein by reference in its entirety. Any of the devices herein can include an access tube that forms less than a full/closed circle, or that has a non-circular transverse cross-section.

The devices herein can be used to deliver flowable material to a site within a patient. The flowable material can be a hemostat. The flowable material can be a gelatin. The flowable material can be SURGIFLO hemostat matrix available from ETHICON. The devices herein can be used to deliver a powdered material to a site within a patient. The powdered material can be a powdered antibiotic, such as vancomycin. The powdered material can be powdered pig bladder. The powdered material can be so-called "pixie dust" or "pixie powder."

It should be noted that any ordering of method steps expressed or implied in the description above or in the accompanying drawings is not to be construed as limiting the disclosed methods to performing the steps in that order. Rather, the various steps of each of the methods disclosed herein can be performed in any of a variety of sequences. In addition, as the described methods are merely exemplary embodiments, various other methods that include additional steps or include fewer steps are also within the scope of the present disclosure.

The devices disclosed herein can be constructed from any of a variety of known materials. Exemplary materials include those which are suitable for use in surgical applications, including metals such as stainless steel, titanium, nickel, cobalt-chromium, or alloys and combinations thereof, polymers such as PEEK, ceramics, carbon fiber, and so forth. The various components of the devices disclosed herein can be rigid or flexible. One or more components or portions of the device can be formed from a radiopaque material to facilitate visualization under fluoroscopy and other imaging techniques, or from a radiolucent material so as not to interfere with visualization of other structures. Exemplary radiolucent materials include carbon fiber and high-strength polymers.

The devices and methods disclosed herein can be used in minimally-invasive surgery and/or open surgery. While the devices and methods disclosed herein are generally described in the context of spinal surgery on a human patient, it will be appreciated that the methods and devices disclosed herein can be used in any type of surgery on a human or animal subject, in non-surgical applications, on non-living objects, and so forth.

While various example embodiments have been described above, it should be understood that they have been presented by way of example, and not limitation. It is apparent to persons skilled in the relevant art(s) that various changes in form and detail can be made therein. Thus, the disclosure should not be limited by any of the above described example embodiments.

In addition, it should be understood that the figures are presented for example purposes only. The architecture of the example embodiments presented herein is sufficiently flexible and configurable, such that it may be utilized and navigated in ways other than that shown in the accompanying figures.

Further, the purpose of the Abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The Abstract is not intended to be limiting as to the scope of the example embodiments presented herein in any way. It is also to be understood that the procedures recited in the claims need not be performed in the order presented.

One skilled in the art will appreciate further features and advantages of the disclosure based on the above-described embodiments. Accordingly, the disclosure is not to be limited by what has been particularly shown and described. All publications and references cited herein are expressly incorporated herein by reference in their entirety.

The invention claimed is:

1. A surgical access device comprising:
an inner tube including one or more engagement features of a first type disposed on an outer surface thereof; and
an outer tube telescopically mated with the inner tube, and including one or more engagement features of a second type formed at least on the inner surface thereof;
wherein the first type of engagement features and the second type of engagement features are complementary to each other, and
wherein a length of the surgical access device is adjusted by applying opposite proximal or distal forces on the inner tube and outer tube, thereby causing the one or more engagement features of the outer tube to slip from the corresponding one or more engagement features of the inner tube to adjacent others of the one or more engagement feature of the inner tube,
wherein a proximal end of the inner tube includes a stop portion configured to abut a proximal end of the outer tube.

2. The surgical access device of claim 1, wherein the one or more engagement features of the inner tube and the outer tube are formed of a deformable material enabling their slipping therebetween.

3. The surgical access device of claim 1, wherein the one or more engagement features of the inner tube and the outer tube are formed around part or all of the circumference of the inner tube and the outer tube, respectively.

4. A surgical access device comprising:
an inner tube having a distal end, a proximal end, and an opening formed therethrough, the inner tube comprising one or more ratchet features disposed along part of a length of an exterior surface of the inner tube, the one or more ratchet features comprising one or more tooth features; and
an outer tube having a distal end, a proximal end, and an opening formed therethrough, the opening at the proximal end of the outer tube being configured to receive the distal end of the inner tube, and the outer tube comprising a lip feature formed around the circumference of the proximal end of the outer tube, the lip feature being configured to engage with one or more of the tooth features of the one or more ratchet features of the inner tube,
wherein a length of the surgical access device is adjusted by applying opposite proximal and distal forces on the inner and outer tubes causes the lip feature of the outer tube to slip over one or more of the tooth features of the one or more ratchet features of the inner tube,
wherein the proximal end of the inner tube is cone-shaped and flanges proximally and externally relative to the rest of the of the inner tube, and
wherein the external surface of the cone shaped portion of the inner tube is configured to contact a surface of skin of a patient's body when the surgical access device is inserted in the patient's body.

5. The surgical access device of claim 4, wherein engaging the lip feature of the outer tube with one or more of the tooth features of the inner tube causes the distal and proximal movement of the inner and outer tube, relative to each other, to be restricted.

6. The surgical access device of claim 5,
wherein a circumference of the internal surface of the outer tube at the lip feature is smaller than a circumference of the external surface of the inner tube at the one or more tooth features.

7. The surgical access device of claim 4,
further comprising an auxiliary tool comprising a handle portion formed at a proximal end thereof, two or more prongs, and two or more tabs formed at corresponding distal ends of the two or more prongs, and the two or more prongs biased apart from one another, wherein the inner tube comprises one or more slots formed along part of the length of the inner tube, through the external and internal surfaces of the inner tube, wherein the outer tube comprises one or more slots formed along part of the length of the outer tube, through the external and internal surface of the outer tube, the one or more slots of the outer tube being shorter than the one or more slots of the inner tube, and wherein the auxiliary tool is engaged with the inner and outer tubes by squeezing the two or more prongs against their bias, proximally and distally moving the auxiliary tool along the opening of the inner tube, and releasing the two or more prongs causing their tabs to extend through the one or more slots of the inner tube and the one or more slots of the outer tube.

8. The surgical access device of claim 7, wherein the length of the surgical access device is adjusted by proximally pulling or distally pushing the auxiliary tool when the tabs are extending through the one or more slots, causing distal or proximal force to be applied on the one or more slots of the outer tube and the distal and proximal position of the outer tube relative to the inner tube to change as the tabs slide along the one or more slots of the inner tube.

9. The surgical access device of claim 7, wherein the proximal pulling or the distal pushing of the auxiliary tool causes the lip feature of the outer tube to slip over one or more of the tooth features of the inner tube.

10. The surgical access device of claim 1, wherein the one or more engagement features of the outer tube is formed by a shape of the proximal end of a body of the outer tube.

11. The surgical access device of claim 10, wherein the proximal end of the body of the outer tube includes a convex portion and the one or more engagement features of the outer tube is formed where the convex portion of the outer tube meets a tubular portion of the outer tube.

12. The surgical access device of claim 1, wherein the one or more engagement features of the outer tube extend from the inner surface of the outer tube towards an outer surface of the outer tube without extending through the outer surface of the outer tube.

13. A surgical access device comprising:
an inner tube having one or more engagement features of a first type disposed on an external surface thereof and at least one slot extending through the external surface and an internal surface of the inner tube;
an outer tube telescopically mated with the inner tube, and including an engagement feature of a second type formed on an internal surface thereof and at least one slot extending through an external surface and the internal surface of the outer tube; and
an auxiliary tool configured to engage with the at least one slot formed in the outer tube and the at least one slot formed in the inner tube to facilitate extension or retraction of the outer tube relative to the inner tube;
wherein a length of the surgical access device is adjusted by applying opposite proximal or distal forces on the inner tube and outer tube, thereby causing the engagement feature of the outer tube to slip from the corresponding one or more engagement features of the inner tube to adjacent others of the one or more engagement feature of the inner tube.

14. The surgical access device of claim 13, wherein the auxiliary tool includes a proximal end and a distal end, the distal end having a first prong and a second prong configured to engage with the at least one slot formed in the inner tube and the at least one slot formed in the outer tube.

15. The surgical access device of claim 14, wherein the first prong and the second prong of the auxiliary tool are biased in a radially-outward direction.

\* \* \* \* \*